(12) United States Patent
Yu et al.

(10) Patent No.: US 10,039,747 B2
(45) Date of Patent: Aug. 7, 2018

(54) TETRAHYDROCYCLOPENTAPYRROLE DERIVATIVES AND A METHOD FOR PREPARING THE SAME

(71) Applicant: Daewoong Pharmaceutical Co., Ltd., Gyeonggi-do (KR)

(72) Inventors: Kyung A Yu, Gyeonggi-do (KR); Ji Sung Yoon, Gyeonggi-do (KR); Deok Ki Eom, Gyeonggi-do (KR); Yeon Im Lee, Gyeonggi-do (KR); Mi Ryeong Han, Gyeonggi-do (KR); Jun Hee Lee, Seoul (KR); Ha Nee Seo, Gyeonggi-do (KR); Ji Duck Kim, Gyeonggi-do (KR); Sang Ho Lee, Gyeonggi-do (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 172 days.

(21) Appl. No.: 14/913,696

(22) PCT Filed: Aug. 29, 2014

(86) PCT No.: PCT/KR2014/008053
§ 371 (c)(1),
(2) Date: Feb. 23, 2016

(87) PCT Pub. No.: WO2015/030514
PCT Pub. Date: Mar. 5, 2015

(65) Prior Publication Data
US 2016/0200681 A1 Jul. 14, 2016

(30) Foreign Application Priority Data
Aug. 29, 2013 (KR) .................. 10-2013-0103471

(51) Int. Cl.
| | |
|---|---|
| *A61K 31/4035* | (2006.01) |
| *A61K 31/4439* | (2006.01) |
| *C07D 209/44* | (2006.01) |
| *C07D 209/52* | (2006.01) |
| *C07D 401/04* | (2006.01) |
| *C07D 401/12* | (2006.01) |
| *C07D 403/04* | (2006.01) |
| *C07D 403/12* | (2006.01) |
| *C07D 471/04* | (2006.01) |
| *C07D 487/04* | (2006.01) |
| *C07D 405/10* | (2006.01) |
| *C07D 409/12* | (2006.01) |
| *C07D 409/14* | (2006.01) |
| *C07D 405/04* | (2006.01) |
| *C07D 405/12* | (2006.01) |
| *C07D 409/04* | (2006.01) |
| *C07D 498/04* | (2006.01) |

(52) U.S. Cl.
CPC ...... *A61K 31/4035* (2013.01); *A61K 31/4439* (2013.01); *C07D 209/44* (2013.01); *C07D 209/52* (2013.01); *C07D 401/04* (2013.01); *C07D 401/12* (2013.01); *C07D 403/04* (2013.01); *C07D 403/12* (2013.01); *C07D 405/04* (2013.01); *C07D 405/10* (2013.01); *C07D 405/12* (2013.01); *C07D 409/04* (2013.01); *C07D 409/12* (2013.01); *C07D 409/14* (2013.01); *C07D 471/04* (2013.01); *C07D 487/04* (2013.01); *C07D 498/04* (2013.01)

(58) Field of Classification Search
CPC ............ A61K 31/4035; A61K 31/4439; C07D 209/44; C07D 209/52; C07D 401/04; C07D 401/12; C07D 403/04; C07D 403/12; C07D 405/04; C07D 405/10; C07D 405/12; C07D 409/04; C07D 409/12; C07D 409/14; C07D 471/04; C07D 487/04; C07D 498/04
See application file for complete search history.

(56) References Cited

U.S. PATENT DOCUMENTS

| | | | |
|---|---|---|---|
| 5,466,811 | A | 11/1995 | Alexander |
| 7,034,018 | B2 | 4/2006 | Gerlach et al. |
| 2002/0161033 | A1 | 10/2002 | Przewosny et al. |
| 2007/0179173 | A1 | 8/2007 | Kuroda et al. |
| 2009/0143444 | A1 | 6/2009 | Kajino et al. |
| 2010/0197721 | A1 | 8/2010 | Vohra et al. |
| 2011/0172275 | A1 | 7/2011 | Nishida et al. |
| 2011/0288040 | A1 | 11/2011 | Hasuoka et al. |

FOREIGN PATENT DOCUMENTS

| | | | |
|---|---|---|---|
| JP | 10502929 | | 3/1998 |
| JP | 2003238565 | * | 8/2003 |
| WO | WO-01/47878 A1 | | 7/2001 |
| WO | WO-2006/025716 A1 | | 3/2006 |
| WO | WO-2007/026916 A1 | | 3/2007 |
| WO | WO-2007/072146 A1 | | 6/2007 |

OTHER PUBLICATIONS

JP-2003238565 Translation.*
Rühe et al., "Conducting Polymers From 3,4-Disubstituted Polypyrroles", Ber. Bunsenges. Phys. Chem., vol. 91, 1987, pp. 885-888.
Radl et al., "Improved Process for Azilsartan Medoxomil: A New Angiotensin Receptor Blocker", Org. Process Res. Dev., vol. 17 Jan. 18, 2013, pp. 77-86.
Aspiotis et al., "The Discovery and Synthesis of Potent Zwitterionic Inhibitors of Renin", Bioorganic & Medicinal Chemistry Letters, vol. 21, 2011, pp. 2430-2436.

(Continued)

*Primary Examiner* — Kara R McMillian
(74) *Attorney, Agent, or Firm* — Marshall, Gerstein & Borun LLP

(57) ABSTRACT

The present invention provides tetrahydrocyclopentapyrrole derivatives that can be used for preventing or treating peptic ulcer, gastritis or reflux esophagitis, a method for preparing the same, and a pharmaceutical composition containing the same.

20 Claims, No Drawings

(56) References Cited

OTHER PUBLICATIONS

Berge et al., "Pharmaceutical Salts", Journal of Pharmaceutical Sciences, vol. 66, No. 1, 1977, 20 pages.
Rabon et al., "Preparation of Gastric H+K+-ATPase., Methods in Enzymology", Academic Press Inc., vol. 157, 1988, pp. 649-654.
Shay et al., "A Simple Method for the Uniform Production of Gastric Ulceration in the Rat", Gastroenterology, 5, 1945, pp. 43-61.
Search Report and Written Opinion in International Application No. PCT/KR2014/008053 dated Dec. 24, 2014, 25 pages.

* cited by examiner

TETRAHYDROCYCLOPENTAPYRROLE DERIVATIVES AND A METHOD FOR PREPARING THE SAME

BACKGROUND OF THE INVENTION (a) Field of the Invention

The present invention relates to tetrahydrocyclopentapyrrole derivatives that can be used for preventing or treating peptic ulcer, gastritis or reflux esophagitis, a method for preparing the same, and a pharmaceutical composition containing the same.

(b) Description of the Related Art

The development of a medicine for peptic ulcer has been focused largely on two kinds (control of aggressive factor, and reinforcement of defensive factor), and among them, a representative treatment method is to control aggressive factor. The development trend gradually led to the development of anticholinergic drug and the development of $H_2$ receptor antagonist from the past development of antacid. Currently, a proton pump inhibitor (PPI) is leading the market.

Since Prout discovered in 1884 that a high concentration of hydrochloric acid is secreted from gastric mucosa, studies on the mechanism of acid secretion have been actively progressed during the last 100 years. And, since Belladonna was used as the first antiulcer drug, anticholinergic drugs had been mainly used, and, in 1920, it was found out that gastric acid secretion is stimulated by histamine. And, since the first histamine $H_2$-receptor antagonist Cimetidine (Tagamet®) that inhibits the activity of histamine, which is strong gastric acid secretion-related hormone, on $H_2$ receptor was developed in 1977, various drugs antagonizing the receptors of acid secretion stimulating materials, and histamine $H_2$-receptor antagonist drugs represented by Ranitidine (Zantac®) developed in 1981, Famotidine (Gaster®/Pepcid®) developed in 1985, and the like led the world antiulcer drug markets. And, since *Helicobacter pylori* was first isolated as gastritis and ulcer-causing bacteria in 1983, combination therapy of proton pump inhibitor or $H_2$ antagonist and chemotherapeutic agent has been developed for eradication thereof.

Recently, there is an increasing demand for drugs having reversible inhibition mechanism among proton pump inhibitors, and the studies thereon are being actively progressed by global pharmaceutical companies. In order to distinguish from the existing PPI drug represented by Omeprazole, reversible proton pump inhibitors are named as potassium competitive acid blocker (P-CAB) or acid pump antagonist (APA).

Meanwhile, the process of ° secretion on the stomach wall had not been found out for a long time. However, recently, it was found out that $H^+/K^+$-ATPase in the microsomal fraction of stomach wall cells acts on the H+ secretion in gastro-intestinal tract to change $H^+$ and $K^+$, and the $H^+/K^+$-ATPase was named as a "proton pump". In the body, $H^+/K^+$-ATPase secretes $H^+$ that is produced by converting energy obtained by decomposition of ATP abundant in mitochondria into $H_2O$ into the gastric cavity. At this time, the conversion of $K^+$ and $H^+$ is conducted at a ratio of 1:1, and the existence of $H^+/K^+$-ATPase was confirmed in many animals secreting $H^+$ including human being.

Namely, in the receptors existing on the cell membrane of stomach wall cells, various acid secretion-stimulating material (histamine, acetylcholine, gastrin) bind to cause a series of gastric acid secretion reactions, and in the final process of the reactions, $H^+/K^+$-ATPase referred to as a proton pump that discharges $H^+$ and absorbs $K^+$ in the stomach wall cells acts. A compound inhibiting the proton pump to inhibit gastric acid secretion does not have anticholinergic activity or $H_2$ receptor antagonism, is absorbed as an inactive pro-drug when absorbed in the body, and is intensively distributed and activated in the secretory tubules of the parietal cells in gastric mucosa, which are the only acid compartment in a human body, and then, blocks the proton pump, which is the final step of gastric acid production, thereby inhibiting gastric acid secretion by a unique and selective mode of activity.

Representative drugs developed to regulate the proton pump include Omeprazole, Lansoprazole, Pantoprazole, Esomeprazole, and the like, and since the inhibitory activity of these drugs on gastric acid secretion are more potent and continuous than the conventional drugs, they are currently widely used as a therapeutic agent of peptic ulcer. And, since omeprazole based compounds strongly inhibit gastric acid secretion and simultaneously have gastric mucosa protection effect (cytoprotective activity), they exhibit characteristics of two activities (i.e., offense type and defense type, more strongly inhibit acid secretion in the day time as well as at night than $H_2$ receptor antagonist, and are known to have low recurrence rate.

However, a possibility that a proton pump inhibitor having irreversible activity mechanism may cause inhibition state of gastric acid secretion in the stomach for a long time to form tumor cells due to bacteria growth in the stomach, promotion of expression of proton pump, and increase in gastrin concentration is being suggested, and thus, development of material capable of inhibiting gastric acid secretion for a certain period only when the drug is administered through the development of reversible proton pump inhibitor is on the rise as research project. Revaprazan (Revanex®) of Yuhan Corporation, marketed on January, 2007 is the only drug, and the research and development of antiulcer drugs by worldwide leading pharmaceutical companies are directed towards reversible proton pump inhibitors, and in the future, appearance of new drugs is being anticipated.

As the representative examples of reversible proton pump inhibitors, a pyrrole derivatives are described in WO2007/026916 (Takeda Pharmaceutical Co. Ltd.), pyrrolo[2,3-c] pyridine derivative are described in WO2006/025716 (Yuhan Corp.), and benzimidazole derivatives are described in WO2007/072146 (Pfizer Inc., Japan; Raqualia Pharma Inc.).

SUMMARY OF THE INVENTION

Technical Problem

The inventors, during the studies on novel compounds having proton pump inhibition effects, confirmed that tetrahydrocyclopentapyrrole derivatives have proton pump inhibition effects, and thus, may be used for preventing or treating peptic ulcer, gastritis or reflux esophagitis, and completed the invention.

Technical Solution

It is an object of the invention to provide tetrahydrocyclopentapyrrole derivatives that can be used for preventing or treating peptic ulcer, gastritis or reflux esophagitis, or a pharmaceutically acceptable salt thereof, and a method for preparing the same.

It is another object of the invention to provide an intermediate that can be used for preparing the tetrahydrocyclopentapyrrole derivatives according to the present invention.

It is yet another object of the invention to provide a pharmaceutical composition containing the tetrahydrocyclopentapyrrole derivatives, or a pharmaceutically acceptable salt thereof according to the present invention.

It is yet another object of the invention to provide a pharmaceutical composition for preventing or treating peptic ulcer, gastritis or reflux esophagitis, containing the tetrahydrocyclopentapyrrole derivatives, or a pharmaceutically acceptable salt thereof according to the present invention as an active ingredient.

It is yet another object of the invention to provide a method for treating or preventing peptic ulcer, gastritis or reflux esophagitis, comprising administering an effective amount of the tetrahydrocyclopentapyrrole derivatives, or a pharmaceutically acceptable salt thereof according to the present invention to a subject having or suspected to have peptic ulcer, gastritis or reflux esophagitis.

Advantageous Effects

The compound represented by the Chemical Formula 1 according to the present invention exhibits reversible proton pump inhibition effect, and thus, may be used as APA for preventing or treating peptic ulcer, gastritis or reflux esophagitis.

DETAILED DESCRIPTION OF THE EMBODIMENTS

In order to achieve the objects, the present invention provides a compound represented by the following Chemical Formula 1, or a pharmaceutically acceptable salt thereof:

[Chemical Formula 1]

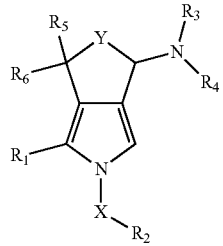

in the Chemical Formula 1,

X is —$CH_2$—, —CO—, or —$SO_2$—,

Y is $C_{1-3}$ alkylene, or —NH—, $R_1$ is $C_{1-4}$ alkyl, benzodioxolyl, benzofuranyl, benzyl, furanyl, phenyl, pyrazolyl, pyridinyl, pyrimidinyl, or thienyl, wherein, $R_1$ is unsubstituted; or substituted with one to three substituents respectively selected from the group consisting of $C_{1-4}$ alkyl, $C_{1-4}$ haloalkyl, $C_{1-4}$ alkoxy, $C_{1-4}$ haloalkoxy, $C_{3-6}$ cycloalkenyl, hydroxy, halogen, cyano, —COO($C_{1-4}$ alkyl), morpholino, phenyl and pyrrolidinyl $R_2$ is imidazolyl, phenyl, pyridinyl, thienyl, or pyridinyl fused with a 5-membered heteroaromatic ring having one or two heteroatoms selected from the group consisting of nitrogen and oxygen, wherein, $R_2$ is unsubstituted; or substituted with one to three substituents respectively selected from the group consisting of $C_{1-4}$ alkyl, $C_{1-4}$ haloalkyl, $C_{1-4}$ alkoxy, $C_{1-4}$ haloalkoxy, halogen, cyano, phenyl, phenoxy, N($C_{1-4}$ alkyl)$_2$ and —CO-morpholino, $R_3$ is hydrogen, or $C_{1-4}$ alkyl, $R_4$ is $C_{1-4}$ alkyl,

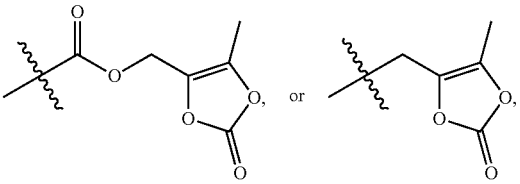

$R_5$ is hydrogen, or $C_{1-4}$ alkyl, and $R_6$ is hydrogen, or $C_{1-4}$ alkyl.

Preferably, X is —$SO_2$—.

Preferably, X is —$SO_2$—, and Y is $C_1$-3 alkylene.

Preferably, $R_1$ is unsubstituted; or substituted with one to three substituents respectively selected from the group consisting of methyl, trifluoromethyl, methoxy, trifluoromethoxy, cyclopentenyl, hydroxy, F, Cl, cyano, —COO($CH_3$), morpholino, phenyl and pyrrolidinyl.

Preferably, $R_2$ is unsubstituted; or substituted with one to three substituents respectively selected from the group consisting of methyl, trifluoromethyl, methoxy, trifluoromethoxy, difluoromethoxy, F, Cl, cyano, phenyl, phenoxy, dimethylamino and —CO-morpholino.

Preferably, $R_1$ is phenyl, and the phenyl is unsubstituted; or substituted with one to three substituents respectively selected from the group consisting of $C_{1-4}$ alkyl, $C_{1-4}$ haloalkyl, $C_{1-4}$ alkoxy, $C_{1-4}$ haloalkoxy, $C_{3-6}$ cycloalkenyl, hydroxy, halogen, cyano, —COO($C_{1-4}$ alkyl), morpholino and phenyl.

Preferably, $R_1$ is pyridinyl, and the pyridinyl is unsubstituted; or substituted with one substituent selected from the group consisting of $C_{1-4}$ haloalkyl, halogen, morpholino and pyrrolidinyl.

Preferably, $R_1$ is furanyl or pyrazolyl, and the furanyl or pyrazolyl is unsubstituted; or substituted with $C_{1-4}$ alkyl.

Preferably, $R_1$ is thienyl, and the thienyl is unsubstituted; or substituted with one or two $C_{1-4}$ alkyl.

Preferably, $R_1$ is benzodioxolyl, benzofuranyl, benzyl or pyrimidinyl, and the benzodioxolyl, benzofuranyl, benzyl or pyrimidinyl is unsubstituted.

Preferably, $R_2$ is imidazolyl, phenyl, pyridinyl, thienyl, isoxazole[5,4-b]pyridinyl, or pyrazolo[3,4-b]pyridinyl, and the $R_2$ is unsubstituted; or substituted with one to three substituents respectively selected from the group consisting of $C_{1-4}$ alkyl, $C_{1-4}$ haloalkyl, $C_{1-4}$ alkoxy, $C_{1-4}$ haloalkoxy, halogen, cyano, phenyl, phenoxy, N($C_{1-4}$ alkyl)$_2$ and —CO-morpholino.

Preferably, $R_2$ is phenyl, and the phenyl is unsubstituted; or substituted with one to three substituents respectively selected from the group consisting of $C_{1-4}$ alkyl, $C_{1-4}$ haloalkyl, $C_{1-4}$ alkoxy, $C_{1-4}$ haloalkoxy, halogen, cyano, phenyl, N($C_{1-4}$ alkyl)$_2$ and —CO-morpholino.

Preferably, $R_2$ is pyridinyl, and the pyridinyl is unsubstituted; or substituted with one or two substituents respectively selected from the group consisting of $C_{1-4}$ alkyl, $C_{1-4}$ alkoxy, halogen and phenoxy.

Preferably, $R_2$ is imidazolyl or isoxazole[5,4-b]pyridinyl, and the imidazolyl or isoxazole[5,4-b]pyridinyl is unsubstituted; or substituted with $C_{1-4}$ alkyl.

Preferably, $R_2$ is pyrazolo[3,4-b]pyridinyl, and the pyrazolo[3,4-b]pyridinyl is unsubstituted; or substituted with one or two $C_{1-4}$ alkyl.

Preferably, $R_2$ is thienyl, and the thienyl is unsubstituted.

Preferably, $R_3$ is hydrogen, and $R_4$ is $C_{1-4}$ alkyl.

Preferably, $R_5$ and $R_6$ are hydrogen, or $R_5$ and $R_6$ are methyl.

Preferably, X is —SO$_2$—, Y is $C_{1-3}$ alkylene, and $R_1$ and/or $R_2$ is phenyl.

Preferably, X is —SO$_2$—, Y is —CH$_2$—, and $R_1$ and $R_2$ are phenyl.

Preferably, X is —SO$_2$—, Y is —CH$_2$—, $R_1$ and $R_2$ are phenyl, furanyl, or thienyl, and $R_2$ is phenyl or pyridinyl.

Preferably, X is —SO$_2$—, Y is —CH$_2$—, $R_1$ is phenyl, furanyl, or thienyl, which is unsubstituted or substituted with one to three substituents selected from the group consisting of $C_{1-4}$ alkyl, $C_{1-4}$ haloalkyl, $C_{1-4}$ alkoxy, $C_{1-4}$ haloalkoxy, hydroxy, and halogen, and $R_2$ is phenyl or pyridinyl, which is unsubstituted or substituted with one to three substituents selected from the group consisting of $C_{1-4}$ alkyl, $C_{1-4}$ alkoxy, $C_{1-4}$ haloalkoxy, and halogen.

Preferably, X is —SO$_2$—, Y is —CH$_2$—, $R_1$ is phenyl, furanyl, or thienyl, which is unsubstituted or substituted with one or two substituents selected from the group consisting of $C_{1-4}$ alkyl, hydroxy, and halogen, and $R_2$ is phenyl or pyridinyl, which is unsubstituted or substituted with one or two substituents selected from the group consisting of $C_{1-4}$ alkyl, $C_{1-4}$ alkoxy, $C_{1-4}$ haloalkoxy, and halogen.

Preferably, X is —SO$_2$—, Y is —CH$_2$—, $R_1$ is thienyl unsubstituted or substituted with one or two $C_{1-4}$ alkyl, and $R_2$ is phenyl or pyridinyl unsubstituted or substituted with one or two halogen.

Representative examples of the compound represented by the Chemical Formula 1 are as follows:

1) 2-((3-chlorophenyl)sulfonyl-1-(2-fluorophenyl)-N-methyl-2,4,5,6-tetrahydrocyclopenta[c]pyrrol-4-amine,
2) 2-((3-chlorophenyl)sulfonyl)-N,1-dimethyl-2,4,5,6-tetrahydrocyclopenta[c]pyrrol-4-amine,
3) 2-((3-chlorophenyl)sulfonyl)-N-methyl-1-phenyl-2,4,5,6-tetrahydrocyclopenta[c]pyrrol-4-amine,
4) 2-((3-chlorophenyl)sulfonyl)-N-methyl-1-(o-tolyl)-2,4,5,6-tetrahydrocyclopenta[c]pyrrol-4-amine,
5) 1-(2-chlorophenyl)-2-((3-chlorophenyl)sulfonyl)-N-methyl-2,4,5,6-tetrahydrocyclopenta[c]pyrrol-4-amine,
6) 2-((3-chlorophenyl)sulfonyl)-1-(2-(cyclopent-3-en-1-yl)phenyl)-N-methyl-2,4,5,6-tetrahydrocyclopenta[c]pyrrol-4-amine,
7) 2-((3-chlorophenyl)sulfonyl)-N-methyl-1-(2-(morpholinophenyl)-2,4,5,6-tetrahydrocyclopenta[c]pyrrol-4-amine,
8) 2-((3-chlorophenyl)sulfonyl)-N-methyl-1-(m-tolyl)-2,4,5,6-tetrahydrocyclopenta[c]pyrrol-4-amine,
9) 2-((3-chlorophenyl)sulfonyl)-1-(3-fluorophenyl)-N-methyl-2,4,5,6-tetrahydrocyclopenta[c]pyrrol-4-amine,
10) 2-((3-chlorophenyl)sulfonyl)-N-methyl-1-(3-(trifluoromethyl)phenyl)-2,4,5,6-tetrahydrocyclopenta[c]pyrrol-4-amine,
11) 2-((3-chlorophenyl)sulfonyl)-1-(4-fluorophenyl)-N-methyl-2,4,5,6-tetrahydrocyclopenta[c]pyrrol-4-amine,
12) 4-(2-((3-chlorophenyl)sulfonyl)-4-(methylamino)-2,4,5,6-tetrahydrocyclopenta[c]pyrrol-1-yl)phenol,
13) 4-(2-((3-chlorophenyl)sulfonyl)-4-(methylamino)-2,4,5,6-tetrahydrocyclopenta[c]pyrrol-1-yl)benzonitrile,
14) 2-((3-chlorophenyl)sulfonyl)-1-(4-methoxyphenyl)-N-methyl-2,4,5,6-tetrahydrocyclopenta[c]pyrrol-4-amine,
15) methyl 4-(2-((3-chlorophenyl)sulfonyl)-4-(methylamino)-2,4,5,6-tetrahydrocyclopenta[c]pyrrol-1-yl)benzoate,
16) 2-((3-chlorophenyl)sulfonyl)-N-methyl-1-(4-(trifluoromethyl)phenyl)-2,4,5,6-tetrahydrocyclopenta[c]pyrrol-4-amine,
17) 2-((3-chlorophenyl)sulfonyl)-N-methyl-1-(4-(trifluoromethoxy)phenyl)-2,4,5,6-tetrahydrocyclopenta[c]pyrrol-4-amine,
18) 2-((3-chlorophenyl)sulfonyl)-1-(2-fluoro-4-methylphenyl)-N-methyl-2,4,5,6-tetrahydrocyclopenta[c]pyrrol-4-amine,
19) 2-((3-chlorophenyl)sulfonyl)-1-(2,4-difluorophenyl)-N-methyl-2,4,5,6-tetrahydrocyclopenta[c]pyrrol-4-amine,
20) 1-(4-chloro-2-fluorophenyl)-2-((3-chlorophenyl)sulfonyl)-N-methyl-2,4,5,6-tetrahydrocyclopenta[c]pyrrol-4-amine,
21) 2-((3-chlorophenyl)sulfonyl)-1-(2,4-dichlorophenyl)-N-methyl-2,4,5,6-tetrahydrocyclopenta[c]pyrrol-4-amine,
22) 1-(5-chloro-2-fluorophenyl)-2-((3-chlorophenyl)sulfonyl)-N-methyl-2,4,5,6-tetrahydrocyclopenta[c]pyrrol-4-amine,
23) 2-((3-chlorophenyl)sulfonyl)-1-(2,5-dichlorophenyl)-N-methyl-2,4,5,6-tetrahydrocyclopenta[c]pyrrol-4-amine,
24) 2-((3-chlorophenyl)sulfonyl)-1-(3,4-difluorophenyl)-N-methyl-2,4,5,6-tetrahydrocyclopenta[c]pyrrol-4-amine,
25) 2-((3-chlorophenyl)sulfonyl)-1-(3,5-dichlorophenyl)-N-methyl-2,4,5,6-tetrahydrocyclopenta[c]pyrrol-4-amine,
26) 1-(5-chloro-2-fluoro-4-methylphenyl)-2-((3-chlorophenyl)sulfonyl)-N-methyl-2,4,5,6-tetrahydrocyclopenta[c]pyrrol-4-amine,
27) 1-benzyl-2-((3-chlorophenyl)sulfonyl)-N-methyl-2,4,5,6-tetrahydrocyclopenta[c]pyrrol-4-amine,
28) 1-(benzo[d][1,3]dioxol-5-yl)-2-((3-chlorophenyl)sulfonyl)-N-methyl-2,4,5,6-tetrahydrocyclopenta[c]pyrrol-4-amine,
29) 1-(benzofuran-5-yl)-2-((3-chlorophenyl)sulfonyl)-N-methyl-2,4,5,6-tetrahydrocyclopenta[c]pyrrol-4-amine,
30) 2-((3-chlorophenyl)sulfonyl)-N-methyl-1-(1-methyl-1H-pyrazol-4-yl)-2,4,5,6-tetrahydrocyclopenta[c]pyrrol-4-amine,
31) 2-((3-chlorophenyl)sulfonyl)-1-(furan-3-yl)-N-methyl-2,4,5,6-tetrahydrocyclopenta[c]pyrrol-4-amine,
32) 2-((3-chlorophenyl)sulfonyl)-N-methyl-1-(5-methylfuran-2-yl)-2,4,5,6-tetrahydrocyclopenta[c]pyrrol-4-amine,
33) 2-((3-chlorophenyl)sulfonyl)-N-methyl-1-(thiophen-3-yl)-2,4,5,6-tetrahydrocyclopenta[c]pyrrol-4-amine,
34) 2-((3-chlorophenyl)sulfonyl)-N-methyl-1-(4-methylthiophen-3-yl)-2,4,5,6-tetrahydrocyclopenta[c]pyrrol-4-amine,
35) 2-((3-chlorophenyl)sulfonyl)-1-(2,5-dimethylthiophen-3-yl)-N-methyl-2,4,5,6-tetrahydrocyclopenta[c]pyrrol-4-amine,
36) 2-((3-chlorophenyl)sulfonyl)-1-(6-chloropyridin-2-yl)-N-methyl-2,4,5,6-tetrahydrocyclopenta[c]pyrrol-4-amine,
37) 2-((3-chlorophenyl)sulfonyl)-N-methyl-1-(pyridin-3-yl)-2,4,5,6-tetrahydrocyclopenta[c]pyrrol-4-amine,
38) 2-((3-chlorophenyl)sulfonyl)-N-methyl-1-(2-trifluoromethyl)pyridin-3-yl)-2,4,5,6-tetrahydrocyclopenta[c]pyrrol-4-amine,
39) 2-((3-chlorophenyl)sulfonyl)-N-methyl-1-(6-trifluoromethyl)pyridin-3-yl)-2,4,5,6-tetrahydrocyclopenta[c]pyrrol-4-amine,
40) 2-((3-chlorophenyl)sulfonyl)-N-methyl-1-(6-pyrrolidin-1-yl)pyridin-3-yl)-2,4,5,6-tetrahydrocyclopenta[c]pyrrol-4-amine,
41) 2-((3-chlorophenyl)sulfonyl)-N-methyl-1-(6-morpholinopyridin-3-yl)-2,4,5,6-tetrahydrocyclopenta[c]pyrrol-4-amine,
42) 2-((3-chlorophenyl)sulfonyl)-N-methyl-1-(pyridin-4-yl)-2,4,5,6-tetrahydrocyclopenta[c]pyrrol-4-amine, 43) 1-(2-fluorophenyl)-N-methyl-2-(phenylsulfonyl)-2,4,5,6-tetrahydrocyclopenta[c]pyrrol-4-amine,
44) 1-(2-fluoro-4-methylphenyl)-N-methyl-2-(phenylsulfonyl)-2,4,5,6-tetrahydrocyclopenta[c]pyrrol-4-amine,
45) 1-(2,5-dichlorophenyl)-N-methyl-2-(phenylsulfonyl)-2,4,5,6-tetrahydrocyclopenta[c]pyrrol-4-amine,
46) 1-(2-fluorophenyl)-2-((2-methoxyphenyl)sulfonyl)-N-methyl-2,4,5,6-tetrahydrocyclopenta[c]pyrrol-4-amine,
47) 1-(2-fluoro-4-methylphenyl)-2-((3-fluorophenyl)sulfonyl)-N-methyl-2,4,5,6-tetrahydrocyclopenta[c]pyrrol-4-amine,
48) 2-((2-chlorophenyl)sulfonyl)-1-(2-fluoro-4-methylphenyl)-N-methyl-2,4,5,6-tetrahydrocyclopenta[c]pyrrol-4-amine,
49) 2-((2-chlorophenyl)sulfonyl)-1-(4-fluoro-2-methylphenyl)-N-methyl-2,4,5,6-tetrahydrocyclopenta[c]pyrrol-4-amine,
50) 2-((2-chlorophenyl)sulfonyl)-1-(2,5-dichlorophenyl)-N-methyl-2,4,5,6-tetrahydrocyclopenta[c]pyrrol-4-amine,
51) 1-(2,5-dichlorophenyl)-2-((3-fluorophenyl)sulfonyl)-N-methyl-2,4,5,6-tetrahydrocyclopenta[c]pyrrol-4-amine,
52) 1-(2-fluoro-4-methylphenyl)-N-methyl-2-(m-tolylsulfonyl)-2,4,5,6-tetrahydrocyclopenta[c]pyrrol-4-amine,
53) 1-(2,5-dichlorophenyl)-N-methyl-2-(m-tolylsulfonyl)-2,4,5,6-tetrahydrocyclopenta[c]pyrrol-4-amine,
54) 1-(2-fluoro-4-methylphenyl)-2-((3-methoxyphenyl)sulfonyl)-N-methyl-2,4,5,6-tetrahydrocyclopenta[c]pyrrol-4-amine,
55) 1-(2,5-dichlorophenyl)-2-((3-methoxyphenyl)sulfonyl)-N-methyl-2,4,5,6-tetrahydrocyclopenta[c]pyrrol-4-amine,
56) 2-((3-(dimethylamino)phenyl)sulfonyl)-1-(2-fluorophenyl)-N-methyl-2,4,5,6-tetrahydrocyclopenta[c]pyrrol-4-amine,
57) 2-((3-(difluoromethoxy)phenyl)sulfonyl)-1-(2-fluorophenyl)-N-methyl-2,4,5,6-tetrahydrocyclopenta[c]pyrrol-4-amine,
58) (3-((1-(2-fluorophenyl)-4-(methylamino)-5,6-dihydrocyclopenta[c]pyrrol-2(4H)-yl)sulfonyl)phenyl)(morpholino)methanone,
59) 1-(2-fluorophenyl)-N-methyl-2-tosyl-2,4,5,6-tetrahydrocyclopenta[c]pyrrol-4-amine,
60) 1-(2-fluoro-4-methylphenyl)-2-((4-fluorophenyl)sulfonyl)-N-methyl-2,4,5,6-tetrahydrocyclopenta[c]pyrrol-4-amine,
61) 1-(2,5-dichlorophenyl)-2-((4-fluorophenyl)sulfonyl)-N-methyl-2,4,5,6-tetrahydrocyclopenta[c]pyrrol-4-amine,
62) 2-([1,1'-biphenyl]-4-ylsulfonyl)-1-(2-fluorophenyl)-N-methyl-2,4,5,6-tetrahydrocyclopenta[c]pyrrol-4-amine,
63) 2-((3-chloro-2-methylphenyl)sulfonyl)-1-(2-fluorophenyl)-N-methyl-2,4,5,6-tetrahydrocyclopenta[c]pyrrol-4-amine,
64) 2-((2,3-dichlorophenyl)sulfonyl)-1-(2-fluorophenyl)-N-methyl-2,4,5,6-tetrahydrocyclopenta[c]pyrrol-4-amine,
65) 2-((2,4-difluorophenyl)sulfonyl)-1-(2-fluorophenyl)-N-methyl-2,4,5,6-tetrahydrocyclopenta[c]pyrrol-4-amine,
66) 2-((2-chloro-4-fluorophenyl)sulfonyl)-1-(2-fluorophenyl)-N-methyl-2,4,5,6-tetrahydrocyclopenta[c]pyrrol-4-amine,
67) 3-chloro-4-((1-(2-fluorophenyl)-4-(methylamino)-5,6-dihydrocyclopenta[c]pyrrol-2(4H)-yl)sulfonyl)benzonitrile,
68) 2-((2-chloro-4-(trifluoromethoxy)phenyl)sulfonyl)-1-(2-fluorophenyl)-N-methyl-2,4,5,6-tetrahydrocyclopenta[c]pyrrol-4-amine,
69) 2-((2-chloro-4-(trifluoromethyl)phenyl)sulfonyl)-1-(2-fluorophenyl)-N-methyl-2,4,5,6-tetrahydrocyclopenta[c]pyrrol-4-amine,
70) 2-((2,5-dichlorophenyl)sulfonyl)-1-(2-fluorophenyl)-N-methyl-2,4,5,6-tetrahydrocyclopenta[c]pyrrol-4-amine,
71) 2-((2,5-dichlorophenyl)sulfonyl)-1-(2,4-difluorophenyl)-N-methyl-2,4,5,6-tetrahydrocyclopenta[c]pyrrol-4-amine,
72) 2-((2,5-dichlorophenyl)sulfonyl)-1-(2-fluoro-4-methylphenyl)-N-methyl-2,4,5,6-tetrahydrocyclopenta[c]pyrrol-4-amine,
73) 1-(2,5-dichlorophenyl)-2-((2,5-dichlorophenyl)sulfonyl)-N-methyl-2,4,5,6-tetrahydrocyclopenta[c]pyrrol-4-amine,
74) 2-((2-chloro-5-(trifluoromethyl)phenyl)sulfonyl)-1-(2-fluorophenyl)-N-methyl-2,4,5,6-tetrahydrocyclopenta[c]pyrrol-4-amine,
75) 2-((2,6-dichlorophenyl)sulfonyl)-1-(2-fluorophenyl)-N-methyl-2,4,5,6-tetrahydrocyclopenta[c]pyrrol-4-amine,
76) 2-((3,4-dichlorophenyl)sulfonyl)-1-(2-fluorophenyl)-N-methyl-2,4,5,6-tetrahydrocyclopenta[c]pyrrol-4-amine,
77) 2-((3,5-dichlorophenyl)sulfonyl)-1-(2-fluorophenyl)-N-methyl-2,4,5,6-tetrahydrocyclopenta[c]pyrrol-4-amine,
78) 2-((3,5-dichlorophenyl)sulfonyl)-1-(2-fluoro-4-methylphenyl)-N-methyl-2,4,5,6-tetrahydrocyclopenta[c]pyrrol-4-amine,
79) 1-(2,5-dichlorophenyl)-2-((3,5-dichlorophenyl)sulfonyl)-N-methyl-2,4,5,6-tetrahydrocyclopenta[c]pyrrol-4-amine,
80) 1-(2-fluorophenyl)-N-methyl-2-((2,3,4-trichlorophenyl)sulfonyl)-2,4,5,6-tetrahydrocyclopenta[c]pyrrol-4-amine,
81) N-methyl-1-phenyl-2-((2,4,5-trichlorophenyl)sulfonyl)-2,4,5,6-tetrahydrocyclopenta[c]pyrrol-4-amine,
82) 1-(2-fluoro-4-methylphenyl)-N-methyl-2-((2,4,5-trichlorophenyl)sulfonyl)-2,4,5,6-tetrahydrocyclopenta[c]pyrrol-4-amine,
83) 1-(2,5-dichlorophenyl)-N-methyl-2-((2,4,5-trichlorophenyl)sulfonyl)-2,4,5,6-tetrahydrocyclopenta[c]pyrrol-4-amine,
84) 1-(2-fluorophenyl)-N-methyl-2-((2,4,5-trichlorophenyl)sulfonyl)-2,4,5,6-tetrahydrocyclopenta[c]pyrrol-4-amine,
85) 1-(2-fluorophenyl)-N-methyl-2-((2,4,6-trichlorophenyl)sulfonyl)-2,4,5,6-tetrahydrocyclopenta[c]pyrrol-4-amine,
86) 2-((2,6-dichloro-4-(trifluoromethyl)phenyl)sulfonyl)-1-(2-fluorophenyl)-N-methyl-2,4,5,6-tetrahydrocyclopenta[c]pyrrol-4-amine,
87) 1-(2-fluorophenyl)-N-methyl-2-(thiophen-2-ylsulfonyl)-2,4,5,6-tetrahydrocyclopenta[c]pyrrol-4-amine,
88) 1-(2-fluorophenyl)-N-methyl-2-(pyridin-3-ylsulfonyl)-2,4,5,6-tetrahydrocyclopenta[c]pyrrol-4-amine,
89) 1-(2-chlorophenyl)-N-methyl-2-(pyridin-3-ylsulfonyl)-2,4,5,6-tetrahydrocyclopenta[c]pyrrol-4-amine,
90) 1-(2-fluoro-4-methylphenyl)-N-methyl-2-(pyridin-3-ylsulfonyl)-2,4,5,6-tetrahydrocyclopenta[c]pyrrol-4-amine,
91) 1-(4-chloro-2-fluorophenyl)-N-methyl-2-(pyridin-3-ylsulfonyl)-2,4,5,6-tetrahydrocyclopenta[c]pyrrol-4-amine,
92) 1-(2,5-dichlorophenyl)-N-methyl-2-(pyridin-3-ylsulfonyl)-2,4,5,6-tetrahydrocyclopenta[c]pyrrol-4-amine,
93) 1-(5-chloro-2-fluoro-3-methylphenyl)-N-methyl-2-(pyridin-3-ylsulfonyl)-2,4,5,6-tetrahydrocyclopenta[c]pyrrol-4-amine,
94) N-methyl-2-(pyridin-3-ylsulfonyl)-1-(thiophen-3-yl)-2,4,5,6-tetrahydrocyclopenta[c]pyrrol-4-amine,
95) 2-((5-chloropyridin-3-yl)sulfonyl)-1-(2-fluorophenyl)-N-methyl-2,4,5,6-tetrahydrocyclopenta[c]pyrrol-4-amine, 96) 1-(2-fluorophenyl)-N-methyl-2-((6-phenoxypyridin-3-yl)sulfonyl)-2,4,5,6-tetrahydrocyclopenta[c]pyrrol-4-amine,
97) 1-(2-fluorophenyl)-N-methyl-2-((3-methylisoxazolo[5,4-b]pyridin-5-yl)sulfonyl-)2,4,5,6-tetrahydrocyclopenta[c]pyrrol-4-amine,
98) 2-((2-chloro-6-methoxypyridin-3-yl)sulfonyl)-1-(2-fluorophenyl)-N-methyl-2,4,5,6-tetrahydrocyclopenta[c]pyrrol-4-amine,
99) 2-((2-chloro-6-methylpyridin-3-yl)sulfonyl)-1-(2-fluorophenyl)-N-methyl-2,4,5,6-tetrahydrocyclopenta[c]pyrrol-4-amine,
100) 2-((2-chloro-5-methylpyridin-3-yl)sulfonyl)-1-(2-fluorophenyl)-N-methyl-2,4,5,6-tetrahydrocyclopenta[c]pyrrol-4-amine,
101) 1-(2-fluorophenyl)-N-methyl-2-((1-methyl-1H-imidazol-2-yl)sulfonyl)-2,4,5,6-tetrahydrocyclopenta[c]pyrrol-4-amine,
102) 2-((1,3-dimethyl-1H-pyrazolo[3,4-b]pyridin-5-yl)sulfonyl)-1-(2-fluorophenyl)-N-methyl-2,4,5,6-tetrahydrocyclopenta[c]pyrrol-4-amine,
103) N-ethyl-1-(2-fluorophenyl)-2-(pyridin-3-ylsulfonyl)-2,4,5,6-tetrahydrocyclopenta[c]pyrrol-4-amine,
104) 1-(2-fluorophenyl)-N-isopropyl-2-(pyridin-3-ylsulfonyl)-2,4,5,6-tetrahydrocyclopenta[c]pyrrol-4-amine,
105) 1-(2-fluorophenyl)-N,6,6-trimethyl-2-(pyridin-3-ylsulfonyl)-2,4,5,6-tetrahydrocyclopenta[c]pyrrol-4-amine,
106) 2-((3-chlorophenyl)sulfonyl)-1-(2-fluorophenyl)-N,6,6-trimethyl-2,4,5,6-tetrahydrocyclopenta[c]pyrrol-4-amine,
107) 2-(3-chlorobenzyl)-1-(2-fluorophenyl)-N-methyl-2,4,5,6-tetrahydrocyclopenta[c]pyrrol-4-amine,
108) 2-(3-fluorobenzyl)-1-(2-fluorophenyl)-N-methyl-2,4,5,6-tetrahydrocyclopenta[c]pyrrol-4-amine,
109) 2-benzyl-1-(2-fluorophenyl)-N-methyl-2,4,5,6-tetrahydrocyclopenta[c]pyrrol-4-amine,
110) 1-(2-fluorophenyl)-N-methyl-2-(3-methylbenzyl)-2,4,5,6-tetrahydrocyclopenta[c]pyrrol-4-amine,
111) 1-(2-fluorophenyl)-2-(3-methoxybenzyl)-N-methyl-2,4,5,6-tetrahydrocyclopenta[c]pyrrol-4-amine,
112) 2-(3-chlorobenzyl)-1-(2-fluorophenyl)-N-methyl-2,4,5,6-tetrahydrocyclopenta[c]pyrrol-4-amine,
113) 1-(2,4-difluorophenyl)-2-((3-fluorophenyl)sulfonyl)-N-methyl-2,4,5,6-tetrahydrocyclopenta[c]pyrrol-4-amine,
114) (3-chlorophenyl)(1-(2,4-difluorophenyl)-4-(methylamino)-5,6-dihydrocyclopenta[c]pyrrol-2(4H)-yl)methanone,
115) 5-((3-chlorophenyl)sulfonyl)-4-(2-fluorophenyl)-N-methyl-1,2,3,5-tetrahydropyrrolo[3,4-c]pyrrol-1-amine,
116) (5-methyl-2-oxo-1,3-dioxol-4-yl)methyl (1-(2,4-difluorophenyl)-2-((3-fluorophenyl)sulfonyl)-2,4,5,6-tetrahydrocyclopenta[c]pyrrol-4-yl)-N-methylformamide,
117) 4-(((1-(2,4-difluorophenyl)-2-((3-fluorophenyl)sulfonyl)-2,4,5,6-tetrahydrocyclopenta[c]pyrrol-4-yl)(methyl)amino)methyl)-5-methyl-1,3-dioxol-2-one,
118) (5-methyl-2-oxo-1,3-dioxol-4-yl)methyl (2-((3-chlorophenyl)sulfonyl)-1-(2-fluorophenyl)-2,4,5,6-tetrahydrocyclopenta[c]pyrrol-4-yl)-(methyl)carbamate,
119) 4-(((2-((3-chlorophenyl)sulfonyl)-1-(2-fluorophenyl)-2,4,5,6-tetrahydrocyclopenta[c]pyrrol-4-yl)(methyl)amino)methyl)-5-methyl-1,3-dioxol-2-one,
120) 1-(2-fluorophenyl)-2-((3-fluorophenyl)sulfonyl)-N-methyl-4,5,6,7-tetrahydro-2H-isoindole-4-amine,
121) 1-(2-fluorophenyl)-N-methyl-2-(m-tolylsulfonyl)-4,5,6,7-tetrahydro-2H-isoindole-4-amine,
122) 1-(2-fluorophenyl)-2-((3-methoxyphenyl)sulfonyl)-N-methyl-4,5,6,7-tetrahydro-2H-isoindole-4-amine,
123) 2-((3-(difluoromethoxy)phenyl)sulfonyl)-1-(2-fluorophenyl)-N-methyl-4,5,6,7-tetrahydro-2H-isoindole-4-amine,
124) 1-(2-fluorophenyl)-N-methyl-2-((3-(trifluoromethyl)phenyl)sulfonyl)-4,5,6,7-tetrahydro-2H-isoindole-4-amine,
125) 1-(2-fluorophenyl)-N-methyl-2-((3-(trifluoromethoxy)phenyl)sulfonyl)-4,5,6,7-tetrahydro-2H-isoindole-4-amine,
126) 2-((5-chloro-2-fluorophenyl)sulfonyl)-1-(2-fluorophenyl)-N-methyl-4,5,6,7-tetrahydro-2H-isoindole-4-amine,
127) 1-([1,1'-biphenyl]-4-yl)-2-((3-chlorophenyl)sulfonyl)-N-methyl-4,5,6,7-tetrahydro-2H-isoindole-4-amine,
128) 2-((3-chlorophenyl)sulfonyl)-N-methyl-1-(pyridin-4-yl)-4,5,6,7-tetrahydro-2H-isoindole-4-amine,
129) 2-((3-chlorophenyl)sulfonyl)-N-methyl-1-(pyrimidin-5-yl)-4,5,6,7-tetrahydro-2H-isoindole-4-amine,
130) 2-((3-(dimethylamino)phenyl)sulfonyl)-1-(2-fluorophenyl)-N-methyl-4,5,6,7-tetrahydro-2H-isoindole-4-amine,
131) 1-(2-fluorophenyl)-N-methyl-2-(pyridin-3-ylsulfonyl)-4,5,6,7-tetrahydro-2H-isoindole-4-amine,
132) N-methyl-2-(pyridin-3-ylsulfonyl)-1-(o-tolyl)-4,5,6,7-tetrahydro-2H-isoindole-4-amine,
133) 1-(2-chlorophenyl)-N-methyl-2-(pyridin-3-ylsulfonyl)-4,5,6,7-tetrahydro-2H-isoindole-4-amine,
134) 1-([1,1'-biphenyl]-4-yl)-N-methyl-2-(pyridin-3-ylsulfonyl)-4,5,6,7-tetrahydro-2H-isoindole-4-amine,
135) 1-(2,4-difluorophenyl)-N-methyl-2-(pyridin-3-ylsulfonyl)-4,5,6,7-tetrahydro-2H-isoindole-4-amine,
136) 1-(2-fluorophenyl)-2-((3-fluorophenyl)sulfonyl)-N,N-dimethyl-4,5,6,7-tetrahydro-2H-isoindole-4-amine,
137) 1-(2-fluorophenyl)-N,N-dimethyl-2-(m-tolylsulfonyl)-4,5,6,7-tetrahydro-2H-isoindole-4-amine,
138) 2-((3-chlorophenyl)sulfonyl)-1-(2-fluorophenyl)-N,N-dimethyl-4,5,6,7-tetrahydro-2H-isoindole-4-amine,
139) 1-(2-fluorophenyl)-N,N-dimethyl-2-((3-(trifluoromethyl)phenyl)sulfonyl)-4,5,6,7-tetrahydro-2H-isoindole-4-amine,
140) 1-(2-fluorophenyl)-2-((3-methoxyphenyl)sulfonyl)-N,N-dimethyl-4,5,6,7-tetrahydro-2H-isoindole-4-amine,
141) 1-(2-fluorophenyl)-N,N-dimethyl-2-((3-(trifluoromethoxy)phenyl)sulfonyl)-4,5,6,7-tetrahydro-2H-isoindole-4-amine,
142) 2-((3-(difluoromethoxy)phenyl)sulfonyl)-1-(2-fluorophenyl)-N,N-dimethyl-4,5,6,7-tetrahydro-2H-isoindole-4-amine,
143) 2-((3-(dimethylamino)phenyl)sulfonyl)-1-(2-fluorophenyl)-N,N-dimethyl-4,5,6,7-tetrahydro-2H-isoindole-4-amine,
144) 1-(2-fluorophenyl)-N,N-dimethyl-2-(pyridin-3-ylsulfonyl)-4,5,6,7-tetrahydro-2H-isoindole-4-amine,
145) 2-((3-chlorophenyl)sulfonyl)-1-(2-fluorophenyl)-N-methyl-2,4,5,6,7,8-hexahydrocyclohepta[c]pyrrol-4-amine,
146) 1-(2-fluorophenyl)-N-methyl-2-(pyridin-3-ylsulfonyl)-2,4,5,6,7,8-hexahydrocyclohepta[c]pyrrol-4-amine, and
147) 2-((3-chlorophenyl)sulfonyl)-N-ethyl-1-(2-fluorophenyl)-2,4,5,6,7,8-hexahydrocyclohepta[c]pyrrol-4-amine.

The compound of the Chemical Formula 1 may form a salt, particularly a pharmaceutically acceptable salt. The suitable pharmaceutically acceptable salts include those commonly used in the field to which the invention pertains, such as acid addition salt, and are not specifically limited (see [(J. Pharm. Sci., 66, 1(1977)]). Preferable pharmaceutically acceptable acid addition salts may include inorganic acid such as hydrochloric acid, hydrobromic acid, phosphoric acid, orthophosphoric acid or sulfuric acid; or organic acid such as methanesulfonic acid, benzenesulfonic acid, toluenesulfonic acid, acetic acid, propionic acid, lactic acid, citric acid, fumaric acid, malic acid, succinic acid, salicylic acid, maleic acid, glycerophosphoric acid or acetylsalicylic acid.

And, a pharmaceutically acceptable metal salt may be obtained using base by a common method. For example, a pharmaceutically acceptable metal salt may be obtained by dissolving the compound of the Chemical Formula 1 in an excessive amount of an alkali metal hydroxide or an alkali earth metal hydroxide solution, filtering non-dissolved compound salts, and then, evaporating and drying the filtrate. Wherein, it is preferable to prepare sodium salt, potassium salt or calcium salt as the metal salt, and these metal salts may be reacted with an appropriate salt (for example, nitrate salt).

And, the compound of the Chemical Formula 1 of the present invention includes solvates and hydrates that can be prepared therefrom, as well as pharmaceutically acceptable salts thereof, and it also includes all the possible stereoisomers. The solvates, hydrates and stereoisomers of the compound of Chemical Formula 1 may be prepared from the compound of the Chemical Formula 1 by common methods.

And, the compound of the Chemical Formula 1 of the present invention may be prepared in a crystalline form or a non-crystalline form, and in case the compound of the Chemical Formula 1 is prepared in a crystalline form, it may be optionally hydrated or solvated. The present invention may include compounds containing various amounts of water, as well as a stoichiometric hydrate of the compound of the Chemical Formula 1. A solvate of the compound of the Chemical Formula 1 of the present invention includes both stoichiometric solvate and non-stoichiometric solvate.

The present invention also provides a pharmaceutical composition containing the compound represented by the Chemical Formula 1, or a pharmaceutically acceptable salt thereof.

The present invention also provides a pharmaceutical composition for preventing or treating peptic ulcer, gastritis or reflux esophagitis, containing the compound represented by the Chemical Formula 1, or a pharmaceutically acceptable salt thereof as an active ingredient.

As used herein, the term "preventing" means all the activities of inhibiting or delaying peptic ulcer, gastritis or reflux esophagitis by the administration of the pharmaceutical composition containing the compound represented by the Chemical Formula 1, or a pharmaceutically acceptable salt thereof. And, the term "treating" means all the activities of improving the symptoms of or completely recovering peptic ulcer, gastritis or reflux esophagitis by the administration of the pharmaceutical composition containing the compound represented by the Chemical Formula 1, or a pharmaceutically acceptable salt thereof.

The compound of the Chemical Formula 1 of the present invention, or a pharmaceutically acceptable salt thereof has the effect of inhibiting proton pump ($H^+/K^+$-ATPase) activity (Experimental Example 1), and the effect of inhibiting basal gastric acid secretion in pylorus-ligated rats (Experimental Example 2), and thus, may be used for preventing or treating peptic ulcer, gastritis or reflux esophagitis.

The pharmaceutical composition of the present invention may be formulated in an oral administration form or a parenteral administration form according to standard pharmaceutical practice. The dosage forms may contain additives such as pharmaceutically acceptable carrier, adjuvant, or diluents, in addition to the active ingredient. The suitable carrier may include, for example, a saline solution, polyethyleneglycol, ethanol, vegetable oil and isopropyl myristate, and the like, the diluents may include, for example, lactose, dextrose, sucrose, mannitol, sorbitol, celluolose and/or glycine, and the like, but are not limited thereto. And, the compound of the present invention, or a pharmaceutically acceptable salt thereof may be dissolved in oil commonly used for preparing an injection solution, propyleneglycol or other solvents. And, for local action, the compound of the present invention, or a pharmaceutically acceptable salt thereof may be formulated in an ointment or cream.

Preferable administration amount of the compound of the present invention, or a pharmaceutically acceptable salt thereof is varied according to the condition and body weight of a patient, the severity of disease, the form of drug, administration route and period, but may be appropriately selected by a person of ordinary skill in the art. However, in order to achieve preferable effect, it is preferable to administer the compound of the present invention in an amount of 0.0001 to 100 mg/kg (body weight), preferably 0.001 to 100 mg/kg (body weight) per day. It may be administered orally or parenterally once a day or in divided doses. According to the administration method, the composition may contain 0.001 to 99 wt %, preferably 0.01 to 60 wt % of the compound of the present invention.

The pharmaceutical composition of the present invention may be administered to mammals including rat, mouse, domestic animals and human being through various routes. All modes of administration may be expected, and for example, it may be administered orally, rectally, or by intravenous, intramuscular, subcutaneous, intrauterine or intracerbroventricular injection.

The present invention also provides a method for treating or preventing peptic ulcer, gastritis or reflux esophagitis, comprising administering an effective amount of the compound represented by the Chemical Formula 1 of the present invention, or a pharmaceutically acceptable salt thereof to a subject having or suspected to have peptic ulcer, gastritis or reflux esophagitis.

The subject means all the animals including human being in which peptic ulcer, gastritis or reflux esophagitis occurred or may occur. The compound may be administered in the form of a pharmaceutical composition, and it may be administered orally or parenterally. And, the preferable administration amount of the compound of the present invention may be varied according to the condition and body weight of a subject, the severity of disease, the form of drug, administration route and period, and it may be appropriately selected by a person of ordinary skill in the art.

The present invention also provides a method for preparing the compound represented by the Chemical Formula 1. For example, in case Y in the Chemical Formula 1 is $C_{1-3}$ alkylene, the compound of the Chemical Formula 1 may be prepared as shown in the following Reaction Scheme 1.

[Reaction Scheme 1]

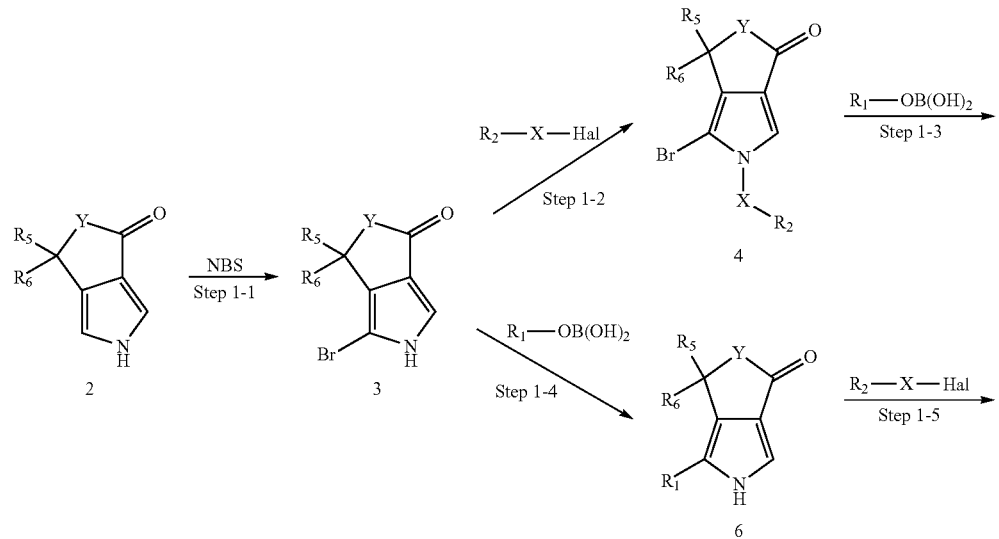

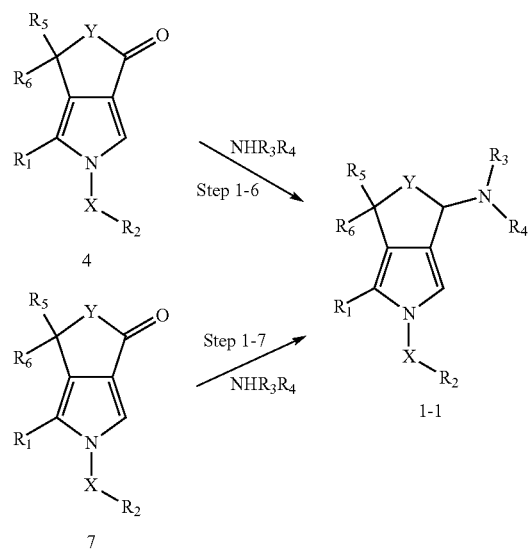

Hereinafter, the Reaction Scheme 1 will be explained in detail.

First, in the step 1-1, a compound represented by the Chemical Formula 2 is reacted with NBS (N-bromosuccinimide) to prepare a compound represented by the Chemical Formula 3. THF is preferably used as a solvent.

In the step 1-2, a compound represented by the Chemical Formula 3 is reacted with $R_2$—X-Hal (wherein, $R_2$ and X are as defined above in the Chemical Formula 1, Hal denotes halogen, preferably F, Br or Cl) to prepare a compound represented by the Chemical Formula 4. N,N-dimethylformamide is preferably used as a solvent.

In the step 1-3, a compound represented by the Chemical Formula 4 is reacted with $R_1$—OB(OH)$_2$ (wherein, $R_1$ is as defined above in the Chemical Formula 1) to prepare a compound represented by the Chemical Formula 5. 1,2-dimethoxyethane is preferably used as a solvent.

The step 1-4 and the step 1-5 are identical to the step 1-3 and 1-2 respectively, except that the sequence is changed. Namely, $R_2$ may be substituted and then $R_1$ may be substituted, or $R_1$ may be substituted and then $R_2$ may be substituted.

In the step 1-6 and the step 1-7, a compound represented by the Chemical Formula 5 or 7 are respectively reacted with NHR$_3$R$_4$ (wherein, $R_3$ and $R_4$ are as defined above in the Chemical Formula 1) to prepare a compound represented by the Chemical Formula 1-1. THF is preferably used as a solvent.

And, in case $R_4$ in the Chemical Formula 1 is

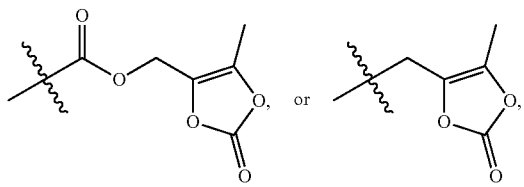

the compound of the Chemical Formula 1 may be also prepared as shown in the following Reaction scheme 2.

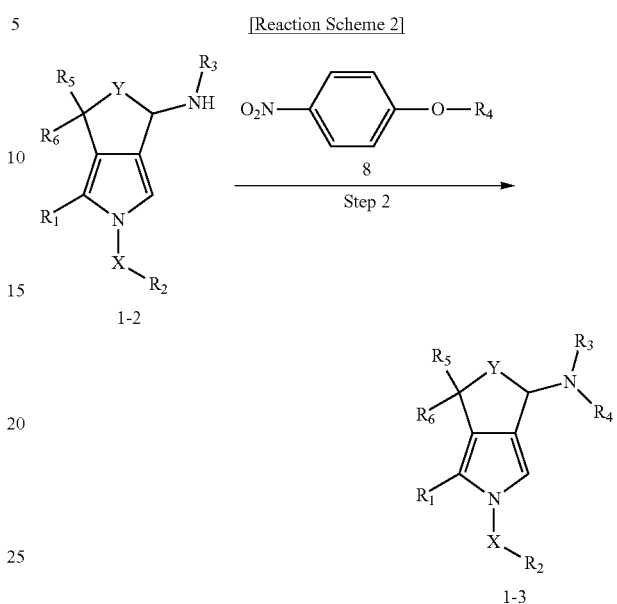

In the step 2, a compound represented by the Chemical Formula 1-2 is reacted with a compound represented by the Chemical Formula 8 to prepare a compound represented by the Chemical Formula 1-3. The compound represented by the Chemical Formula 1-2 may be prepared by the Reaction Scheme 1. N,N-dimethylformamide is preferably used as a solvent.

And, in case Y in the Chemical Formula 1 is —NH—, the Chemical Formula 1 may be also prepared as shown in the following Reaction scheme 3.

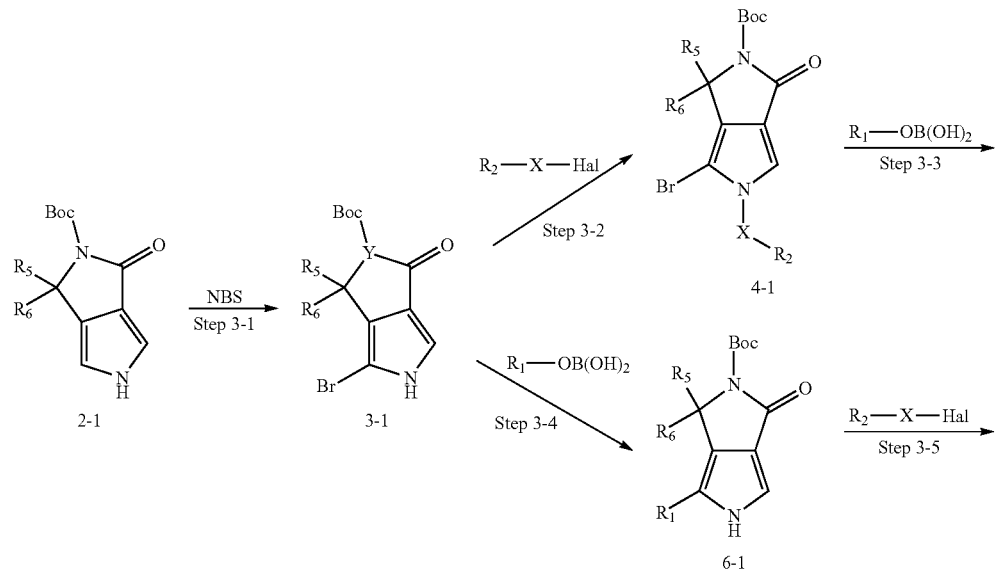

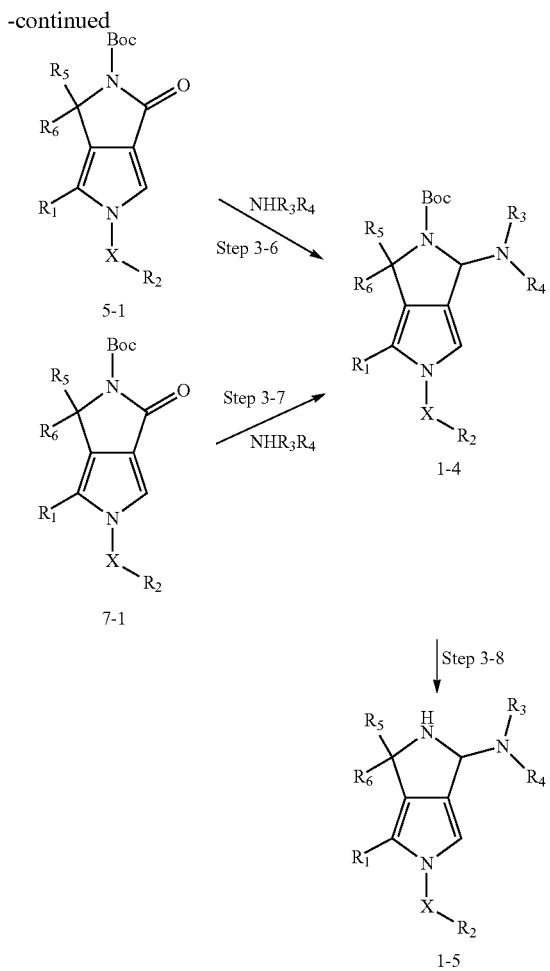

The steps 3-1, 3-2, 3-3, 3-4, 3-5, 3-6, and 3-7 are identical to the steps 1-1, 1-2, 1-3, 1-4, 1-5, 1-6, and 1-7, except that the starting material is different as a compound represented by the Chemical Formula 2-1. Namely, these steps are identical to the steps of the Reaction Scheme 1, except that —NH— in the compound represented by the Chemical Formula 2-1 has a protection group.

The step 3-8 is a deprotection reaction, wherein the protection group of a compound represented by the Chemical Formula 1-4 is removed to prepare a compound represented by the Chemical Formula 1-5. For the deprotection, any methods commonly used in the art may be used, and for example, the protection group may be removed using a hydrochloric acid solution.

The present invention also provides the following compounds that can be used as an intermediate in the Reaction Schemes 1 to 3:

5,6-dihydrocyclopenta[c]pyrrol-4(2H)-one,
1-bromo-5,6-dihydrocyclopenta[c]pyrrol-4(2H)-one,
1-bromo-2-((3-chlorophenyl)sulfonyl)-5,6-dihydrocyclopenta[c]pyrrol-4(2H)-one,
2-((3-chlorophenyl)sulfonyl)-1-(2-fluorophenyl)-5,6-dihydrocyclopenta[c]pyrrol-4(2H)-one,
1-bromo-2-(pyridin-3-ylsulfonyl)-5,6-dihydrocyclopenta[c]pyrrol-4(2H)-one,
1-(2-fluorophenyl)-2-(pyridin-3-ylsulfonyl)-5,6-dihydrocyclopenta[c]pyrrol-4(2H)-one,
6,6-dimethyl-5,6-dihydrocyclopenta[c]pyrrol-4(2H)-one,
1-bromo-6,6-dimethyl-5,6-dihydrocyclopenta[c]pyrrol-4(2H)-one,
1-(2-fluorophenyl)-6,6-dimethyl-5,6-dihydrocyclopenta[c]pyrrol-4(2H)-one,
1-(2-fluorophenyl)-6,6-dimethyl-2-(pyridin-3-ylsulfonyl)-5,6-dihydrocyclopenta[c]pyrrol-4(2H)-one,
1-(2-fluorophenyl)-5,6-dihydrocyclopenta[c]pyrrol-4(2H)-one,
2-(3-chlorobenzyl)-1-(2-fluorophenyl)-5,6-dihydrocyclopenta[c]pyrrol-4(2H)-one,
1-bromo-2-((3-fluorophenyl)sulfonyl)-5,6-dihydrocyclopenta[c]pyrrol-4(2H)-one,
1-(2,4-difluorophenyl)-2-((3-fluorophenyl)sulfonyl)-5,6-dihydrocyclopenta[c]pyrrol-4(2H)-one,
tert-butyl (1-(2,4-difluorophenyl)-2-((3-fluorophenyl)sulfonyl)-2,4,5,6-tetrahydrocyclopenta[c]pyrrol-4-yl)(methyl)carbamate,
tert-butyl (1-(2,4-difluorophenyl)-2,4,5,6-tetrahydrocyclopenta[c]pyrrol-4-yl)(methyl)carbamate,
tert-butyl (2-(3-chlorobenzoyl)-1-(2,4-difluorophenyl)-2,4,5,6-tetrahydrocyclopenta[c]pyrrol-4-yl)(methyl)carbamate,
tert-butyl 1-oxo-3,5-dihydropyrrolo[3,4-c]pyrrol-2(1H)-carboxylate,
tert-butyl 4-bromo-1-oxo-3,5-dihydropyrrolo[3,4-c]pyrrol-2(1H)-carboxylate, tert-butyl 4-(2-fluorophenyl)-1-oxo-3,5-dihydropyrrolo[3,4-c]pyrrol-2(1H)-carboxylate, tert-butyl 5-((3-chlorophenyl)sulfonyl)-4-(2-fluorophenyl)-1-oxo-3,5-dihydropyrrolo[3,4-c]pyrrol-2(1H)-carboxylate, tert-butyl 5-((3-chlorophenyl)sulfonyl)-4-(2-fluorophenyl)-1-(methylamino)-3,5-dihydropyrrolo[3,4-c]pyrrol-2(1H)-carboxylate, 4-(hydroxymethyl)-5-methyl-1,3-dioxol-2-one, (5-methyl-2-oxo-1,3-dioxol-4-yl)methyl (4-nitrophenyl) carbonate, 1-bromo-2,5,6,7-tetra-4H-isoindole-4-one, 1-(2-fluorophenyl)-2,5,6,7-tetrahydro-4H-isoindole-4-one, 1-(2-fluorophenyl)-2-((3-fluorophenyl)sulfonyl)-2,5,6,7-tetrahydro-4H-isoindole-4-one, 5,6,7,8-tetrahydrocyclohepta[c]pyrrol-4(2H)-one, 1-bromo-5,6,7,8-tetrahydrocyclohepta[c]pyrrol-4(2H)-one, 1-(2-fluorophenyl)-5,6,7,8-tetrahydrocyclohepta[c]pyrrol-4(2H)-one, and 2-((3-chlorophenyl)sulfonyl)-1-(2-fluorophenyl)-5,6,7,8-tetrahydrocyclohepta[c]pyrrol-4(2H)-one.

Hereinafter, the present invention will be explained in detail with reference to the following Preparation Examples and Examples. However, these Preparation Examples and Examples are only to illustrate the invention, and the scope of the invention is not limited thereto.

Preparation Example 1: Preparation of 5,6-dihydrocyclopenta[c]pyrrol-4(2H)-one

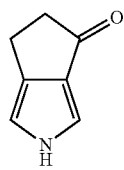

To a solution of 2-cyclopentene-1-one (5 g, 60.9 mmole) in tetrahydrofurane (60 ml), p-toluenesulfonylmethyl isocyanide (11.9 g, 60.9 mmole) was added, and the mixture was stirred at room temperature for 10 minutes, and then, a solution of tert-butoxide (8.2 g, 79.1 mmole) in tetrahydrofurane (60 ml) was slowly added dropwise for 1 hour. In the reaction mixture, water was introduced, and the solution was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:1 (v/v)) to prepare 1.6 g of the title compound (yield 21.7%).

$^1$H NMR (500 MHz, CD$_3$OD): 7.15 (s, 1H), 6.59 (s, 1H), 2.90-2.92 (m, 2H), 2.84-2.86 (m, 2H)

Example 1: Preparation of 2-((3-chlorophenyl)sulfonyl-1-(2-fluorophenyl)-N-methyl-2,4,5,6-tetrahydrocyclopenta[c]pyrrol-4-amine Step 1: Preparation of 1-bromo-5,6-dihydrocyclopenta[c]pyrrol-4(2H)-one

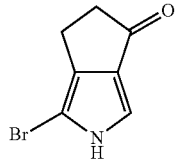

5,6-dihydrocyclopenta[c]pyrrol-4(2H)-one (1.6 g, 13.2 mmole) prepared in Preparation Example 1 was dissolved in a tetrahydrofurane solution (60 ml), and cooled to −78° C. N-bromosuccinimide (2.46 g, 13.9 mmole) was added, and then, the mixture was stirred at room temperature for 1 hour. The reaction mixture was concentrated under reduced pressure, water was added to the residue, and the mixture was extracted with ethyl acetate. The separated organic layer was washed with saturated brine, dried over anhydrous magnesium sulfate and concentrated under reduced pressure. The obtained residue was recrystallized from ethyl acetate to prepare 1.9 g of the title compound (yield 72%).

$^1$H NMR (500 MHz, CD$_3$OD): 7.16 (s, 1H), 2.85-2.88 (m, 2H), 2.77-2.80 (m, 2H)

Step 2: Preparation of 1-bromo-2-((3-chlorophenyl)sulfonyl)-5,6-dihydrocyclopenta[c]pyrrol-4(2H)-one

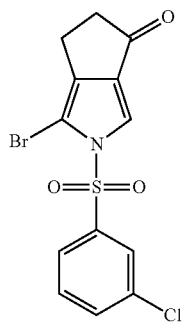 [SMILES: O=C1CCc2c1cn(S(=O)(=O)c1cccc(Cl)c1)c2Br]

1-bromo-5,6-dihydrocyclopenta[c]pyrrol-4(2H)-one (1.9 g, 9.5 mmole) prepared in the step 1 was dissolved in a N,N-dimethylformamide solution (50 ml), cooled to 0° C., and sodium hydride (60% in oil)(760 mg, 18.9 mmole) was added dropwise. The reaction mixture was stirred at 0° C. for 30 minutes, followed by introduction of 3-chlorobenzenesulfonyl chloride (3 g, 14.3 mmole) and stirring at 0° C. for 1 hour. In the reaction mixture, water was introduced, and the solution was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:3 (v/v)) to prepare 2.5 g of the title compound (yield 71%).

$^1$H NMR (500 MHz, CDCl$_3$): 8.23 (d, 1H), 7.86 (s, 1H), 7.64-7.77 (m, 3H), 3.03-3.07 (m, 2H), 2.45-2.56 (m, 2H)

Step 3: Preparation of 2-((3-chlorophenyl)sulfonyl)-1-(2-fluorophenyl)-5,6-dihydrocyclopenta[c]pyrrol-4(2H)-one

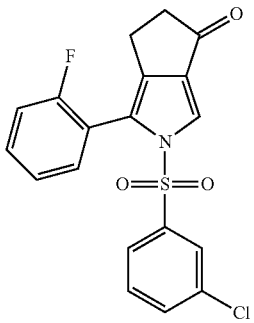 [SMILES: O=C1CCc2c1cn(S(=O)(=O)c1cccc(Cl)c1)c2-c1ccccc1F]

1-bromo-2-((3-chlorophenyl)sulfonyl)-5,6-dihydrocyclopenta[c]pyrrol-4(2H)-one (50 mg, 0.1 mmole) prepared in the step 2, 1,1'-bis(diphenylphosphino)ferrocene-palladium (II)dichloride dichloromethane complex (16 mg, 0.02 mmole), 2-fluorophenyl boric acid (28 mg, 0.2 mmole) were suspended in a mixture of 1,2-dimethoxyethane (1.5 ml) and 2M sodium carbonate (0.5 ml), and the mixture was reacted in a microwave reactor (120° C., 5 minutes). The reaction mixture was filtered through Celite, water was added to the filtrated, and the mixture was extracted with ethyl acetate. The extract was washed with saturated brine, dried over anhydrous magnesium sulfate, and concentrated under reduced pressure. The obtained residue was purified with silica gel column chromatography (ethyl acetate:n-hexane=1:2 (v/v)) to prepare 30 mg of the title compound (yield 57.7%).

$^{1}$H NMR (500 MHz, CDCl$_3$): 7.85 (s, 1H), 7.53-7.54 (m, 1H), 7.43-7.49 (m, 1H), 7.33-7.36 (m, 2H), 7.27-7.30 (m, 1H), 7.27-7.28 (m, 1H), 7.23 (t, 1H), 7.04 (t, 1H), 2.84-2.86 (m, 2H), 2.70-2.73 (m, 2H)

Step 4: Preparation of 2-((3-chlorophenyl)sulfonyl-1-(2-fluorophenyl)-N-methyl-2,4,5,6-tetrahydrocyclopenta[c]pyrrol-4-amine

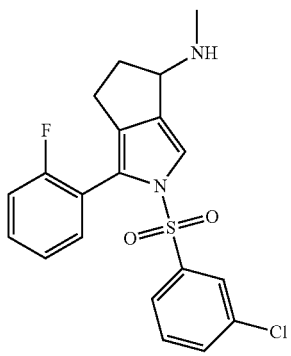 [SMILES: CNC1CCc2c1cn(S(=O)(=O)c1cccc(Cl)c1)c2-c1ccccc1F]

To a solution of 2-((3-chlorophenyl)sulfonyl)-1-(2-fluorophenyl)-5,6-dihydrocyclopenta[c]pyrrol-4(2H)-one (30 mg, 0.08 mmole) prepared in the step 3 in methanol (2 ml), tetraisopropoxytitanium(IV)(109 mg, 0.4 mmole) and 2M methylamine-tetrahydrofurane solution (0.2 ml, 0.4 mmole) were added, and the mixture was stirred at room temperature for 4 hours. Sodium borohydride (29 mg, 0.8 mmole) was put, and the mixture was stirred at room temperature for 1 hour, and then, concentrated under reduced pressure. A saturated aqueous solution of sodium bicarbonate was added thereto, and then, the mixture was extracted with ethyl acetate. The extract was washed with saturated brine, dried over anhydrous magnesium sulfate, and concentrated under reduced pressure. The obtained residue was purified with silica gel column chromatography (methanol:ethyl acetate=1:5 (v/v)) to prepare 19 mg of the title compound (yield 61%).

$^{1}$H NMR (500 MHz, CDCl$_3$): 7.46-7.49 (m, 1H), 7.38-7.40 (m, 2H), 7.31-7.32 (m, 4H), 7.16 (t, 1H), 7.03 (t, 1H), 4.16-4.17 (m, 1H), 2.57-2.63 (m, 2H), 2.53 (s, 3H), 2.41-2.44 (m, 1H), 2.21-2.23 (m, 1H)

In Examples 2 to 102 below, compounds were prepared by the same method as Example 1, except that reactants were appropriately changed considering the structure of the compound to be prepared and the Reaction Scheme 1.

Example 2: Preparation of 2-((3-chlorophenyl)sulfonyl)-N,1-dimethyl-2,4,5,6-tetrahydrocyclopenta[c]pyrrol-4-amine

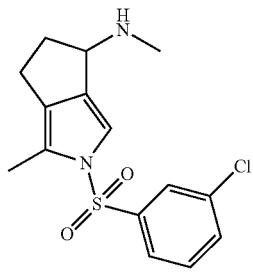 [SMILES: CNC1CCc2c1cn(S(=O)(=O)c1cccc(Cl)c1)c2C]

$^{1}$H NMR (500 MHz, CD$_3$OD): 7.80-7.85 (m, 1H), 7.75 (d, 1H), 7.63-7.68 (m, 1H), 7.54-7.60 (m, 1H), 7.16 (s, 1H), 3.91-3.97 (m, 1H), 2.57-2.62 (m, 1H), 2.47-2.54 (m, 1H), 2.36-2.45 (m, 4H), 2.21 (s, 3H), 2.00-2.08 (m, 1H)

Example 3: Preparation of 2-((3-chlorophenyl)sulfonyl)-N-methyl-1-phenyl-2,4,5,6-tetrahydrocyclopenta[c]pyrrol-4-amine

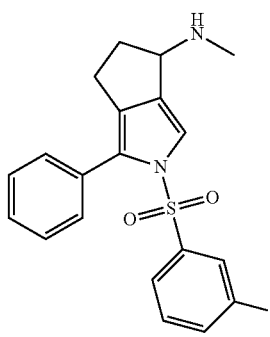

$^{1}$H NMR (500 MHz, CD$_3$OD): 7.58 (d, 1H), 7.31-7.43 (m, 6H), 7.25 (s, 1H), 7.19 (d, 2H), 4.06-4.13 (m, 1H), 2.52-2.65 (m, 2H), 2.46 (s, 3H), 2.40-2.44 (m, 1H), 2.08-2.14 (m, 1H)

Example 4: Preparation of 2-((3-chlorophenyl)sulfonyl)-N-methyl-1-(o-tolyl)-2,4,5,6-tetrahydrocyclopenta[c]pyrrol-4-amine

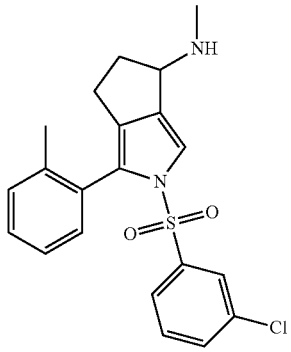 [SMILES: CNC1CCc2c1cn(S(=O)(=O)c1cccc(Cl)c1)c2-c1ccccc1C]

$^1$H NMR (500 MHz, CD$_3$OD): 7.47-7.49 (m, 1H), 7.27-7.32 (m, 4H), 7.24 (br, 1H), 7.12-7.17 (m, 2H), 6.97-6.99 (m, 1H), 4.11-4.12 (m, 1H), 2.54 (s, 3H), 2.41-2.46 (m, 1H), 2.21-2.34 (m, 2H), 1.98-2.08 (m, 1H), 1.85 (d, 3H)

Example 5: Preparation of 1-(2-chlorophenyl)-2-((3-chlorophenyl)sulfonyl)-N-methyl-2,4,5,6-tetrahydrocyclopenta[c]pyrrol-4-amine

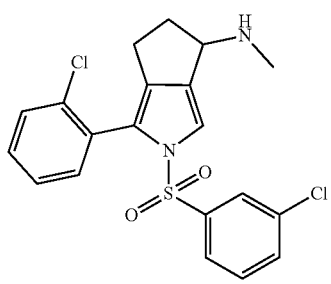 [SMILES: CNC1CCc2c1cn(S(=O)(=O)c1cccc(Cl)c1)c2-c1ccccc1Cl]

$^1$H NMR (500 MHz, CD$_3$OD): 7.61-7.63 (m, 1H), 7.37-7.44 (m, 5H), 7.31-7.34 (m, 1H), 7.28 (d, 2H), 4.07-4.08 (m, 1H), 2.53-2.66 (m, 2H), 2.46 (d, 3H), 2.26-2.33 (m, 1H), 2.09-2.14 (m, 1H)

Example 6: Preparation of 2-((3-chlorophenyl)sulfonyl)-1-(2-(cyclopent-3-en-1-yl)phenyl)-N-methyl-2,4,5,6-tetrahydrocyclopenta[c]pyrrol-4-amine

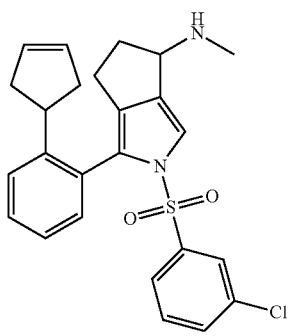 [SMILES: CNC1CCc2c1cn(S(=O)(=O)c1cccc(Cl)c1)c2-c1ccccc1C1CC=CC1]

$^1$H NMR (500 MHz, CD$_3$OD): 7.57 (d, 1H), 7.46 (d, 1H), 7.34-7.40 (m, 4H), 7.29 (t, 1H), 7.24 (s, 1H), 7.17 (s, 1H), 7.04 (d, 1H), 6.17 (s, 1H), 4.05-4.07 (m, 1H), 2.52-2.68 (m, 6H), 2.46 (s, 3H), 2.40-2.44 (m, 1H), 2.00-2.13 (m, 2H)

Example 7: Preparation of 2-((3-chlorophenyl)sulfonyl)-N-methyl-1-(2-(morpholinophenyl)-2,4,5,6-tetrahydrocyclopenta[c]pyrrol-4-amine

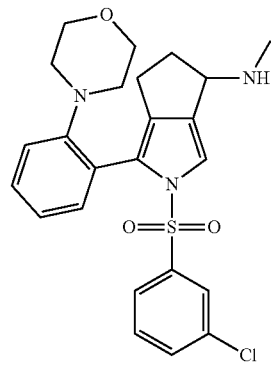 [SMILES: CNC1CCc2c1cn(S(=O)(=O)c1cccc(Cl)c1)c2-c1ccccc1N1CCOCC1]

$^1$H NMR (500 MHz, CD$_3$OD): 7.61-7.62 (m, 1H), 7.34-7.47 (m, 5H), 7.04-7.06 (m, 1H), 6.96-7.01 (m, 1H), 6.92 (dd, 0.5H), 6.87 (dd, 0.5H), 4.10-4.18 (m, 1H), 3.51-3.63 (m, 4H), 2.73-2.75 (m, 1H), 2.52-2.68 (m, 5H), 2.41-2.48 (m, 4H), 2.11-2.16 (m, 1H)

Example 8: Preparation of 2-((3-chlorophenyl)sulfonyl)-N-methyl-1-(m-tolyl)-2,4,5,6-tetrahydrocyclopenta[c]pyrrol-4-amine

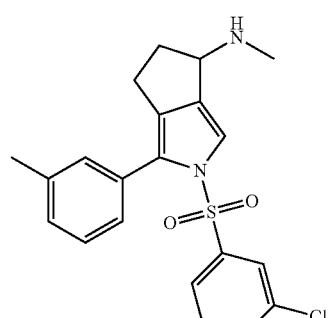

$^1$H NMR (500 MHz, CD$_3$OD): 7.59 (d, 1H), 7.40 (t, 1H), 7.34-7.36 (m, 2H), 7.18-7.25 (m, 3H), 6.99 (d, 1H), 6.92 (s, 1H), 4.02-4.05 (m, 1H), 2.50-2.63 (m, 2H), 2.45 (s, 3H), 2.38-2.42 (m, 1H), 2.33 (s, 3H), 2.06-2.12 (m, 1H)

Example 9: Preparation of 2-((3-chlorophenyl)sulfonyl)-1-(3-fluorophenyl)-N-methyl-2,4,5,6-tetrahydrocyclopenta[c]pyrrol-4-amine

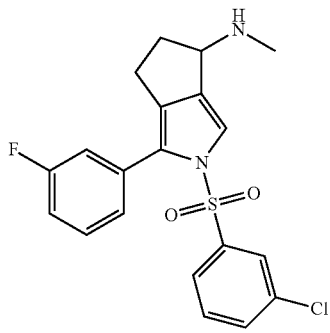 [SMILES: CNC1CCc2c1cn(S(=O)(=O)c1cccc(Cl)c1)c2-c1cccc(C)c1]

¹H NMR (500 MHz, CD₃OD): 7.60 (d, 1H), 7.42 (t, 1H), 7.34-7.39 (m, 3H), 7.32 (s, 1H), 7.11 (t, 1H), 7.01 (d, 1H), 6.96 (d, 1H), 3.99-4.01 (m, 1H), 2.59-2.65 (m, 1H), 2.50-2.57 (m, 1H), 2.41-2.45 (m, 4H), 2.06-2.12 (m, 1H)

Example 10: Preparation of 2-((3-chlorophenyl)sulfonyl)-N-methyl-1-(3-(trifluoromethyl)phenyl)-2,4,5,6-tetrahydrocyclopenta[c]pyrrol-4-amine

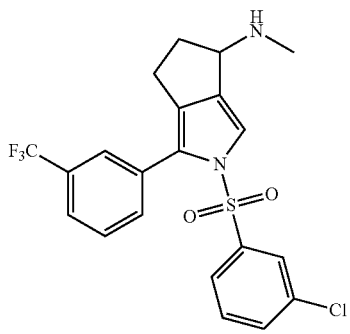 [SMILES: CNC1CCc2c1cn(S(=O)(=O)c1cccc(Cl)c1)c2-c1cccc(C(F)(F)F)c1]

¹H NMR (500 MHz, CD₃OD): 7.67 (d, 1H), 7.55-7.62 (m, 2H), 7.49 (d, 1H), 7.45 (s, 1H), 7.40-7.43 (m, 2H), 7.34 (d, 1H), 7.28 (s, 1H), 4.02-4.04 (m, 1H), 2.52-2.66 (m, 2H), 2.41-2.47 (m, 4H), 2.08-2.14 (m, 1H)

Example 11: Preparation of 2-((3-chlorophenyl)sulfonyl)-1-(4-fluorophenyl)-N-methyl-2,4,5,6-tetrahydrocyclopenta[c]pyrrol-4-amine

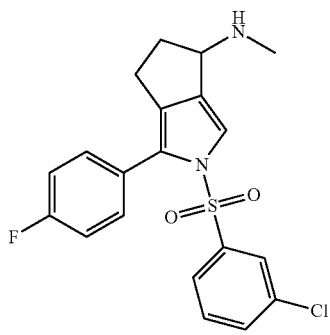 [SMILES: CNC1CCc2c1cn(S(=O)(=O)c1cccc(Cl)c1)c2-c1ccc(F)cc1]

¹H NMR (500 MHz, CD₃OD): 7.60 (d, 1H), 7.42 (t, 1H), 7.34-7.36 (m, 2H), 7.27 (s, 1H), 7.19-7.22 (m, 2H), 7.09 (t, 2H), 4.01-4.04 (m, 1H), 2.50-2.63 (m, 2H), 2.44 (s, 3H), 2.38-2.43 (m, 1H), 2.06-2.12 (m, 1H)

Example 12: Preparation of 4-(2-((3-chlorophenyl)sulfonyl)-4-(methylamino)-2,4,5,6-tetrahydrocyclopenta[c]pyrrol-1-yl)phenol

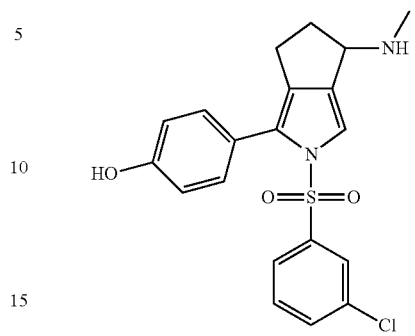

¹H NMR (500 MHz, CD₃OD): 7.58 (d, 1H), 7.39 (t, 1H), 7.34 (d, 2H), 7.25 (s, 1H), 6.98 (d, 2H), 6.75 (d, 2H), 4.07-4.09 (m, 1H), 2.52-2.63 (m, 2H), 2.48 (s, 3H), 2.38-2.43 (m, 1H), 2.09-2.13 (m, 1H)

Example 13: Preparation of 4-(2-((3-chlorophenyl)sulfonyl)-4-(methylamino)-2,4,5,6-tetrahydrocyclopenta[c]pyrrol-1-yl)benzonitrile

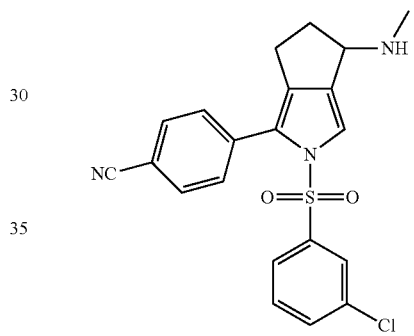

¹H NMR (500 MHz, CD₃OD): 7.74 (d, 2H), 7.62 (d, 1H), 7.42-7.45 (m, 4H), 7.34-7.37 (m, 2H), 4.03-4.05 (m, 1H), 2.52-2.68 (m, 2H), 2.45-2.49 (m, 1H), 2.43 (s, 3H), 2.10-2.14 (m, 1H)

Example 14: Preparation of 2-((3-chlorophenyl)sulfonyl)-1-(4-methoxyphenyl)-N-methyl-2,4,5,6-tetrahydrocyclopenta[c]pyrrol-4-amine

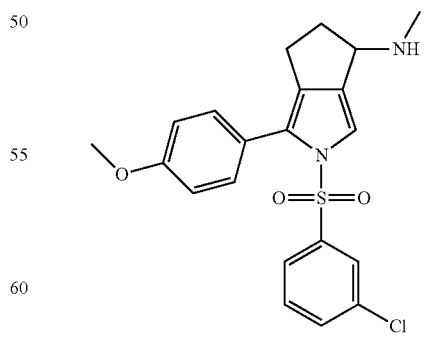

¹H NMR (500 MHz, CD₃OD): 7.58 (dd, 1H), 7.40 (t, 1H), 7.33-7.35 (m, 2H), 7.23 (t, 1H), 7.08 (d, 2H), 6.89 (d, 2H), 4.06-4.08 (m, 1H), 3.84 (s, 3H), 2.52-2.63 (m, 2H), 2.47 (s, 3H), 2.38-2.43 (m, 1H), 2.08-2.13 (m, 1H)

Example 15: Preparation of methyl 4-(2-((3-chloro-phenyl)sulfonyl)-4-(methylamino)-2,4,5,6-tetrahydrocyclopenta[c]pyrrol-1-yl)benzoate

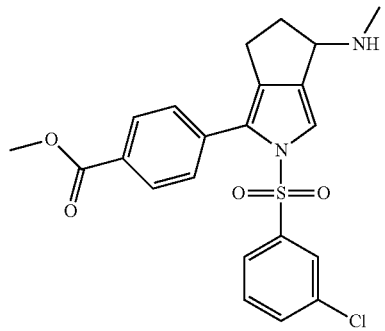

¹H NMR (500 MHz, CD₃OD): 8.01 (d, 2H), 7.61 (dd, 1H), 7.48 (s, 1H), 7.42 (t, 1H), 7.36 (d, 3H), 7.30-7.31 (m, 1H), 4.18-4.20 (m, 1H), 3.93 (s, 3H), 2.58-2.70 (m, 2H), 2.47-2.52 (m, 4H), 2.16-2.24 (m, 1H)

Example 16: Preparation of 2-((3-chlorophenyl)sulfonyl)-N-methyl-1-(4-(trifluoromethyl)phenyl)-2,4,5,6-tetrahydrocyclopenta[c]pyrrol-4-amine

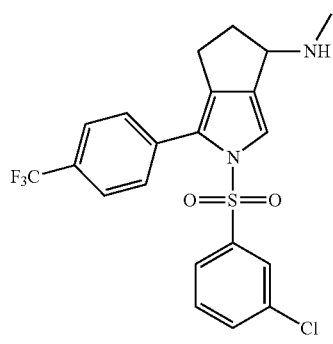 [SMILES: CNC1CCc2c1cn(S(=O)(=O)c1cccc(Cl)c1)c2-c1ccc(C(F)(F)F)cc1]

¹H NMR (500 MHz, CD₃OD): 7.67 (d, 2H), 7.61 (dd, 1H), 7.41-7.44 (m, 4H), 7.37 (d, 1H), 7.30-7.31 (m, 1H), 4.07-4.13 (m, 1H), 2.55-2.68 (m, 2H), 2.45-2.50 (m, 4H), 2.13-2.19 (m, 1H)

Example 17: Preparation of 2-((3-chlorophenyl)sulfonyl)-N-methyl-1-(4-(trifluoromethoxy)phenyl)-2,4,5,6-tetrahydrocyclopenta[c]pyrrol-4-amine

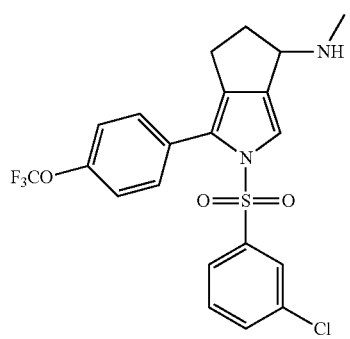 [SMILES: CNC1CCc2c1cn(S(=O)(=O)c1cccc(Cl)c1)c2-c1ccc(OC(F)(F)F)cc1]

¹H NMR (500 MHz, CD₃OD): 7.61 (dd, 1H), 7.39-7.43 (m, 2H), 7.35 (d, 1H), 7.26-7.32 (m, 5H), 4.05-4.10 (m, 1H), 2.52-2.66 (m, 2H), 2.41-2.47 (m, 4H), 2.09-2.15 (m, 1H)

Example 18: Preparation of 2-((3-chlorophenyl)sulfonyl)-1-(2-fluoro-4-methylphenyl)-N-methyl-2,4,5,6-tetrahydrocyclopenta[c]pyrrol-4-amine

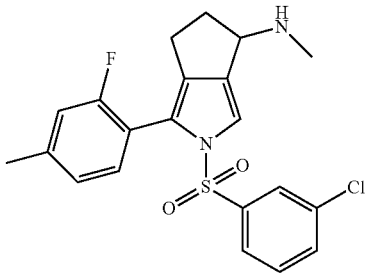 [SMILES: CNC1CCc2c1cn(S(=O)(=O)c1cccc(Cl)c1)c2-c1ccc(C)cc1F]

¹H NMR (500 MHz, CD₃OD): 7.61 (d, 1H), 7.39-7.45 (m, 3H), 7.29 (s, 1H), 7.00-7.06 (m, 2H), 6.91 (d, 1H), 4.06-4.08 (m, 1H), 2.52-2.60 (m, 2H), 2.46 (s, 3H), 2.41 (s, 3H), 2.33-2.38 (m, 1H), 2.07-2.14 (m, 1H)

Example 19: Preparation of 2-((3-chlorophenyl)sulfonyl)-1-(2,4-difluorophenyl)-N-methyl-2,4,5,6-tetrahydrocyclopenta[c]pyrrol-4-amine

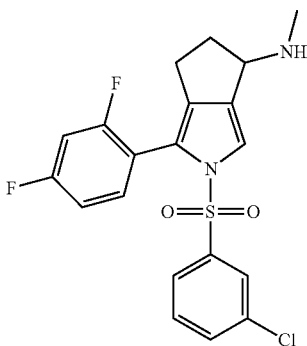 [SMILES: CNC1CCc2c1cn(S(=O)(=O)c1cccc(Cl)c1)c2-c1ccc(F)cc1F]

¹H NMR (500 MHz, CDCl₃): 7.48-7.50 (m, 1H), 7.31-7.34 (m, 3H), 7.27 (s, 1H), 7.15-7.22 (m, 2H), 7.07-7.10 (m, 1H), 4.02-4.04 (m, 1H), 2.53-2.59 (m, 2H), 2.49 (s, 3H), 2.34-2.37 (m, 1H), 2.04-2.10 (m, 1H)

Example 20: Preparation of 1-(4-chloro-2-fluorophenyl)-2-((3-chlorophenyl)sulfonyl)-N-methyl-2,4,5,6-tetrahydrocyclopenta[c]pyrrol-4-amine

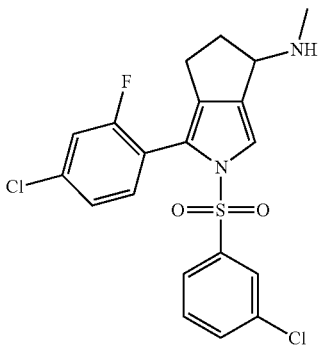 [SMILES: CNC1CCc2c1cn(S(=O)(=O)c1cccc(Cl)c1)c2-c1ccc(Cl)cc1F]

¹H NMR (500 MHz, CDCl₃): 7.48-7.50 (m, 1H), 7.33 (s, 3H), 7.21-7.27 (m, 2H), 6.89-6.92 (m, 1H), 6.78-6.82 (m, 1H), 4.01-4.03 (m, 1H), 2.48-2.58 (m, 5H), 2.32-2.37 (m, 1H), 2.01-2.08 (m, 1H)

Example 21: Preparation of 2-((3-chlorophenyl)sulfonyl)-1-(2,4-dichlorophenyl)-N-methyl-2,4,5,6-tetrahydrocyclopenta[c]pyrrol-4-amine

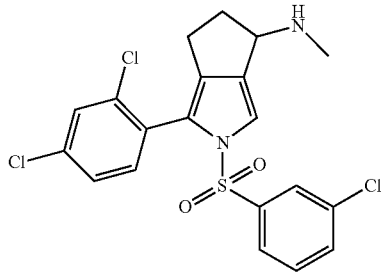 [SMILES: CNC1CCc2c1cn(S(=O)(=O)c1cccc(Cl)c1)c2-c1ccc(Cl)cc1Cl]

¹H NMR (500 MHz, CD₃OD): 7.63-7.64 (m, 1H), 7.43-7.49 (m, 4H), 7.37-7.39 (m, 1H), 7.32 (d, 1H), 7.28 (t, 1H), 4.10-4.11 (m, 1H), 2.52-2.66 (m, 2H), 2.45 (d, 3H), 2.28-2.41 (m, 1H), 2.12-2.18 (m, 1H)

Example 22: Preparation of 1-(5-chloro-2-fluorophenyl)-2-((3-chlorophenyl)sulfonyl)-N-methyl-2,4,5,6-tetrahydrocyclopenta[c]pyrrol-4-amine

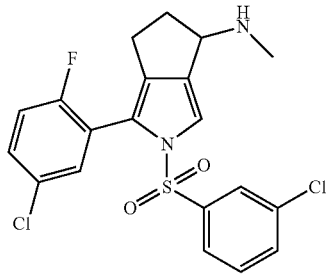 [SMILES: CNC1CCc2c1cn(S(=O)(=O)c1cccc(Cl)c1)c2-c1cc(Cl)ccc1F]

¹H NMR (500 MHz, CD₃OD): 7.65 (d, 1H), 7.42-7.49 (m, 4H), 7.39 (s, 1H), 7.11-7.16 (m, 2H), 4.04-4.06 (m, 1H), 2.53-2.61 (m, 2H), 2.44 (s, 3H), 2.36-2.41 (m, 1H), 2.08-2.14 (m, 1H)

Example 23: Preparation of 2-((3-chlorophenyl)sulfonyl)-1-(2,5-dichlorophenyl)-N-methyl-2,4,5,6-tetrahydrocyclopenta[c]pyrrol-4-amine

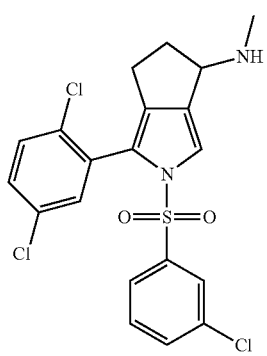 [SMILES: CNC1CCc2c1cn(S(=O)(=O)c1cccc(Cl)c1)c2-c1cc(Cl)ccc1Cl]

¹H NMR (500 MHz, CD₃OD): 7.64-7.66 (m, 1H), 7.44-7.48 (m, 3H), 7.42 (d, 1H), 7.40 (d, 1H), 7.36-7.39 (m, 1H), 7.22 (dd, 1H), 4.12 (br, 1H), 2.58-2.63 (m, 2H), 2.48 (d, 3H), 2.32-2.43 (m, 1H), 2.11-2.17 (m, 1H)

Example 24: Preparation of 2-((3-chlorophenyl)sulfonyl)-1-(3,4-difluorophenyl)-N-methyl-2,4,5,6-tetrahydrocyclopenta[c]pyrrol-4-amine

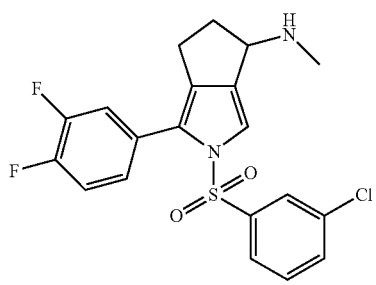 [SMILES: CNC1CCc2c1cn(S(=O)(=O)c1cccc(Cl)c1)c2-c1ccc(F)c(F)c1]

¹H NMR (500 MHz, CD₃OD): 7.62 (d, 1H), 7.44 (t, 1H), 7.34-7.39 (m, 3H), 7.23-7.29 (m, 1H), 7.11-7.15 (m, 1H), 6.98-7.00 (m, 1H), 4.00-4.02 (m, 1H), 2.51-2.63 (m, 2H), 2.39-2.45 (m, 4H), 2.09-2.11 (m, 1H)

Example 25: Preparation of 2-((3-chlorophenyl)sulfonyl)-1-(3,5-dichlorophenyl)-N-methyl-2,4,5,6-tetrahydrocyclopenta[c]pyrrol-4-amine

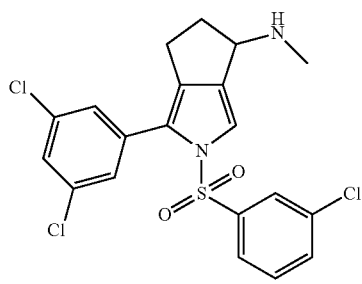 [SMILES: CNC1CCc2c1cn(S(=O)(=O)c1cccc(Cl)c1)c2-c1cc(Cl)cc(Cl)c1]

¹H NMR (500 MHz, CD₃OD): 7.65 (d, 1H), 7.47 (t, 2H), 7.36-7.42 (m, 3H), 7.14 (d, 2H), 4.05-4.07 (s, 1H), 2.55-2.66 (m, 2H), 2.43-2.48 (m, 4H), 2.11-2.15 (m, 1H)

Example 26: Preparation of 1-(5-chloro-2-fluoro-4-methylphenyl)-2-((3-chlorophenyl)sulfonyl)-N-methyl-2,4,5,6-tetrahydrocyclopenta[c]pyrrol-4-amine

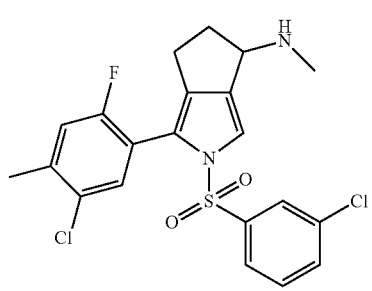 [SMILES: CNC1CCc2c1cn(S(=O)(=O)c1cccc(Cl)c1)c2-c1cc(Cl)c(C)cc1F]

¹H NMR (500 MHz, CD₃OD): 7.65 (d, 1H), 7.43-7.49 (m, 3H), 7.33-7.35 (m, 2H), 6.96-6.97 (m, 1H), 4.06-4.08 (m, 1H), 2.54-2.63 (m, 2H), 2.46 (s, 3H), 2.35-2.40 (m, 1H), 2.24 (s, 3H), 2.09-2.15 (m, 1H)

Example 27: Preparation of 1-benzyl-2-((3-chlorophenyl)sulfonyl)-N-methyl-2,4,5,6-tetrahydrocyclopenta[c]pyrrol-4-amine

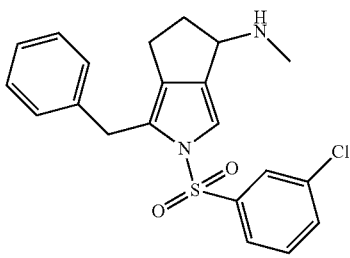 [SMILES: CNC1CCc2c1cn(S(=O)(=O)c1cccc(Cl)c1)c2Cc1ccccc1]

¹H NMR (500 MHz, CD₃OD): 7.53-7.57 (m, 3H), 7.40 (t, 1H), 7.30 (s, 1H), 7.13-7.16 (m, 3H), 6.98 (d, 2H), 4.12 (s, 2H), 4.04-4.09 (m, 1H), 2.47-2.52 (m, 1H), 2.46 (s, 3H), 2.33-2.39 (m, 1H), 2.17-2.21 (m, 1H), 2.04-2.07 (m, 1H)

Example 28: Preparation of 1-(benzo[d][1,3]dioxol-5-yl)-2-((3-chlorophenyl)sulfonyl)-N-methyl-2,4,5,6-tetrahydrocyclopenta[c]pyrrol-4-amine

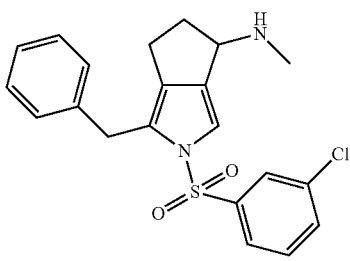 [SMILES: CNC1CCc2c1cn(S(=O)(=O)c1cccc(Cl)c1)c2Cc1ccccc1]

¹H NMR (500 MHz, CD₃OD): 7.60 (d, 1H), 7.38-7.44 (m, 2H), 7.32 (d, 2H), 6.79 (d, 1H), 6.64 (s, 1H), 6.59 (d, 1H), 6.00 (s, 2H), 4.03-4.05 (m, 1H), 2.52-2.63 (m, 2H), 2.45 (s, 3H), 2.39-2.43 (m, 1H), 2.07-2.14 (m, 1H)

Example 29: Preparation of 1-(benzofuran-5-yl)-2-((3-chlorophenyl)sulfonyl)-N-methyl-2,4,5,6-tetrahydrocyclopenta[c]pyrrol-4-amine

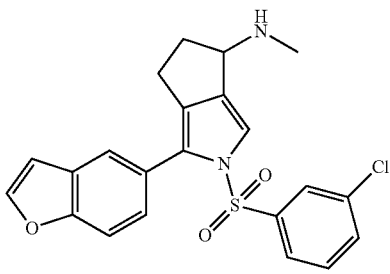 [SMILES: CNC1CCc2c1cn(S(=O)(=O)c1cccc(Cl)c1)c2-c1ccc2occc2c1]

¹H NMR (500 MHz, CD₃OD): 7.80 (s, 1H), 7.56 (d, 1H), 7.46 (d, 1H), 7.39 (s, 1H), 7.36 (d, 2H), 7.31 (d, 1H), 7.18 (s, 1H), 7.10 (dd, 1H), 6.84 (s, 1H), 4.02-4.04 (m, 1H), 2.51-2.65 (m, 2H), 2.44 (s, 3H), 2.37-2.42 (m, 1H), 2.06-2.12 (m, 1H)

Example 30: Preparation of 2-((3-chlorophenyl)sulfonyl)-N-methyl-1-(1-methyl-1H-pyrazol-4-yl)-2,4,5,6-tetrahydrocyclopenta[c]pyrrol-4-amine

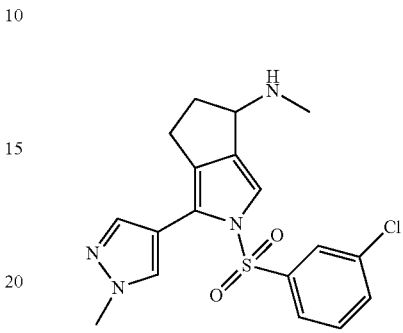

¹H NMR (500 MHz, CD₃OD): 7.58-7.61 (m, 2H), 7.42-7.43 (m, 2H), 7.38 (s, 2H), 7.34 (s, 1H), 4.03-4.05 (m, 1H), 3.91 (s, 3H), 2.52-2.67 (m, 3H), 2.45 (s, 3H), 2.10-2.14 (m, 1H)

Example 31: Preparation of 2-((3-chlorophenyl)sulfonyl)-1-(furan-3-yl)-N-methyl-2,4,5,6-tetrahydrocyclopenta[c]pyrrol-4-amine

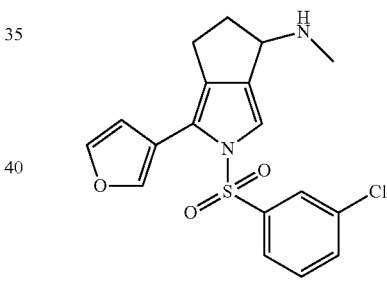

¹H NMR (500 MHz, CD₃OD): 7.61 (d, 1H), 7.42-7.53 (m, 5H), 7.31 (s, 1H), 6.47 (s, 1H), 4.09-4.13 (m, 1H), 2.56-2.70 (m, 3H), 2.49 (s, 3H), 2.12-2.16 (m, 1H)

Example 32: Preparation of 2-((3-chlorophenyl)sulfonyl)-N-methyl-1-(5-methylfuran-2-yl)-2,4,5,6-tetrahydrocyclopenta[c]pyrrol-4-amine

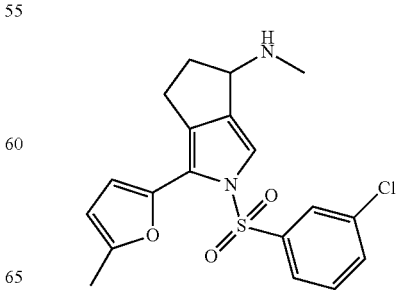

¹H NMR (500 MHz, CD₃OD): 7.61-7.65 (m, 3H), 7.49 (t, 1H), 7.35 (s, 1H), 6.38 (d, 1H), 6.07 (s, 1H), 3.99-4.01 (m, 1H), 2.68-2.75 (m, 1H), 2.46-2.58 (m, 2H), 2.42 (s, 3H), 2.25 (s, 3H), 2.05-2.12 (m, 1H)

Example 33: Preparation of 2-((3-chlorophenyl)sulfonyl)-N-methyl-1-(thiophen-3-yl)-2,4,5,6-tetrahydrocyclopenta[c]pyrrol-4-amine

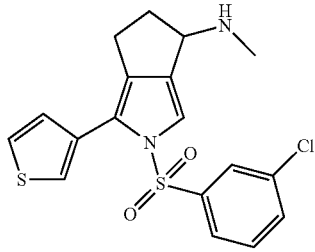 [SMILES: CNC1CCc2c1cn(S(=O)(=O)c1cccc(Cl)c1)c2-c1ccsc1]

¹H NMR (500 MHz, CD₃OD): 7.58 (d, 1H), 7.39-7.41 (m, 2H), 7.36-7.38 (m, 1H), 7.35 (s, 1H), 7.31 (s, 1H), 7.24 (s, 1H), 7.03 (d, 1H), 4.03-4.05 (m, 1H), 2.61-2.67 (m, 1H), 2.51-2.58 (m, 1H), 2.42-2.48 (m, 4H), 2.07-2.14 (m, 1H)

Example 34: Preparation of 2-((3-chlorophenyl)sulfonyl)-N-methyl-1-(4-methylthiophen-3-yl)-2,4,5,6-tetrahydrocyclopenta[c]pyrrol-4-amine

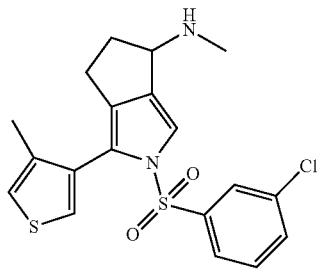 [SMILES: CNC1CCc2c1cn(S(=O)(=O)c1cccc(Cl)c1)c2-c1cscc1C]

¹H NMR (500 MHz, CD₃OD): 7.63 (d, 1H), 7.42-7.44 (m, 3H), 7.27 (s, 1H), 7.04-7.08 (m, 1H), 6.99 (s, 1H), 4.05-4.07 (m, 1H), 2.53-2.57 (m, 2H), 2.45 (s, 3H), 2.32-2.35 (m, 1H), 2.07-2.10 (m, 1H), 1.71 (s, 3H)

Example 35: Preparation of 2-((3-chlorophenyl)sulfonyl)-1-(2,5-dimethylthiophen-3-yl)-N-methyl-2,4,5,6-tetrahydrocyclopenta[c]pyrrol-4-amine

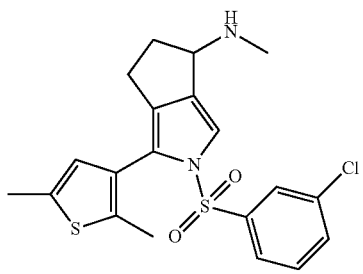 [SMILES: CNC1CCc2c1cn(S(=O)(=O)c1cccc(Cl)c1)c2-c1cc(C)sc1C]

¹H NMR (500 MHz, CD₃OD): 7.62 (d, 1H), 7.42-7.47 (m, 2H), 7.38 (d, 1H), 7.34 (d, 1H), 6.42 (d, 1H), 4.01-4.08 (m, 1H), 2.51-2.57 (m, 2H), 2.45 (d, 3H), 2.40 (s, 3H), 2.25-2.34 (m, 1H), 2.07-2.11 (m, 1H), 1.77 (d, 3H)

Example 36: Preparation of 2-((3-chlorophenyl)sulfonyl)-1-(6-chloropyridin-2-yl)-N-methyl-2,4,5,6-tetrahydrocyclopenta[c]pyrrol-4-amine

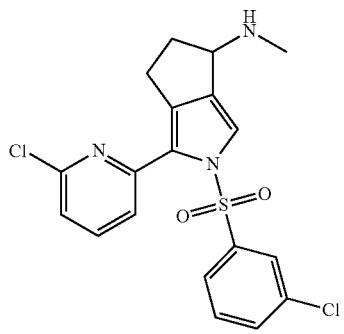 [SMILES: CNC1CCc2c1cn(S(=O)(=O)c1cccc(Cl)c1)c2-c1cccc(Cl)n1]

¹H NMR (500 MHz, CDCl₃): 7.93 (s, 1H), 7.79 (d, 1H), 7.64 (t, 1H), 7.56 (d, 1H), 7.45 (t, 1H), 7.38 (s, 1H), 7.33 (d, 1H), 7.19 (d, 1H), 4.04-4.06 (m, 1H), 2.76-2.79 (m, 1H), 2.56-2.62 (m, 2H), 2.51 (s, 3H), 2.09-2.15 (m, 1H)

Example 37: Preparation of 2-((3-chlorophenyl)sulfonyl)-N-methyl-1-(pyridin-3-yl)-2,4,5,6-tetrahydrocyclopenta[c]pyrrol-4-amine

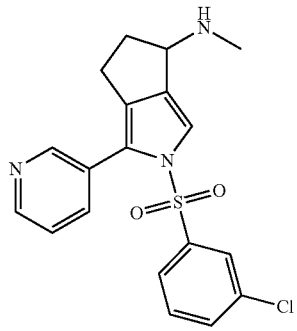 [SMILES: CNC1CCc2c1cn(S(=O)(=O)c1cccc(Cl)c1)c2-c1cccnc1]

¹H NMR (500 MHz, CD₃OD): 8.53 (dd, 1H), 8.35 (s, 1H), 7.76 (d, 1H), 7.63 (d, 1H), 7.46-7.49 (m, 1H), 7.45 (d, 2H), 7.33 (d, 2H), 4.01-4.03 (m, 1H), 2.62-2.68 (m, 1H), 2.52-2.59 (m, 1H), 2.44-2.49 (m, 1H), 2.42 (s, 1H), 2.08-2.14 (m, 1H)

Example 38: Preparation of 2-((3-chlorophenyl)sulfonyl)-N-methyl-1-(2-trifluoromethyl)pyridin-3-yl)-2,4,5,6-tetrahydrocyclopenta[c]pyrrol-4-amine

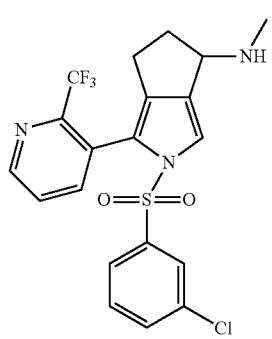 [SMILES: CNC1CCc2c1cn(S(=O)(=O)c1cccc(Cl)c1)c2-c1cccnc1C(F)(F)F]

$^1$H NMR (500 MHz, CD$_3$OD): 8.05 (t, 1H), 7.76-7.78 (m, 2H), 7.72 (t, 2H), 7.67 (d, 1H), 7.51 (t, 2H), 4.20-4.22 (m, 1H), 2.74-2.84 (m, 1H), 2.61-2.70 (m, 2H), 2.53 (s, 3H), 2.21-2.26 (m, 1H)

Example 39: Preparation of 2-((3-chlorophenyl)sulfonyl)-N-methyl-1-(6-trifluoromethyl)pyridin-3-yl)-2,4,5,6-tetrahydrocyclopenta[c]pyrrol-4-amine

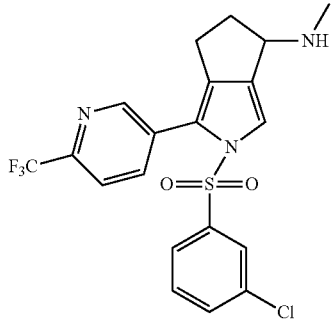 [SMILES: CNC1CCc2c1cn(S(=O)(=O)c1cccc(Cl)c1)c2-c1ccc(C(F)(F)F)nc1]

$^1$H NMR (500 MHz, CD$_3$OD): 8.57 (s, 1H), 7.97 (d, 1H), 7.85 (d, 1H), 7.64 (d, 1H), 7.46 (t, 2H), 7.38 (t, 2H), 4.03-4.05 (m, 1H), 2.66-2.72 (m, 1H), 2.48-2.59 (m, 2H), 2.43 (s, 3H), 2.10-2.16 (m, 1H)

Example 40: Preparation of 2-((3-chlorophenyl)sulfonyl)-N-methyl-1-(6-pyrrolidin-1-yl)pyridin-3-yl)-2,4,5,6-tetrahydrocyclopenta[c]pyrrol-4-amine

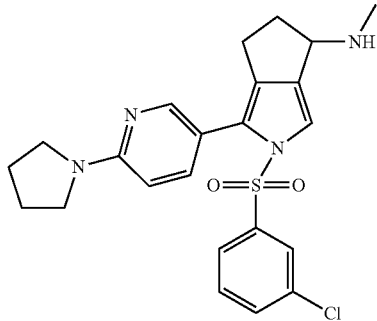 [SMILES: CNC1CCc2c1cn(S(=O)(=O)c1cccc(Cl)c1)c2-c1ccc(N2CCCC2)nc1]

$^1$H NMR (500 MHz, CD$_3$OD): 7.67 (d, 1H), 7.59 (d, 1H), 7.43 (t, 1H), 7.35-7.38 (m, 3H), 7.31 (s, 1H), 6.50 (d, 1H), 4.05-4.07 (m, 1H), 3.47-3.50 (m, 4H), 2.52-2.65 (m, 2H), 2.46 (s, 3H), 2.40-2.43 (m, 1H), 2.10-2.14 (m, 1H), 2.00-2.09 (m, 4H)

Example 41: Preparation of 2-((3-chlorophenyl)sulfonyl)-N-methyl-1-(6-morpholinopyridin-3-yl)-2,4,5,6-tetrahydrocyclopenta[c]pyrrol-4-amine

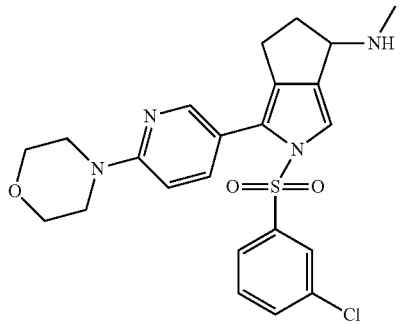 [SMILES: CNC1CCc2c1cn(S(=O)(=O)c1cccc(Cl)c1)c2-c1ccc(N2CCOCC2)nc1]

$^1$H NMR (500 MHz, CD$_3$OD): 7.80 (d, 1H), 7.61 (d, 1H), 7.42-7.45 (m, 2H), 7.36-7.39 (m, 2H), 7.31 (s, 1H), 6.82 (d, 1H), 4.08-4.11 (m, 1H), 3.81 (t, 4H), 3.55 (t, 4H), 2.54-2.66 (m, 2H), 2.48 (s, 3H), 2.40-2.47 (m, 1H), 2.15-2.18 (m, 1H)

Example 42: Preparation of 2-((3-chlorophenyl)sulfonyl)-N-methyl-1-(pyridin-4-yl)-2,4,5,6-tetrahydrocyclopenta[c]pyrrol-4-amine

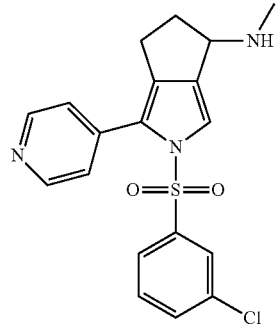 [SMILES: CNC1CCc2c1cn(S(=O)(=O)c1cccc(Cl)c1)c2-c1ccncc1]

$^1$H NMR (500 MHz, CD$_3$OD): 8.54 (d, 2H), 7.64 (d, 1H), 7.47-7.48 (m, 1H), 7.43-7.45 (m, 1H), 7.40-7.42 (m, 2H), 7.36-7.39 (m, 2H), 4.08-4.10 (m, 1H), 2.67-2.74 (m, 1H), 2.50-2.62 (m, 2H), 2.45 (s, 3H), 2.13-2.19 (m, 1H)

Example 43: Preparation of 1-(2-fluorophenyl)-N-methyl-2-(phenylsulfonyl)-2,4,5,6-tetrahydrocyclopenta[c]pyrrol-4-amine

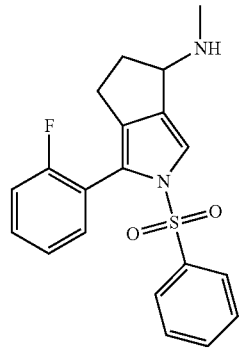 [SMILES: CNC1CCc2c1cn(S(=O)(=O)c1ccccc1)c2-c1ccccc1F]

$^1$H NMR (500 MHz, CD$_3$OD): 7.49-7.52 (m, 1H), 7.41 (d, 2H), 7.32-7.35 (m, 4H), 7.23-7.26 (m, 1H), 7.12 (t, 1H), 7.00 (t, 1H), 4.04-4.07 (m, 1H), 2.52-2.58 (m, 2H), 2.49 (s, 3H), 2.34-2.40 (m, 1H), 2.05-2.12 (m, 1H)

Example 44: Preparation of 1-(2-fluoro-4-methylphenyl)-N-methyl-2-(phenylsulfonyl)-2,4,5,6-tetrahydrocyclopenta[c]pyrrol-4-amine

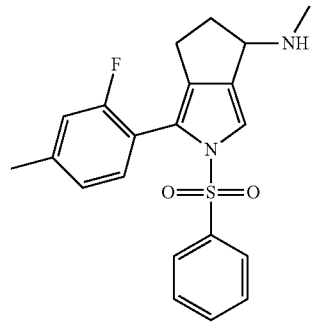

¹H NMR (500 MHz, CD₃OD): 7.57-7.60 (m, 1H), 7.40-7.44 (m, 4H), 7.38 (s, 1H), 6.96-7.03 (m, 2H), 6.89 (d, 1H), 4.04-4.06 (m, 1H), 2.50-2.57 (m, 2H), 2.44 (s, 3H), 2.40 (s, 3H), 2.32-2.38 (m, 1H), 2.08-2.11 (m, 1H)

Example 45: Preparation of 1-(2,5-dichlorophenyl)-N-methyl-2-(phenylsulfonyl)-2,4,5,6-tetrahydrocyclopenta[c]pyrrol-4-amine

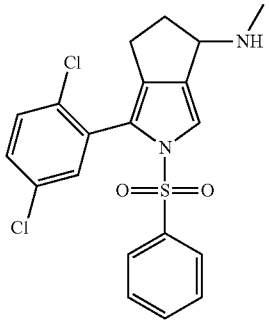 [SMILES: CNC1CCc2c1cn(S(=O)(=O)c1ccccc1)c2-c1cc(Cl)ccc1Cl]

¹H NMR (500 MHz, CD₃OD): 7.63-7.67 (m, 1H), 7.55 (d, 1H), 7.46-7.50 (m, 4H), 7.36-7.43 (m, 2H), 7.11 (s, 1H), 4.29-4.31 (m, 1H), 2.63-2.70 (m, 1H), 2.56 (d, 3H), 2.34-2.55 (m, 2H), 2.20-2.26 (m, 1H)

Example 46: Preparation of 1-(2-fluorophenyl)-2-((2-methoxyphenyl)sulfonyl)-N-methyl-2,4,5,6-tetrahydrocyclopenta[c]pyrrol-4-amine

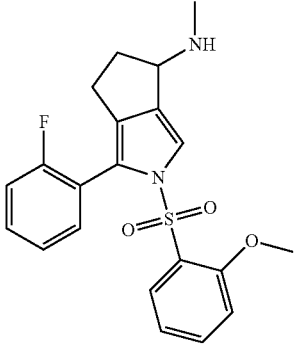 [SMILES: CNC1CCc2c1cn(S(=O)(=O)c1ccccc1OC)c2-c1ccccc1F]

¹H NMR (500 MHz, CDCl₃): 7.43-7.45 (m, 2H), 7.18-7.23 (d, 3H), 7.01-7.04 (m, 1H), 6.89 (d, 1H), 6.80 (t, 1H), 6.72 (t, 1H), 4.11-4.13 (m, 1H), 3.77 (s, 3H), 2.58-2.63 (m, 1H), 2.55 (s, 3H), 2.36-2.44 (m, 2H), 2.14-2.16 (m, 1H)

Example 47: Preparation of 1-(2-fluoro-4-methylphenyl)-2-((3-fluorophenyl)sulfonyl)-N-methyl-2,4,5,6-tetrahydrocyclopenta[c]pyrrol-4-amine

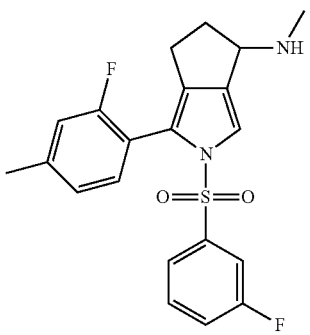

¹H NMR (500 MHz, CD₃OD): 7.44-7.50 (m, 2H), 7.36-7.39 (m, 1H), 7.29 (d, 1H), 7.11-7.13 (m, 1H), 7.05 (t, 1H), 7.00 (d, 1H), 6.91 (d, 1H), 4.16-4.18 (m, 1H), 2.53-2.62 (m, 2H), 2.51 (s, 3H), 2.36-2.42 (m, 4H), 2.15-2.18 (m, 1H)

Example 48: Preparation of 2-((2-chlorophenyl)sulfonyl)-1-(2-fluoro-4-methylphenyl)-N-methyl-2,4,5,6-tetrahydrocyclopenta[c]pyrrol-4-amine

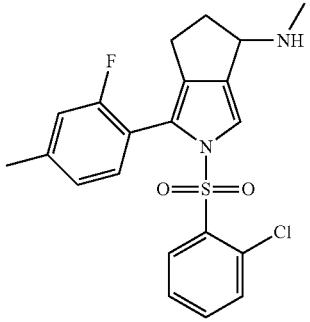

¹H NMR (500 MHz, CD₃OD): 7.61 (s, 1H), 7.50-7.57 (m, 2H), 7.27 (dd, 1.4 Hz, 1H), 7.17 (t, 1H), 6.96 (t, 1H), 6.88 (d, 1H), 6.68 (d, 1H), 4.32-4.35 (m, 1H), 2.61-2.73 (m, 2H), 2.60 (s, 3H), 2.40-2.46 (m, 1H), 2.33 (s, 3H), 2.24-2.30 (m, 1H)

Example 49: Preparation of 2-((2-chlorophenyl)sulfonyl)-1-(4-fluoro-2-methylphenyl)-N-methyl-2,4,5,6-tetrahydrocyclopenta[c]pyrrol-4-amine

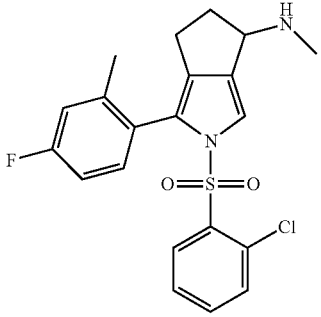 [SMILES: CNC1CCc2c1cn(S(=O)(=O)c1ccccc1Cl)c2-c1ccc(F)cc1C]

¹H NMR (500 MHz, CDCl₃): 7.48 (s, 1H), 7.39-7.44 (m, 2H), 7.20 (d, 1H), 7.06-7.09 (m, 1H), 6.87-6.91 (m, 1H), 6.65-6.68 (m, 2H), 4.08-4.10 (m, 1H), 2.54-2.61 (m, 4H), 2.42-2.50 (m, 1H), 2.26-2.29 (m, 1H), 2.08-2.12 (m, 1H), 1.81 (s, 3H)

Example 50: Preparation of 2-((2-chlorophenyl)sulfonyl)-1-(2,5-dichlorophenyl)-N-methyl-2,4,5,6-tetrahydrocyclopenta[c]pyrrol-4-amine

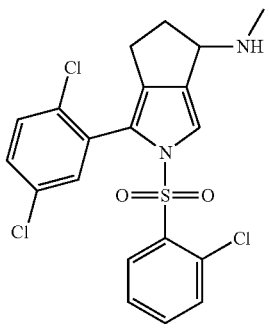 [SMILES: CNC1CCc2c1cn(S(=O)(=O)c1ccccc1Cl)c2-c1cc(Cl)ccc1Cl]

¹H NMR (500 MHz, CD₃OD): 7.58-7.61 (m, 2H), 7.54-7.55 (m, 1H), 7.28-7.34 (m, 2H), 7.19-7.25 (m, 2H), 7.10 (dd, 1H), 4.25-4.29 (m, 1H), 2.61-2.70 (m, 2H), 2.56 (d, 3H), 2.35-2.49 (m, 1H), 2.21-2.26 (m, 1H)

Example 51: Preparation of 1-(2,5-dichlorophenyl)-2-((3-fluorophenyl)sulfonyl)-N-methyl-2,4,5,6-tetrahydrocyclopenta[c]pyrrol-4-amine

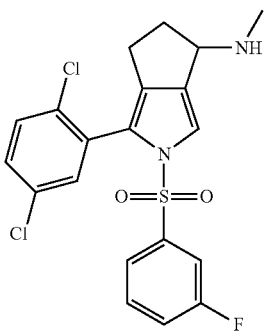 [SMILES: CNC1CCc2c1cn(S(=O)(=O)c1cccc(F)c1)c2-c1cc(Cl)ccc1Cl]

¹H NMR (500 MHz, CD₃OD): 7.58 (d, 1H), 7.51-7.55 (m, 1H), 7.38-7.45 (m, 3H), 7.33-7.35 (m, 1H), 7.18-7.22 (m, 2H), 4.33-4.36 (m, 1H), 2.65-2.73 (m, 1H), 2.61 (d, 3H), 2.37-2.51 (m, 2H), 2.23-2.29 (m, 1H)

Example 52: Preparation of 1-(2-fluoro-4-methylphenyl)-N-methyl-2-(m-tolylsulfonyl)-2,4,5,6-tetrahydrocyclopenta[c]pyrrol-4-amine

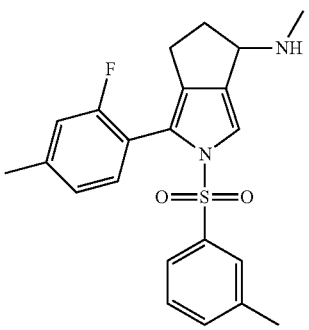

¹H NMR (500 MHz, CD₃OD): 7.41 (s, 2H), 7.25-7.32 (m, 2H), 7.15 (s, 1H), 6.98-7.04 (m, 2H), 6.90 (d, 1H), 4.08-4.13 (m, 1H), 2.51-2.61 (m, 2H), 2.48 (s, 3H), 2.40 (s, 3H), 2.33-2.38 (m, 1H), 2.28 (s, 3H), 2.09-2.16 (m, 1H)

Example 53: Preparation of 1-(2,5-dichlorophenyl)-N-methyl-2-(m-tolylsulfonyl)-2,4,5,6-tetrahydrocyclopenta[c]pyrrol-4-amine

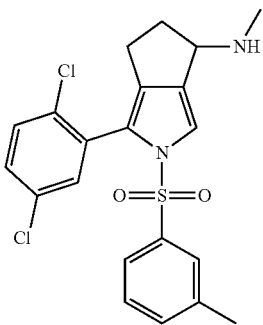 [SMILES: CNC1CCc2c1cn(S(=O)(=O)c1cccc(C)c1)c2-c1cc(Cl)ccc1Cl]

¹H NMR (500 MHz, CD₃OD): 7.54 (d, 1H), 7.47 (d, 1H), 7.39-7.44 (m, 2H), 7.32-7.37 (m, 2H), 7.21 (d, 1H), 7.13 (d, 1H), 4.29-4.31 (m, 1H), 2.62-2.69 (m, 1H), 2.59 (d, 3H), 2.34-2.55 (m, 2H), 2.33 (s, 3H), 2.20-2.27 (m, 1H)

Example 54: Preparation of 1-(2-fluoro-4-methylphenyl)-2-((3-methoxyphenyl)sulfonyl)-N-methyl-2,4,5,6-tetrahydrocyclopenta[c]pyrrol-4-amine

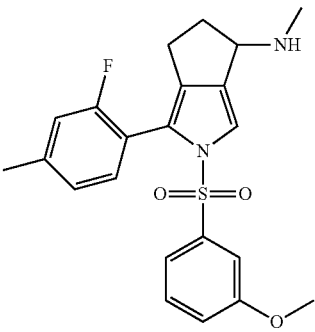

¹H NMR (500 MHz, CD₃OD): 7.52 (s, 1H), 7.35 (t, 1H), 7.14 (dd, 1H), 7.04-7.08 (m, 2H), 7.00 (d, 1H), 6.91 (d, 1H), 6.86 (s, 1H), 4.30-4.33 (m, 1H), 3.73 (s, 3H), 2.57-2.69 (m, 5H), 2.40-2.45 (m, 4H), 2.23-2.28 (m, 1H)

Example 55: Preparation of 1-(2,5-dichlorophenyl)-2-((3-methoxyphenyl)sulfonyl)-N-methyl-2,4,5,6-tetrahydrocyclopenta[c]pyrrol-4-amine

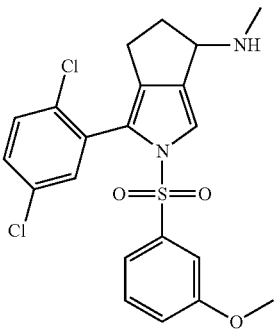 [SMILES: CNC1CCc2c1cn(S(=O)(=O)c1cccc(OC)c1)c2-c1cc(Cl)ccc1Cl]

¹H NMR (500 MHz, CD₃OD): 7.46 (s, 1H), 7.36-7.41 (m, 3H), 7.12-7.18 (m, 2H), 7.09 (d, 1H), 6.91 (d, 1H), 4.12-4.15 (m, 1H), 3.76 (s, 3H), 2.56-2.64 (m, 2H), 2.49 (d, 3H), 2.30-2.45 (m, 1H), 2.10-2.17 (m, 1H)

Example 56: Preparation of 2-((3-(dimethylamino)phenyl)sulfonyl)-1-(2-fluorophenyl)-N-methyl-2,4,5,6-tetrahydrocyclopenta[c]pyrrol-4-amine

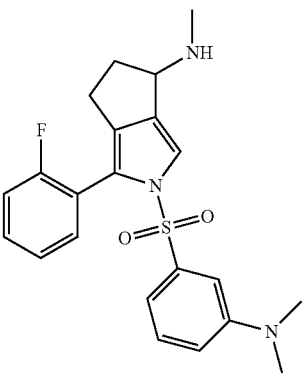 [SMILES: CNC1CCc2c1cn(S(=O)(=O)c1cccc(N(C)C)c1)c2-c1ccccc1F]

¹H NMR (500 MHz, CD₃OD): 7.42 (1s, 1H), 7.13-7.23 (m, 4H), 7.07 (t, 1H), 6.89 (dd, 1H), 6.76 (d, 1H), 6.59 (s, 1H), 4.13-4.16 (m, 1H), 2.86 (s, 6H), 2.55-2.62 (m, 2H), 2.49 (s, 3H), 2.35-2.42 (m, 1H), 2.13-2.18 (m, 1H)

Example 57: Preparation of 2-((3-(difluoromethoxy) phenyl)sulfonyl)-1-(2-fluorophenyl)-N-methyl-2,4,5,6-tetrahydrocyclopenta[c]pyrrol-4-amine

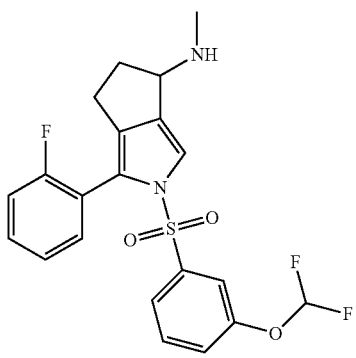 [SMILES: CNC1CCc2c1cn(S(=O)(=O)c1cccc(OC(F)F)c1)c2-c1ccccc1F]

¹H NMR (500 MHz, CDCl₃): 7.24-7.39 (m, 6H), 7.11-7.16 (m, 2H), 7.02 (t, J=9.1 Hz, 1H), 6.31-6.60 (m, 1H), 4.08-4.10 (m, 1H), 2.54-2.61 (m, 2H), 2.50 (s, 3H), 2.36-2.42 (m, 1H), 2.11-2.17 (m, 1H)

Example 58: Preparation of (3-((1-(2-fluorophenyl)-4-(methylamino)-5,6-dihydrocyclopenta[c]pyrrol-2(4H)-yl)sulfonyl)phenyl)(morpholino)methanone

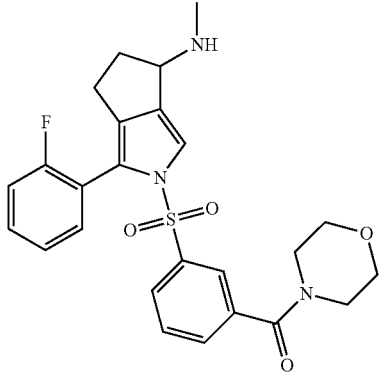 [SMILES: CNC1CCc2c1cn(S(=O)(=O)c1cccc(C(=O)N3CCOCC3)c1)c2-c1ccccc1F]

¹H NMR (500 MHz, CDCl₃): 7.59 (d, J=7.35 Hz, 1H), 7.41-7.46 (m, 3H), 7.33-7.36 (m, 1H), 7.25-7.30 (m, 2H), 7.15 (t, J=7.45 Hz, 1H), 7.02 (t, J=9.1 Hz, 1H), 4.02-4.05 (m, 1H), 3.76 (br, 4H), 3.48 (br, 2H), 3.26 (br, 2H), 2.52-2.57 (m, 1H), 2.49 (s, 3H), 2.35-2.38 (m, 1H), 2.04-2.10 (m, 2H)

Example 59: Preparation of 1-(2-fluorophenyl)-N-methyl-2-tosyl-2,4,5,6-tetrahydrocyclopenta[c]pyrrol-4-amine

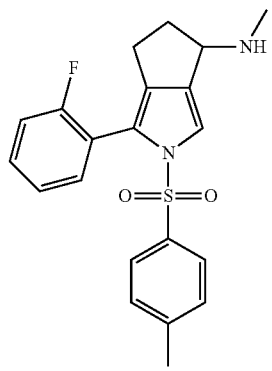 [SMILES: CNC1CCc2c1cn(S(=O)(=O)c1ccc(C)cc1)c2-c1ccccc1F]

¹H NMR (500 MHz, CD₃OD): 7.39-7.43 (m, 2H), 7.31 (d, 2H), 7.23 (d, 2H), 7.14-7.18 (m, 2H), 7.07 (t, 1H), 4.08-4.10 (m, 1H), 2.53-2.60 (m, 2H), 2.47 (s, 3H), 2.32-2.41 (m, 4H), 2.10-2.15 (m, 1H)

Example 60: Preparation of 1-(2-fluoro-4-methylphenyl)-2-((4-fluorophenyl)sulfonyl)-N-methyl-2,4,5,6-tetrahydrocyclopenta[c]pyrrol-4-amine

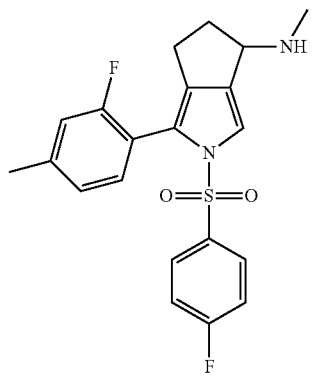

¹H NMR (500 MHz, CD₃OD): 7.48-7.51 (m, 3H), 7.19 (t, 2H), 6.99-7.06 (m, 2H), 6.91 (d, 1H), 4.28-4.30 (m, 1H), 2.56-2.68 (m, 5H), 2.40-2.44 (m, 4H), 2.21-2.27 (m, 1H)

Example 61: Preparation of 1-(2,5-dichlorophenyl)-2-((4-fluorophenyl)sulfonyl)-N-methyl-2,4,5,6-tetrahydrocyclopenta[c]pyrrol-4-amine

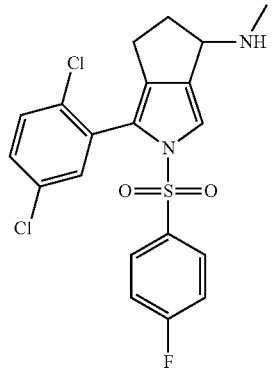 [SMILES: CNC1CCc2c1cn(S(=O)(=O)c1ccc(F)cc1)c2-c1cc(Cl)ccc1Cl]

¹H NMR (500 MHz, CD₃OD): 7.51-7.56 (m, 3H), 7.37-7.43 (m, 2H), 7.23 (t, 2H), 7.17-7.18 (m, 1H), 4.23-4.24 (m, 1H), 2.60-2.68 (m, 1H), 2.56 (d, 3H), 2.33-2.53 (m, 2H), 2.19-2.23 (m, 1H)

Example 62: Preparation of 2-([1,1'-biphenyl]-4-ylsulfonyl)-1-(2-fluorophenyl)-N-methyl-2,4,5,6-tetrahydrocyclopenta[c]pyrrol-4-amine

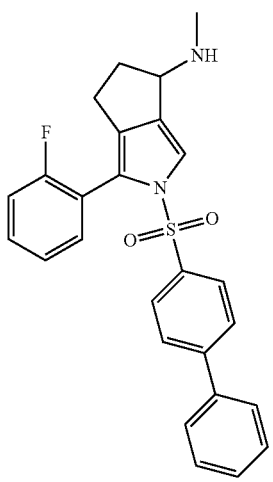 [SMILES: CNC1CCc2c1cn(S(=O)(=O)c1ccc(-c3ccccc3)cc1)c2-c1ccccc1F]

¹H NMR (500 MHz, CD₃OD): 7.68 (d, 2H), 7.62 (d, 2H), 7.40-7.53 (m, 7H), 7.18-7.24 (m, 2H), 7.09 (t, 1H), 4.26-4.28 (m, 1H), 2.60-2.68 (m, 2H), 2.58 (s, 3H), 2.40-2.47 (m, 1H), 2.18-2.25 (m, 1H)

Example 63: Preparation of 2-((3-chloro-2-methylphenyl)sulfonyl)-1-(2-fluorophenyl)-N-methyl-2,4,5,6-tetrahydrocyclopenta[c]pyrrol-4-amine

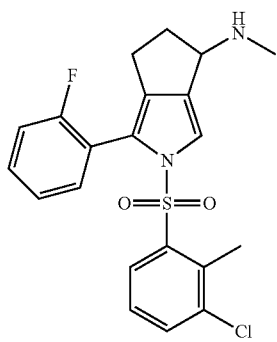 [SMILES: CNC1CCc2c1cn(S(=O)(=O)c1cccc(Cl)c1C)c2-c1ccccc1F]

¹H NMR (500 MHz, CDCl₃): 7.53 (s, 1H), 7.44 (d, 1H), 7.18-7.23 (m, 2H), 7.00-7.03 (m, 2H), 6.87 (t, 1H), 6.77 (t, 1H), 4.29 (br, 1H), 2.60-2.68 (m, 2H), 2.57 (s, 3H), 2.41-2.42 (m, 1H), 2.38 (s, 3H), 2.28-2.30 (m, 1H)

Example 64: Preparation of 2-((2,3-dichlorophenyl)sulfonyl)-1-(2-fluorophenyl)-N-methyl-2,4,5,6-tetrahydrocyclopenta[c]pyrrol-4-amine

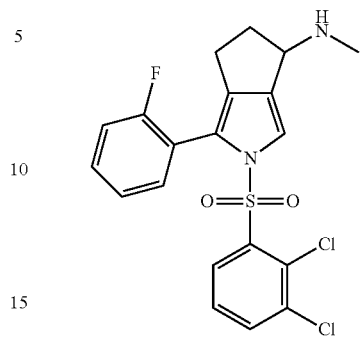

¹H NMR (500 MHz, CD₃OD): 7.75 (dd, 1H), 7.54 (s, 1H), 7.31-7.35 (m, 1H), 7.20 (dd, 1H), 7.11-7.16 (m, 2H), 7.06-7.07 (m, 1H), 6.86 (t, 1H), 4.15-4.18 (m, 1H), 2.56-2.65 (m, 2H), 2.50 (s, 3H), 2.38-2.43 (m, 1H), 2.17-2.21 (m, 1H)

Example 65: Preparation of 2-((2,4-difluorophenyl)sulfonyl)-1-(2-fluorophenyl)-N-methyl-2,4,5,6-tetrahydrocyclopenta[c]pyrrol-4-amine

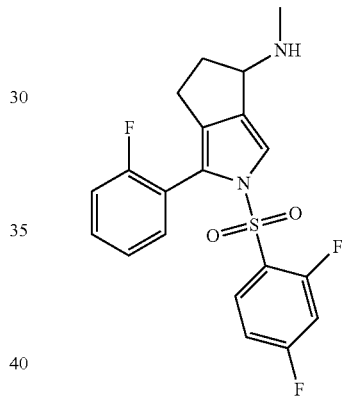

¹H NMR (500 MHz, CDCl₃): 7.38 (s, 1H), 7.29-7.32 (m, 1H), 7.18-7.22 (m, 2H), 7.08-7.11 (m, 1H), 6.91-6.94 (m, 1H), 6.82-6.86 (m, 1H), 6.71-6.74 (m, 1H), 4.08-4.12 (m, 1H), 2.57-2.60 (m, 1H), 2.52 (s, 3H), 2.36-2.42 (m, 1H), 2.12-2.21 (m, 2H)

Example 66: Preparation of 2-((2-chloro-4-fluorophenyl)sulfonyl)-1-(2-fluorophenyl)-N-methyl-2,4,5,6-tetrahydrocyclopenta[c]pyrrol-4-amine

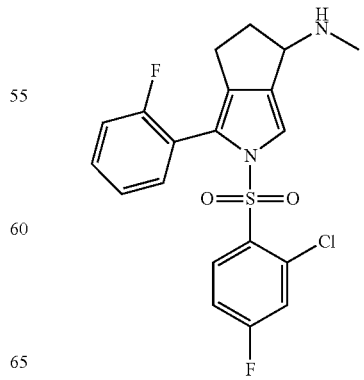

¹H NMR (500 MHz, CD₃OD): 7.72 (s, 1H), 7.43 (dd, 1H), 7.37-7.39 (m, 1H), 7.33 (q, 1H), 7.09-7.16 (m, 2H), 6.89-6.97 (m, 2H), 4.48-4.50 (m, 1H), 2.72-2.78 (m, 1H), 2.68 (s, 3H), 2.38-2.50 (m, 3H)

Example 67: Preparation of 3-chloro-4-((1-(2-fluorophenyl)-4-(methylamino)-5,6-dihydrocyclopenta[c]pyrrol-2(4H)-yl)sulfonyl)benzonitrile

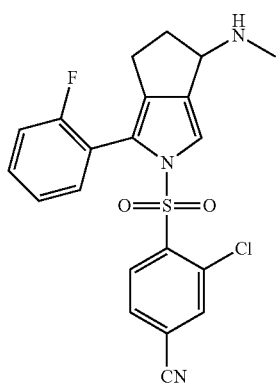 [SMILES: CNC1CCc2c1cn(S(=O)(=O)c1ccc(C#N)cc1Cl)c2-c1ccccc1F]

¹H NMR (500 MHz, CD₃OD): 8.00 (s, 1H), 7.61 (s, 1H), 7.57 (dd, 1H), 7.36-7.39 (m, 2H), 7.10-7.15 (m, 2H), 6.91 (t, 1H), 4.27-4.30 (m, 1H), 2.59-2.70 (m, 2H), 2.57 (s, 3H), 2.41-2.47 (m, 1H), 2.25-2.29 (m, 1H)

Example 68: Preparation of 2-((2-chloro-4-(trifluoromethoxy)phenyl)sulfonyl)-1-(2-fluorophenyl)-N-methyl-2,4,5,6-tetrahydrocyclopenta[c]pyrrol-4-amine

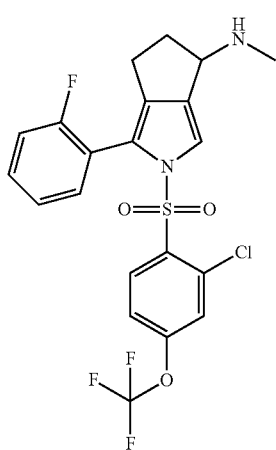 [SMILES: CNC1CCc2c1cn(S(=O)(=O)c1ccc(OC(F)(F)F)cc1Cl)c2-c1ccccc1F]

¹H NMR (500 MHz, CD₃OD): 7.65 (s, 1H), 7.52 (s, 1H), 7.33-7.37 (m, 2H), 7.15 (t, 1H), 7.10 (d, 2H), 6.85 (t, 1H), 4.33-4.35 (m, 1H), 2.63-2.77 (m, 2H), 2.61 (s, 3H), 2.41-2.46 (m, 1H), 2.29-2.34 (m, 1H)

Example 69: Preparation of 2-((2-chloro-4-(trifluoromethyl)phenyl)sulfonyl)-1-(2-fluorophenyl)-N-methyl-2,4,5,6-tetrahydrocyclopenta[c]pyrrol-4-amine

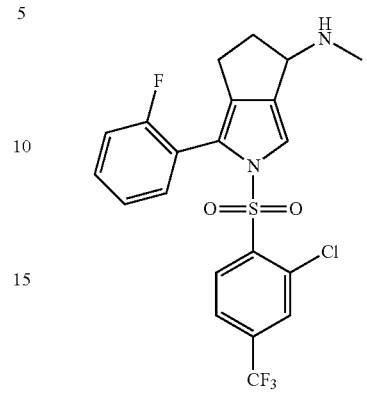

¹H NMR (500 MHz, CD₃OD): 7.89 (s, 1H), 7.56 (s, 1H), 7.50 (d, 1H), 7.43 (d, 1H), 7.33-7.37 (m, 1H), 7.13-7.16 (m, 1H), 7.08 (t, 1H), 6.85 (t, 1H), 4.16-4.18 (m, 1H), 2.57-2.66 (m, 2H), 2.51 (s, 3H), 2.38-2.43 (m, 1H), 2.17-2.20 (m, 1H)

Example 70: Preparation of 2-((2,5-dichlorophenyl)sulfonyl)-1-(2-fluorophenyl)-N-methyl-2,4,5,6-tetrahydrocyclopenta[c]pyrrol-4-amine

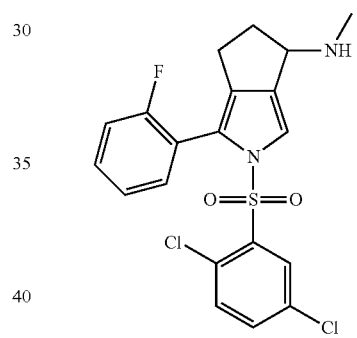

¹H NMR (500 MHz, CD₃OD): 7.60 (s, 1H), 7.58 (dd, 1H), 7.52 (d, 1H), 7.38-7.43 (m, 1H), 7.11-7.14 (m, 3H), 6.91 (t, 1H), 4.26-4.28 (m, 1H), 2.60-2.70 (m, 2H), 2.56 (s, 3H), 2.41-2.47 (m, 1H), 2.22-2.27 (m, 1H)

Example 71: Preparation of 2-((2,5-dichlorophenyl)sulfonyl)-1-(2,4-difluorophenyl)-N-methyl-2,4,5,6-tetrahydrocyclopenta[c]pyrrol-4-amine

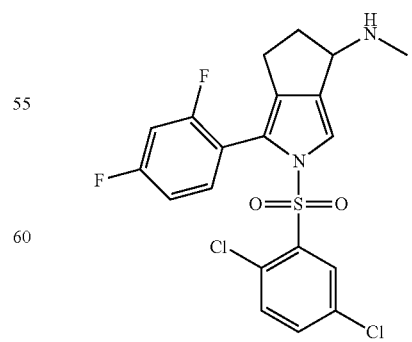

¹H NMR (500 MHz, CDCl₃): 7.50 (s, 1H), 7.40 (dd, 1H), 7.34 (d, 1H), 7.16-7.20 (m, 2H), 6.84-6.87 (m, 1H), 6.60-

6.64 (m, 1H), 4.13-4.15 (m, 1H), 2.57-2.66 (m, 2H), 2.54 (s, 3H), 2.39-2.42 (m, 1H), 2.18-2.21 (m, 1H)

Example 72: Preparation of 2-((2,5-dichlorophenyl)sulfonyl)-1-(2-fluoro-4-methylphenyl)-N-methyl-2,4,5,6-tetrahydrocyclopenta[c]pyrrol-4-amine

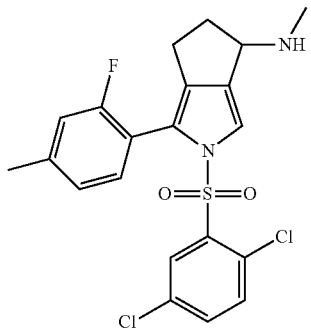

¹H NMR (500 MHz, CD₃OD): 7.64 (s, 1H), 7.58 (dd, 1H), 7.51 (d, 1H), 7.13 (d, 1H), 6.94-7.00 (m, 2H), 6.71 (d, 1H), 4.35-4.37 (m, 1H), 2.62-2.73 (m, 2H), 2.61 (s, 3H), 2.42-2.48 (m, 1H), 2.37 (s, 3H), 2.26-2.32 (m, 1H)

Example 73: Preparation of 1-(2,5-dichlorophenyl)-2-((2,5-dichlorophenyl)sulfonyl)-N-methyl-2,4,5,6-tetrahydrocyclopenta[c]pyrrol-4-amine

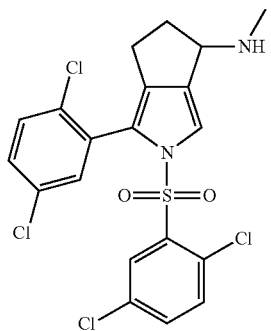 [SMILES: CNC1CCc2c1cn(S(=O)(=O)c1cc(Cl)ccc1Cl)c2-c1cc(Cl)ccc1Cl]

¹H NMR (500 MHz, CD₃OD): 7.62-7.67 (m, 2H), 7.55 (d, 1H), 7.41 (dd, 8.6 Hz, 1H), 7.26 (t, 1H), 7.21-7.22 (m, 1H), 7.18-7.19 (m, 1H), 4.34-4.38 (m, 1H), 2.64-2.74 (m, 2H), 2.60 (d, 3H), 2.40-2.52 (m, 1H), 2.26-2.31 (m, 1H)

Example 74: Preparation of 2-((2-chloro-5-(trifluoromethyl)phenyl)sulfonyl)-1-(2-fluorophenyl)-N-methyl-2,4,5,6-tetrahydrocyclopenta[c]pyrrol-4-amine

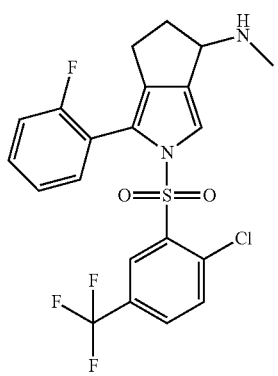 [SMILES: CNC1CCc2c1cn(S(=O)(=O)c1cc(C(F)(F)F)ccc1Cl)c2-c1ccccc1F]

¹H NMR (500 MHz, CD₃OD): 7.89 (d, 1H), 7.77 (d, 1H), 7.67 (s, 1H), 7.46 (s, 1H), 7.32-7.36 (m, 1H), 7.07-7.14 (m, 2H), 6.84 (t, 1H), 4.31-4.33 (m, 1H), 2.61-2.72 (m, 2H), 2.59 (s, 3H), 2.41-2.45 (m, 1H), 2.27-2.32 (m, 1H)

Example 75: Preparation of 2-((2,6-dichlorophenyl)sulfonyl)-1-(2-fluorophenyl)-N-methyl-2,4,5,6-tetrahydrocyclopenta[c]pyrrol-4-amine

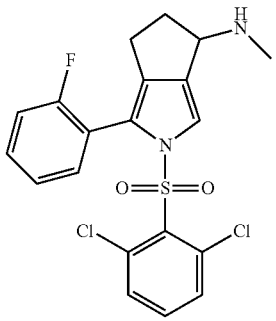 [SMILES: CNC1CCc2c1cn(S(=O)(=O)c1c(Cl)cccc1Cl)c2-c1ccccc1F]

¹H NMR (500 MHz, CD₃OD): 7.54 (s, 1H), 7.41-7.44 (m, 1H), 7.36-7.38 (m, 2H), 7.28-7.32 (m, 1H), 7.01-7.08 (m, 2H), 6.86 (t, 1H), 4.16-4.18 (m, 1H), 2.55-2.65 (m, 2H), 2.50 (s, 3H), 2.37-2.42 (m, 1H), 2.16-2.20 (m, 1H)

Example 76: Preparation of 2-((3,4-dichlorophenyl)sulfonyl)-1-(2-fluorophenyl)-N-methyl-2,4,5,6-tetrahydrocyclopenta[c]pyrrol-4-amine

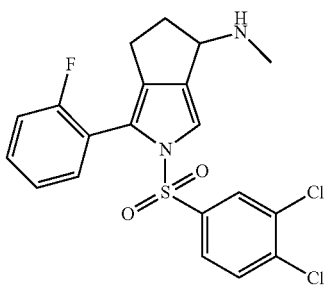 [SMILES: CNC1CCc2c1cn(S(=O)(=O)c1ccc(Cl)c(Cl)c1)c2-c1ccccc1F]

¹H NMR (500 MHz, CD₃OD): 7.74 (s, 1H), 7.46-7.48 (m, 1H), 7.42 (s, 1H), 7.32 (s, 2H), 7.20-7.23 (m, 2H), 7.12 (t, 1H), 4.08-4.10 (m, 1H), 2.55-2.62 (m, 2H), 2.46 (s, 3H), 2.36-2.42 (m, 1H), 2.10-2.16 (m, 1H)

Example 77: Preparation of 2-((3,5-dichlorophenyl)sulfonyl)-1-(2-fluorophenyl)-N-methyl-2,4,5,6-tetrahydrocyclopenta[c]pyrrol-4-amine

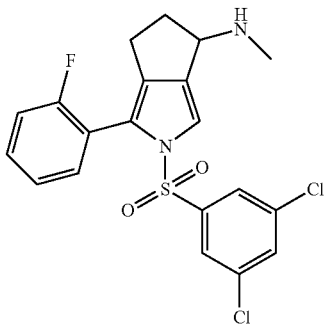 [SMILES: CNC1CCc2c1cn(S(=O)(=O)c1cc(Cl)cc(Cl)c1)c2-c1ccccc1F]

¹H NMR (500 MHz, CD₃OD): 7.63 (d, 2H), 7.11 (t, 1H), 4.05-4.07 (m, 1H), 2.53-2.63 (m, 2H), 2.45 (s, 3H), 2.34-2.41 (m, 1H), 2.08-2.14 (m, 1H)

Example 78: Preparation of 2-((3,5-dichlorophenyl)sulfonyl)-1-(2-fluoro-4-methylphenyl)-N-methyl-2,4,5,6-tetrahydrocyclopenta[c]pyrrol-4-amine

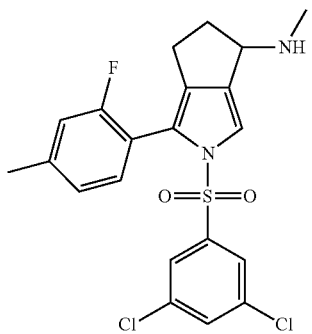

¹H NMR (500 MHz, CD₃OD): 7.75 (s, 1H), 7.53 (s, 1H), 7.30 (d, 2H), 7.04-7.10 (m, 2H), 6.93 (d, 1H), 4.29-4.31 (m, 1H), 2.55-2.70 (m, 5H), 2.40-2.47 (m, 4H), 2.21-2.29 (m, 1H)

Example 79: Preparation of 1-(2,5-dichlorophenyl)-2-((3,5-dichlorophenyl)sulfonyl)-N-methyl-2,4,5,6-tetrahydrocyclopenta[c]pyrrol-4-amine

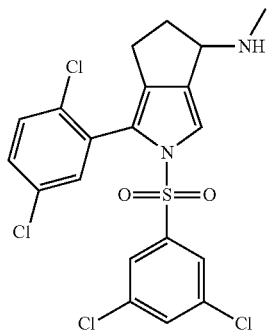 [SMILES: CNC1CCc2c1cn(S(=O)(=O)c1cc(Cl)cc(Cl)c1)c2-c1cc(Cl)ccc1Cl]

¹H NMR (500 MHz, CD₃OD): 7.78 (s, 1H), 7.55 (d, 1H), 7.46-7.48 (m, 1H), 7.41-7.44 (m, 1H), 7.39 (d, 2H), 7.31 (d, 1H), 4.26-4.30 (m, 1H), 2.62-2.70 (m, 2H), 2.58 (d, 3H), 2.45-2.54 (m, 1H), 2.20-2.25 (m, 1H)

Example 80: Preparation of 1-(2-fluorophenyl)-N-methyl-2-((2,3,4-trichlorophenyl)sulfonyl)-2,4,5,6-tetrahydrocyclopenta[c]pyrrol-4-amine

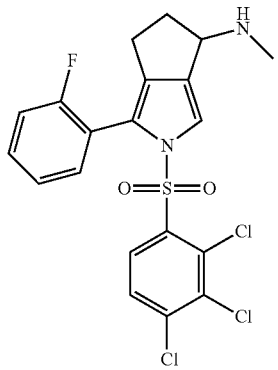 [SMILES: CNC1CCc2c1cn(S(=O)(=O)c1ccc(Cl)c(Cl)c1Cl)c2-c1ccccc1F]

¹H NMR (500 MHz, CD₃OD): 7.56 (s, 1H), 7.34-7.39 (m, 2H), 7.14-7.19 (m, 2H), 7.09-7.12 (m, 1H), 6.88 (t, 1H), 4.19-4.21 (m, 1H), 2.57-2.67 (m, 2H), 2.52 (s, 3H), 2.39-2.44 (m, 1H), 2.18-2.23 (m, 1H)

Example 81: Preparation of N-methyl-1-phenyl-2-((2,4,5-trichlorophenyl)sulfonyl)-2,4,5,6-tetrahydrocyclopenta[c]pyrrol-4-amine

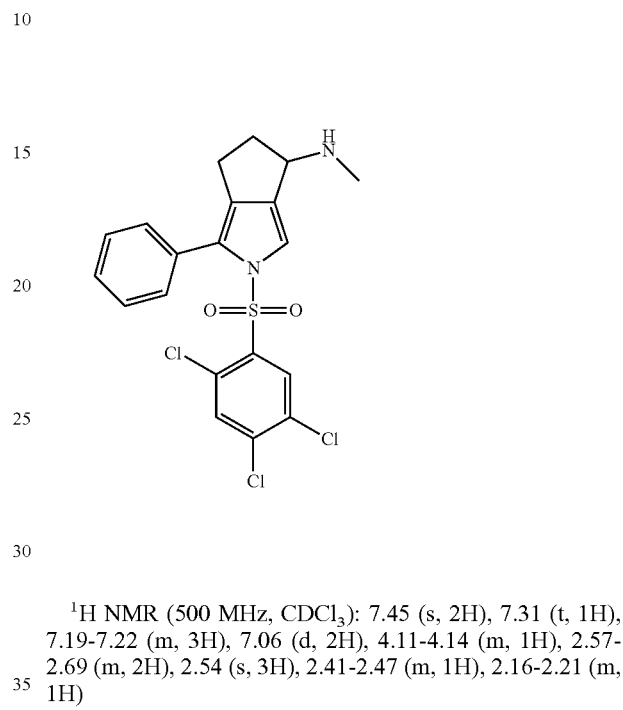

¹H NMR (500 MHz, CDCl₃): 7.45 (s, 2H), 7.31 (t, 1H), 7.19-7.22 (m, 3H), 7.06 (d, 2H), 4.11-4.14 (m, 1H), 2.57-2.69 (m, 2H), 2.54 (s, 3H), 2.41-2.47 (m, 1H), 2.16-2.21 (m, 1H)

Example 82: Preparation of 1-(2-fluoro-4-methylphenyl)-N-methyl-2-((2,4,5-trichlorophenyl)sulfonyl)-2,4,5,6-tetrahydrocyclopenta[c]pyrrol-4-amine

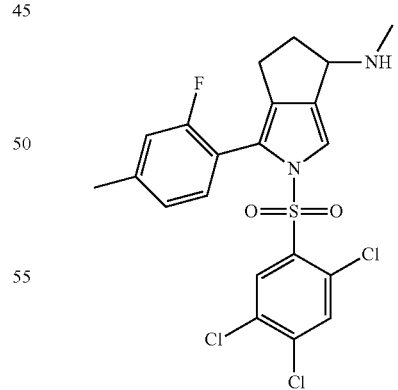

¹H NMR (500 MHz, CD₃OD): 7.80 (s, 1H), 7.57 (s, 1H), 7.25 (s, 1H), 7.01 (t, 1H), 6.95 (d, 1H), 6.72 (d, 1H), 4.22-4.24 (m, 1H), 2.55-2.67 (m, 2H), 2.54 (s, 3H), 2.39-2.44 (m, 1H), 2.37 (s, 3H), 2.20-2.25 (m, 1H)

Example 83: Preparation of 1-(2,5-dichlorophenyl)-N-methyl-2-((2,4,5-trichlorophenyl)sulfonyl)-2,4,5,6-tetrahydrocyclopenta[c]pyrrol-4-amine

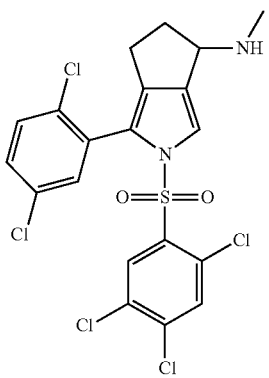 [SMILES: CNC1CCc2c1cn(S(=O)(=O)c1cc(Cl)c(Cl)cc1Cl)c2-c1cc(Cl)ccc1Cl]

¹H NMR (500 MHz, CD₃OD): 7.84 (s, 1H), 7.54 (d, 1H), 7.40 (dd, 1H), 7.26-7.29 (m, 2H), 7.19-7.20 (m, 1H), 4.14-4.18 (m, 1H), 2.59-2.66 (m, 2H), 2.49 (d, 3H), 2.36-2.44 (m, 1H), 2.15-2.21 (m, 1H)

Example 84: Preparation of 1-(2-fluorophenyl)-N-methyl-2-((2,4,5-trichlorophenyl)sulfonyl)-2,4,5,6-tetrahydrocyclopenta[c]pyrrol-4-amine

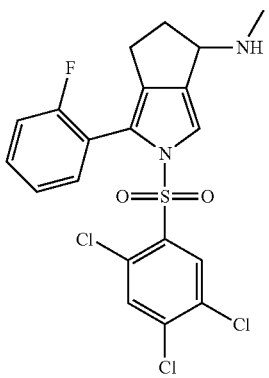 [SMILES: CNC1CCc2c1cn(S(=O)(=O)c1cc(Cl)c(Cl)cc1Cl)c2-c1ccccc1F]

¹H NMR (500 MHz, CD₃OD): 7.83 (s, 1H), 7.60 (s, 1H), 7.40-7.44 (m, 1H), 7.26 (s, 1H), 7.12-7.17 (m, 2H), 6.92 (t, 1H), 4.26-4.28 (m, 1H), 2.59-2.71 (m, 2H), 2.57 (s, 3H), 2.41-2.47 (m, 1H), 2.22-2.27 (m, 1H)

Example 85: Preparation of 1-(2-fluorophenyl)-N-methyl-2-((2,4,6-trichlorophenyl)sulfonyl)-2,4,5,6-tetrahydrocyclopenta[c]pyrrol-4-amine

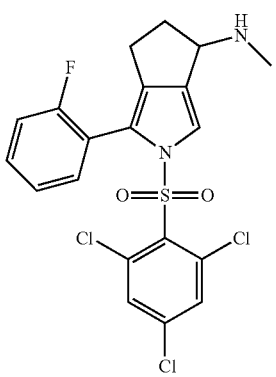 [SMILES: CNC1CCc2c1cn(S(=O)(=O)c1c(Cl)cc(Cl)cc1Cl)c2-c1ccccc1F]

¹H NMR (500 MHz, CD₃OD): 7.55 (s, 1H), 7.50 (s, 2H), 7.32-7.37 (m, 1H), 7.12-7.15 (m, 1H), 7.06-7.09 (m, 1H), 6.91 (t, 1H), 4.18-4.20 (m, 1H), 2.56-2.67 (m, 2H), 2.51 (s, 3H), 2.38-2.44 (m, 1H), 2.17-2.23 (m, 1H)

Example 86: Preparation of 2-((2,6-dichloro-4-(trifluoromethyl)phenyl)sulfonyl)-1-(2-fluorophenyl)-N-methyl-2,4,5,6-tetrahydrocyclopenta[c]pyrrol-4-amine

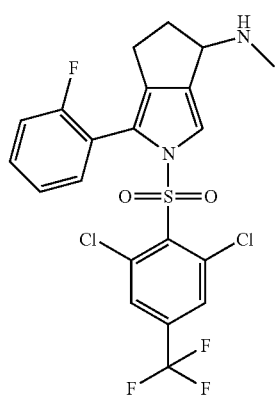 [SMILES: CNC1CCc2c1cn(S(=O)(=O)c1c(Cl)cc(C(F)(F)F)cc1Cl)c2-c1ccccc1F]

¹H NMR (500 MHz, CD₃OD): 7.74 (s, 2H), 7.64 (s, 1H), 7.32-7.37 (m, 1H), 7.15 (t, 1H), 7.06 (t, 1H), 6.84 (t, 1H), 4.28-4.30 (m, 1H), 2.59-2.70 (m, 2H), 2.57 (s, 3H), 2.41-2.46 (m, 1H), 2.25-2.30 (m, 1H)

Example 87: Preparation of 1-(2-fluorophenyl)-N-methyl-2-(thiophen-2-ylsulfonyl)-2,4,5,6-tetrahydrocyclopenta[c]pyrrol-4-amine

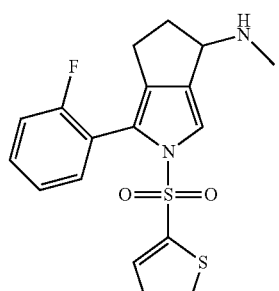

¹H NMR (500 MHz, CD₃OD): 7.81 (dd, 1H), 7.39-7.44 (m, 2H), 7.21-7.25 (m, 2H), 7.17 (t, 1H), 7.09 (t, 1H), 7.02 (t, 1H), 4.14-4.16 (m, 1H), 2.57-2.63 (m, 2H), 2.50 (s, 3H), 2.39-2.45 (m, 1H), 2.15-2.18 (m, 1H)

Example 88: Preparation of 1-(2-fluorophenyl)-N-methyl-2-(pyridin-3-ylsulfonyl)-2,4,5,6-tetrahydrocyclopenta[c]pyrrol-4-amine

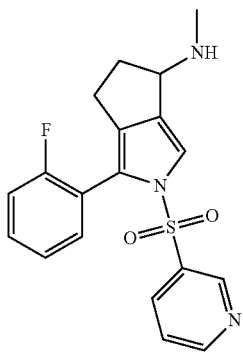 [SMILES: CNC1CCc2c1cn(S(=O)(=O)c1cccnc1)c2-c1ccccc1F]

$^1$H NMR (500 MHz, CD$_3$OD): 8.75 (d, 1H), 8.52 (d, 1H), 7.86 (dd, 1H), 7.49-7.52 (m, 1H), 7.43-7.47 (m, 2H), 7.19-7.22 (m, 2H), 7.10 (t, 1H), 4.11-4.12 (m, 1H), 2.54-2.61 (m, 2H), 2.49 (s, 3H), 2.37-2.43 (m, 1H), 2.11-2.17 (m, 1H)

Example 89: Preparation of 1-(2-chlorophenyl)-N-methyl-2-(pyridin-3-ylsulfonyl)-2,4,5,6-tetrahydrocyclopenta[c]pyrrol-4-amine

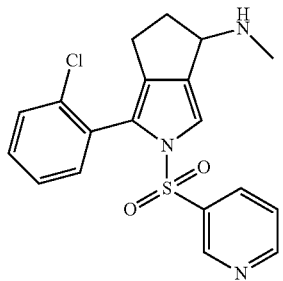 [SMILES: CNC1CCc2c1cn(S(=O)(=O)c1cccnc1)c2-c1ccccc1Cl]

$^1$H NMR (500 MHz, CD$_3$OD): 8.74 (d, 1H), 8.50 (dd, 1H), 7.86 (d, 1H), 7.49-7.51 (m, 1H), 7.45 (d, 1H), 7.28-7.42 (m, 4H), 4.07-4.10 (m, 1H), 2.54-2.66 (m, 1H), 2.36-2.51 (m, 4H), 2.27-2.34 (m, 1H), 2.10-2.12 (m, 1H)

Example 90: Preparation of 1-(2-fluoro-4-methylphenyl)-N-methyl-2-(pyridin-3-ylsulfonyl)-2,4,5,6-tetrahydrocyclopenta[c]pyrrol-4-amine

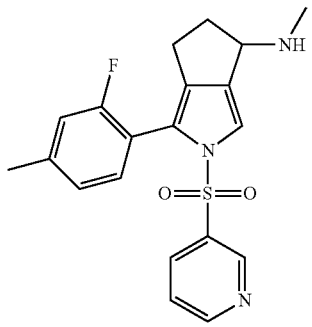

$^1$H NMR (500 MHz, CD$_3$OD): 8.73 (dd, 1H), 8.50 (d, 1H), 7.84-7.87 (m, 1H), 7.41-7.51 (m, 1H), 7.41 (s, 1H), 7.00-7.07 (m, 2H), 6.92 (d, 1H), 4.03-4.05 (m, 1H), 2.51-2.58 (m, 2H), 2.44 (s, 3H), 2.40 (s, 3H), 2.27-2.37 (m, 1H), 2.06-2.12 (m, 1H)

Example 91: Preparation of 1-(4-chloro-2-fluorophenyl)-N-methyl-2-(pyridin-3-ylsulfonyl)-2,4,5,6-tetrahydrocyclopenta[c]pyrrol-4-amine

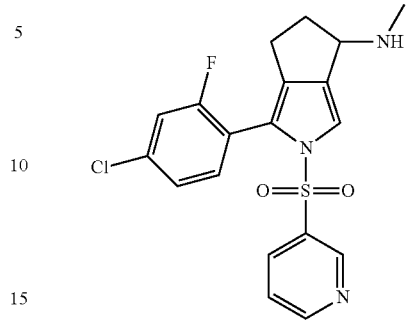

$^1$H NMR (500 MHz, CDCl$_3$): 8.75 (dd, 1H), 8.64 (d, 1H), 7.70 (d, 1H), 7.32-7.35 (m, 1H), 7.28 (s, 1H), 7.22 (t, 1H), 7.17 (dd, 1H), 7.10 (dd, 1H), 3.98-4.01 (m, 1H), 2.49-2.57 (m, 2H), 2.48 (s, 3H), 2.34-2.37 (m, 1H), 2.01-2.05 (m, 1H)

Example 92: Preparation of 1-(2,5-dichlorophenyl)-N-methyl-2-(pyridin-3-ylsulfonyl)-2,4,5,6-tetrahydrocyclopenta[c]pyrrol-4-amine

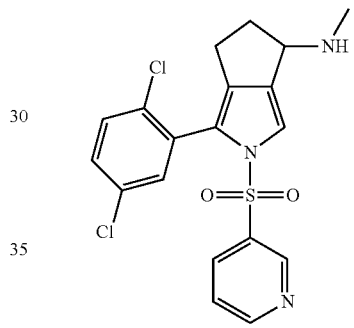

$^1$H NMR (500 MHz, CD$_3$OD): 8.79 (dd, 1H), 8.58 (dd, 1H), 7.90-7.91 (m, 1H), 7.62 (d, 1H), 7.53-7.56 (m, 1H), 7.38-7.46 (m, 2H), 7.26-7.28 (m, 1H), 4.35-4.37 (m, 1H), 2.66-2.71 (m, 1H), 2.63 (d, 3H), 2.38-2.60 (m, 2H), 2.25-2.30 (m, 1H)

Example 93: Preparation of 1-(5-chloro-2-fluoro-3-methylphenyl)-N-methyl-2-(pyridin-3-ylsulfonyl)-2,4,5,6-tetrahydrocyclopenta[c]pyrrol-4-amine

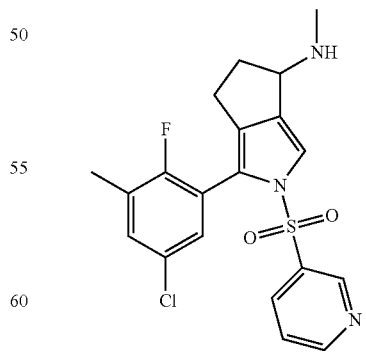

$^1$H NMR (500 MHz, CDCl$_3$): 8.77 (d, 1H), 8.66 (s, 1H), 7.73 (d, 1H), 7.34-7.36 (m, 2H), 7.19-7.21 (m, 1H), 6.97 (br, 1H), 4.10 (br, 1H), 2.56-2.61 (m, 2H), 2.51 (s, 3H), 2.37-2.43 (m, 1H), 2.23 (s, 3H), 2.15 (br, 1H)

Example 94: Preparation of N-methyl-2-(pyridin-3-ylsulfonyl)-1-(thiophen-3-yl)-2,4,5,6-tetrahydrocyclopenta[c]pyrrol-4-amine

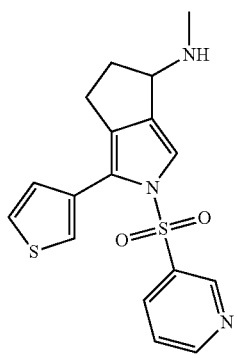 [SMILES: CNC1CCc2c1cn(S(=O)(=O)c1cccnc1)c2-c1ccsc1]

¹H NMR (500 MHz, CDCl₃): 8.70 (d, 1H), 8.58 (s, 1H), 7.62 (d, 1H), 7.26-7.30 (m, 3H), 7.15 (s, 1H), 7.04 (d, 1H), 4.04 (br, 1H), 2.53-2.64 (m, 2H), 2.51 (s, 3H), 2.41-2.46 (m, 2H)

Example 95: Preparation of 2-((5-chloropyridin-3-yl)sulfonyl)-1-(2-fluorophenyl)-N-methyl-2,4,5,6-tetrahydrocyclopenta[c]pyrrol-4-amine

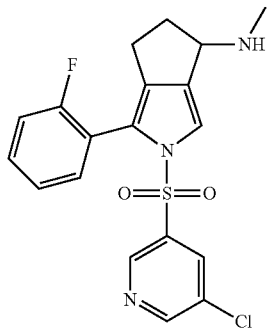 [SMILES: CNC1CCc2c1cn(S(=O)(=O)c1cncc(Cl)c1)c2-c1ccccc1F]

¹H NMR (500 MHz, CD₃OD): 8.79 (d, 1H), 8.49 (d, 1H), 7.79 (s, 1H), 7.55 (s, 1H), 7.46-7.51 (m, 1H), 7.20-7.24 (m, 2H), 7.12-7.14 (m, 1H), 4.24-4.25 (m, 1H), 2.59-2.66 (m, 2H), 2.57 (s, 3H), 2.41-2.46 (m, 1H), 2.19-2.24 (m, 1H)

Example 96: Preparation of 1-(2-fluorophenyl)-N-methyl-2-((6-phenoxypyridin-3-yl)sulfonyl)-2,4,5,6-tetrahydrocyclopenta[c]pyrrol-4-amine

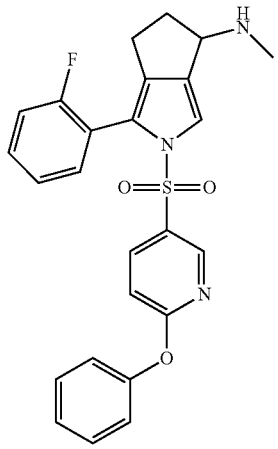 [SMILES: CNC1CCc2c1cn(S(=O)(=O)c1ccc(Oc3ccccc3)nc1)c2-c1ccccc1F]

¹H NMR (500 MHz, CD₃OD): 8.04 (d, 1H), 7.78 (dd, 1H), 7.39-7.45 (m, 4H), 7.22-7.28 (m, 2H), 7.16-7.19 (m, 1H), 7.07-7.10 (m, 3H), 6.96 (d, 1H), 4.08-4.10 (m, 1H), 2.55-2.61 (m, 2H), 2.47 (s, 3H), 2.38-2.43 (m, 1H), 2.10-2.16 (m, 1H)

Example 97: Preparation of 1-(2-fluorophenyl)-N-methyl-2-((3-methylisoxazolo[5,4-b]pyridin-5-yl)sulfonyl-)2,4,5,6-tetrahydrocyclopenta[c]pyrrol-4-amine

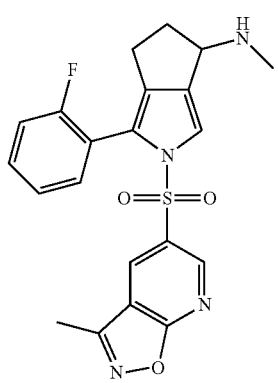 [SMILES: CNC1CCc2c1cn(S(=O)(=O)c1cnc3onc(C)c3c1)c2-c1ccccc1F]

¹H NMR (500 MHz, CD₃OD): 7.39-7.50 (m, 2H), 7.34-7.37 (m, 2H), 7.16-7.21 (m, 1H), 7.09 (t, 1H), 6.3 (s, 1H), 4.20-4.22 (m, 1H), 2.61-2.71 (m, 3H), 2.54 (s, 3H), 2.19-2.24 (m, 1H), 2.07 (s, 3H)

Example 98: Preparation of 2-((2-chloro-6-methoxypyridin-3-yl)sulfonyl)-1-(2-fluorophenyl)-N-methyl-2,4,5,6-tetrahydrocyclopenta[c]pyrrol-4-amine

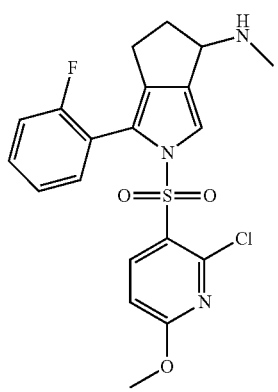 [SMILES: CNC1CCc2c1cn(S(=O)(=O)c1ccc(OC)nc1Cl)c2-c1ccccc1F]

¹H NMR (500 MHz, CD₃OD): 7.62 (s, 1H), 7.34-7.41 (m, 2H), 7.15-7.19 (m, 1H), 7.10-7.13 (m, 1H), 6.92 (t, 1H), 6.53 (t, 1H), 4.32-4.34 (m, 1H), 3.96 (s, 3H), 2.63-2.73 (m, 2H), 2.60 (s, 3H), 2.42-2.48 (m, 1H), 2.26-2.30 (m, 1H)

Example 99: Preparation of 2-((2-chloro-6-methyl-pyridin-3-yl)sulfonyl)-1-(2-fluorophenyl)-N-methyl-2,4,5,6-tetrahydrocyclopenta[c]pyrrol-4-amine

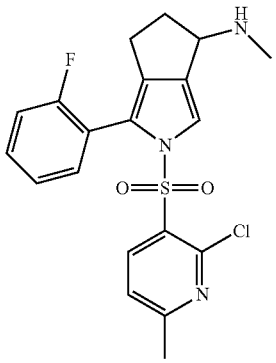 [SMILES: CNC1CCc2c1cn(S(=O)(=O)c1ccc(C)nc1Cl)c2-c1ccccc1F]

¹H NMR (500 MHz, CD₃OD): 7.58 (s, 1H), 7.45 (d, 1H), 7.34-7.37 (m, 1H), 7.08-7.16 (m, 3H), 6.90 (t, 1H), 4.22-4.24 (m, 1H), 2.58-2.68 (m, 2H), 2.54 (s, 3H), 2.52 (s, 3H), 2.40-2.46 (m, 1H), 2.20-2.24 (m, 1H)

Example 100: Preparation of 2-((2-chloro-5-methyl-pyridin-3-yl)sulfonyl)-1-(2-fluorophenyl)-N-methyl-2,4,5,6-tetrahydrocyclopenta[c]pyrrol-4-amine

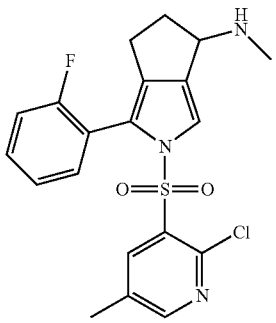 [SMILES: CNC1CCc2c1cn(S(=O)(=O)c1cc(C)cnc1Cl)c2-c1ccccc1F]

¹H NMR (500 MHz, CDCl₃): 8.25 (s, 1H), 7.59 (s, 1H), 7.26-7.30 (m, 2H), 7.17-7.18 (m, 1H), 7.04-7.07 (m, 1H), 6.81-6.85 (m, 1H), 4.27 (br, 1H), 2.57-2.67 (m, 5H), 2.37-2.41 (m, 1H), 2.28 (br, 1H), 2.12 (s, 3H)

Example 101: Preparation of 1-(2-fluorophenyl)-N-methyl-2-((1-methyl-1H-imidazol-2-yl)sulfonyl)-2,4,5,6-tetrahydrocyclopenta[c]pyrrol-4-amine

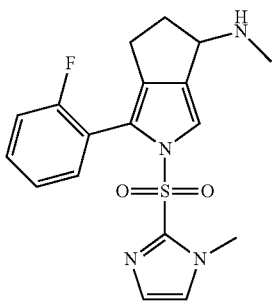 [SMILES: CNC1CCc2c1cn(S(=O)(=O)c1nccn1C)c2-c1ccccc1F]

¹H NMR (500 MHz, CDCl₃): 7.45 (s, 1H), 7.30-7.34 (m, 1H), 7.06-7.11 (m, 2H), 7.01-7.04 (m, 2H), 6.84 (s, 1H), 4.17 (br, 1H), 3.42 (s, 3H), 2.51-2.63 (m, 5H), 2.37-2.44 (m, 2H)

Example 102: Preparation of 2-((1,3-dimethyl-1H-pyrazolo[3,4-b]pyridin-5-yl)sulfonyl)-1-(2-fluorophenyl)-N-methyl-2,4,5,6-tetrahydrocyclopenta[c]pyrrol-4-amine

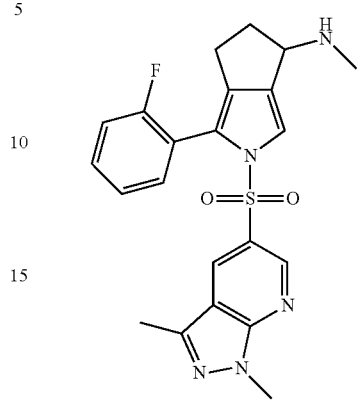

¹H NMR (500 MHz, CDCl₃): 7.36-7.41 (m, 1H), 7.28-7.32 (m, 1H), 7.22 (s, 1H), 7.15-7.19 (m, 1H), 7.09-7.12 (m, 1H), 7.01-7.04 (m, 1H), 6.43 (s, 1H), 4.06-4.08 (m, 1H), 3.46-3.53 (m, 3H), 3.18-3.26 (m, 2H), 2.55-2.65 (m, 2H), 2.51 (s, 3H), 2.03 (s, 3H)

Example 103: Preparation of N-ethyl-1-(2-fluorophenyl)-2-(pyridin-3-ylsulfonyl)-2,4,5,6-tetrahydrocyclopenta[c]pyrrol-4-amine Step 1: Preparation of 1-bromo-2-(pyridin-3-ylsulfonyl)-5,6-dihydrocyclopenta[c]pyrrol-4(2H)-one

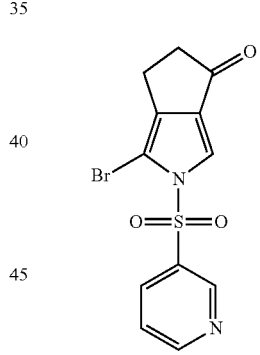

1-bromo-5,6-dihydrocyclopenta[c]pyrrol-4(2H)-one (500 mg, 2.5 mmole) prepared in the step 1 of Example 1 was dissolved in a N,N-dimethylformamide solution (20 ml), the solution was cooled to 0° C., and sodium hydride (60% in oil) (200 mg, 4.9 mmole) was added dropwise. The reaction mixture was stirred at 0° C. for 30 minutes, and then, pyridin-3-sulfonyl chloride (665 mg, 3.8 mmole) was put, and the mixture was stirred at 0° C. for 1 hour. In the reaction mixture, water was introduced, the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:2 (v/v)) to obtain 600 mg of the title compound 600 mg (yield 70%).

¹H NMR (500 MHz, CDCl₃): 8.80 (d, 2H), 8.43 (d, 1H), 7.85 (s, 1H), 7.69 (t, 1H), 3.00-3.03 (m, 2H), 2.52-2.60 (m, 2H)

Step 2: Preparation of 1-(2-fluorophenyl)-2-(pyridin-3-ylsulfonyl)-5,6-dihydrocyclopenta[c]pyrrol-4(2H)-one

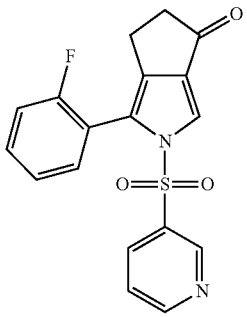 [SMILES: O=C1CCc2c1cn(S(=O)(=O)c1cccnc1)c2-c1ccccc1F]

1-bromo-2-(pyridin-3-ylsulfonyl)-5,6-dihydrocyclopenta[c]pyrrol-4(2H)-one (600 mg, 1.8 mmole) prepared in the step 1, 1,1'-bis(diphenylphosphino)ferrocene-palladium(II) dichloride dichloromethane complex (215 mg, 0.3 mmole), 2-fluorophenyl boric acid (369 mg, 2.6 mmole) were suspended in a mixture of 1,2-dimethoxyethane (9 ml) and 2M sodium carbonate (3 ml), and the mixture was reacted in a microwave reactor (120° C., 5 minutes). The reaction mixture was filtered through Celite, water was added to the filtrate, and the mixture was extracted with ethyl acetate. The extract was washed with saturated brine, dried over anhydrous magnesium sulfate, and concentrated under reduced pressure. The obtained residue was purified with silica gel column chromatography (ethyl acetate:n-hexane=1:1 (v/v)) to prepare 300 mg of the title compound (yield 47.8%).

$^1$H NMR (500 MHz, CDCl$_3$): 8.79 (d, 1H), 8.53 (s, 1H), 7.87 (s, 1H), 7.68 (d, 1H), 7.43-7.47 (m, 1H), 7.33-7.36 (m, 1H), 7.28-7.31 (m, 1H), 7.21 (t, 1H), 7.02 (t, 1H), 2.84-2.86 (m, 2H), 2.70-2.72 (m, 2H)

Step 3: Preparation of N-ethyl-1-(2-fluorophenyl)-2-(pyridin-3-ylsulfonyl)-2,4,5,6-tetrahydrocyclopenta[c]pyrrol-4-amine

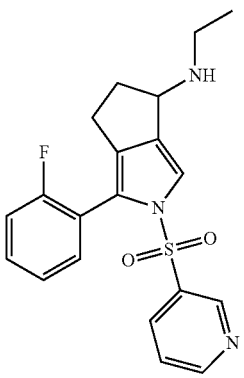 [SMILES: CCNC1CCc2c1cn(S(=O)(=O)c1cccnc1)c2-c1ccccc1F]

To a solution of 1-(2-fluorophenyl)-2-(pyridin-3-ylsulfonyl)-5,6-dihydrocyclopenta[c]pyrrol-4(2H)-one (30 mg, 0.08 mmole) prepared in the step 2 in methanol (1 ml), tetraisopropoxytitanium(IV) (119 mg, 0.4 mmole) and a 2M ethylamine-tetrahydrofurane solution (0.21 ml, 0.4 mmole) were added, and the mixture was stirred at room temperature for 4 hours. Sodium borohydride (16 mg, 0.4 mmole) was put, and the mixture was stirred at room temperature for 1 hour, and then, the reaction mixture was concentrated under reduced pressure. Sodium bicarbonate was added, and the mixture was extracted with ethyl acetate. The extract was washed with saturated brine, dried over anhydrous magnesium sulfate, and concentrated under reduced pressure. The obtained residue was purified with silica gel column chromatography (methanol:ethyl acetate=1:5 (v/v)) to prepared 15 mg of the title compound 15 mg (yield 46%).

$^1$H NMR (500 MHz, CD$_3$OD): 8.75 (dd, 1H), 8.52 (d, 1H), 7.86 (dd, 1H), 7.49-7.52 (m, 1H), 7.43-7.46 (m, 2H), 7.19-7.23 (m, 2H), 7.10 (t, 1H), 4.19-4.22 (m, 1H), 2.82-2.89 (m, 1H), 2.75-2.79 (m, 1H), 2.55-2.62 (m, 2H), 2.12-2.16 (m, 1H), 1.20 (t, 1H)

Example 104: Preparation of 1-(2-fluorophenyl)-N-isopropyl-2-(pyridin-3-ylsulfonyl)-2,4,5,6-tetrahydrocyclopenta[c]pyrrol-4-amine

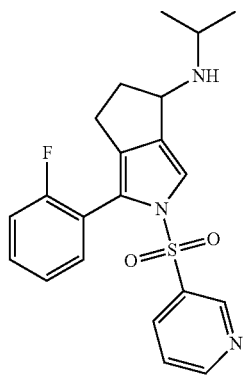 [SMILES: CC(C)NC1CCc2c1cn(S(=O)(=O)c1cccnc1)c2-c1ccccc1F]

To a solution of 1-(2-fluorophenyl)-2-(pyridin-3-ylsulfonyl)-5,6-dihydrocyclopenta[c]pyrrol-4(2H)-one (30 mg, 0.08 mmole) prepared in the step 2 of Example 103 in methanol (1 ml), tetraisopropoxytitanium(IV)(119 mg, 0.4 mmole) and isopropylamine (25 mg, 0.4 mmole) were added, and the mixture was stirred at room temperature for 4 hours. Sodium borohydride (16 mg, 0.4 mmole) was put, and the mixture was stirred at room temperature for 1 hours, and then, the reaction mixture was concentrated under reduced pressure. A saturated aqueous solution of sodium bicarbonate was added, and the mixture was extracted with ethyl acetate. The extract was washed with saturated brine, dried over anhydrous magnesium sulfate, and concentrated under reduced pressure. The obtained residue was purified with silica gel column chromatography (methanol:ethyl acetate=1:5 (v/v)) to prepare 15 mg of the title compound (yield 44.6%).

$^1$H NMR (500 MHz, CDCl$_3$): 7.74 (d, 1H), 8.60 (s, 1H), 7.68 (d, 1H), 7.35-7.39 (m, 1H), 7.28-7.32 (m, 3H), 7.16 (t, 1H), 7.03 (t, 1H), 4.23-4.24 (m, 1H), 3.02-3.07 (m, 1H), 2.51-2.63 (m, 2H), 2.34-2.40 (m, 1H), 2.04 (br, 1H), 1.17 (q, 6H)

Example 105: Preparation of 1-(2-fluorophenyl)-N,6,6-trimethyl-2-(pyridin-3-ylsulfonyl)-2,4,5,6-tetrahydrocyclopenta[c]pyrrol-4-amine Step 1: Preparation of 6,6-dimethyl-5,6-dihydrocyclopenta[c]pyrrol-4(2H)-one

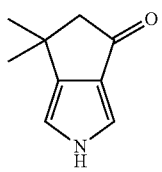

To a solution of 4,4-dimethyl-2-cyclopentene-1-one (1 g, 9.1 mmole) in tetrahydrofurane (10 ml), p-toluenesulfonylmethyl isocyanide (1.8 g, 9.1 mmole) was added, and the mixture was stirred at room temperature for 10 minutes, and then, a solution of potassium tert-butoxide (1 g, 10.9 mmole) in tetrahydrofurane (10 ml) was slowly added dropwise for 1 hour. In the reaction mixture, water was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:1 (v/v)) to prepare 310 mg of the title compound (yield 23%).

$^1$H NMR (500 MHz, CDCl$_3$): 8.78 (br, 1H), 7.06 (s, 1H), 6.61 (s, 1H), 2.83 (s, 2H), 1.39 (s, 6H)

Step 2: Preparation of 1-bromo-6,6-dimethyl-5,6-dihydrocyclopenta[c]pyrrol-4(2H)-one

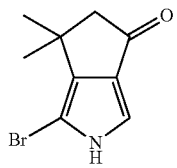

6,6-dimethyl-5,6-dihydrocyclopenta[c]pyrrol-4(2H)-one (300 mg, 2.0 mmole) prepared in the step 1 was dissolved in tetrahydrofurane (20 ml), and the mixture was cooled to −78° C. N-bromosuccinimide (375 mg, 2.1 mmole) was added thereto, and then, the mixture was stirred at room temperature for 1 hour. The reaction mixture was concentrated under reduced pressure, water was added to the residue, and the mixture was extracted with ethyl acetate. The separated organic layer was washed with saturated brine, dried over anhydrous magnesium sulfate, and concentrated under reduced pressure. The obtained residue was purified with silica gel column chromatography (ethyl acetate:n-hexane=1:2 (v/v)) to prepare 105 mg of the title compound (yield 23%).

$^1$H NMR (500 MHz, CDCl$_3$): 9.09 (br, 1H), 7.03 (s, 1H), 2.76 (s, 2H), 1.43 (s, 6H)

Step 3: Preparation of 1-(2-fluorophenyl)-6,6-dimethyl-5,6-dihydrocyclopenta[c]pyrrol-4(2H)-one

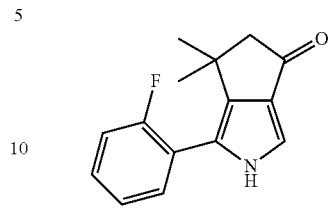

1-bromo-6,6-dimethyl-5,6-dihydrocyclopenta[c]pyrrol-4(2H)-one (100 mg, 0.4 mmole) prepared in the step 2, 1,1'-bis(diphenylphosphino)ferrocene-palladium(II)dichloride dichloromethane complex (53.7 mg, 0.06 mmole), and 2-fluorophenyl boric acid (91.5 mg, 0.6 mmole) were suspended in a mixture of 1,2-dimethoxyethane (4 ml) and 2M sodium carbonate (1 ml), and the mixture was reacted in a microwave reactor (120° C., 5 minutes). The reaction mixture was filtered through Celite, water was added to the filtrate, and the mixture was extracted with ethyl acetate. The extract was washed with saturated brine, dried over anhydrous magnesium sulfate, and concentrated under reduced pressure. The obtained residue was purified with silica gel column chromatography (ethyl acetate:n-hexane=1:2 (v/v)) to prepare 40 mg of the title compound (yield 37.5%).

$^1$H NMR (500 MHz, CDCl$_3$): 9.21 (br, 1H), 7.28-7.32 (m, 1H), 7.22 (t, 1H), 7.14-7.18 (m, 2H), 2.80 (s, 2H), 1.46 (s, 6H)

Step 4: Preparation of 1-(2-fluorophenyl)-6,6-dimethyl-2-(pyridin-3-ylsulfonyl)-5,6-dihydrocyclopenta[c]pyrrol-4(2H)-one

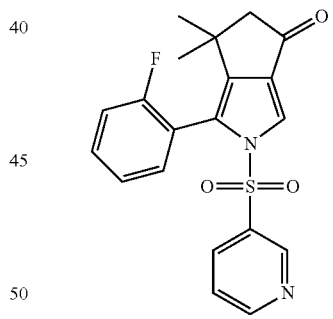

1-(2-fluorophenyl)-6,6-dimethyl-5,6-dihydrocyclopenta[c]pyrrol-4(2H)-one (35 mg, 0.1 mmole) prepared in the step 3 was dissolved in a N,N-dimethylformamide solution (3 ml), the mixture was cooled to 0° C., and sodium hydride (60% in oil)(8.6 mg, 0.2 mmole) was added dropwise. The reaction mixture was stirred at 0° C. for 30 minutes, pyridin-3-sulfonyl chloride (38.3 mg, 0.2 mmole) was put, and the mixture was stirred at 0° C. for 1 hour. In the reaction mixture, water was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:1 (v/v)) to prepare 40 mg of the title compound (yield 72%).

¹H NMR (500 MHz, CDCl₃): 8.83 (d, 1H), 8.56 (s, 1H), 7.82 (s, 1H), 7.75 (d, 1H), 7.46-7.49 (m, 1H), 7.37-7.40 (m, 1H), 7.13-7.20 (m, 2H), 7.00 (t, 1H), 2.71 (s, 2H), 1.15 (s, 3H), 1.11 (s, 3H)

Step 5: Preparation of 1-(2-fluorophenyl)-N,6,6-trimethyl-2-(pyridin-3-ylsulfonyl)-2,4,5,6-tetrahydrocyclopenta[c]pyrrol-4-amine

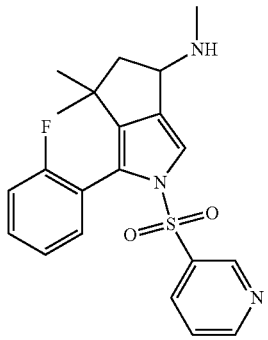 [SMILES: CNC1CC(C)(C)c2c1cn(S(=O)(=O)c1cccnc1)c2-c1ccccc1F]

To a solution of 1-(2-fluorophenyl)-6,6-dimethyl-2-(pyridin-3-ylsulfonyl)-5,6-dihydrocyclopenta[c]pyrrol-4(2H)-one (40 mg, 0.104 mmole) prepared in the step 4 in methanol (3 ml), tetraisopropoxytitanium(IV)(88.7 mg, 0.312 mmole) and a 2M methylamine-tetrahydrofurane solution (0.15 ml, 0.3 mmole) were added, and the mixture was stirred at room temperature for 4 hours. Sodium borohydride (31 mg, 0.8 mmole) was put, and the mixture was stirred at room temperature for 1 hour, and then, the reaction mixture was concentrated under reduced pressure. A saturated aqueous solution of sodium bicarbonate was added thereto, and then, the mixture was extracted with ethyl acetate. The extract was washed with saturated brine, dried over anhydrous magnesium sulfate, and concentrated under reduced pressure. The obtained residue was purified with silica gel column chromatography (methanol:ethyl acetate=1:5 (v/v)) to prepare 12 mg of the title compound (yield 29%).

¹H NMR (500 MHz, CDCl₃): 8.77 (d, 1H), 8.60-8.62 (m, 1H), 7.75 (t, 1H), 7.34-7.42 (m, 3H), 7.04-7.14 (m, 2H), 6.99 (t, 1H), 4.17-4.18 (m, 1H), 2.60 (d, 3H), 2.41-2.46 (m, 1H), 1.94-2.00 (m, 1H), 1.03 (d, 3H), 0.98 (d, 3H)

Example 106: Preparation of 2-((3-chlorophenyl)sulfonyl)-1-(2-fluorophenyl)-N,6,6-trimethyl-2,4,5,6-tetrahydrocyclopenta[c]pyrrol-4-amine

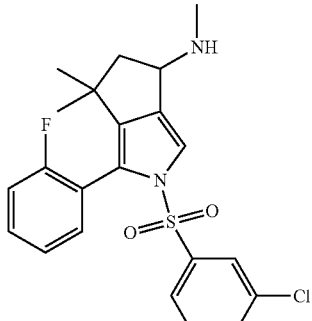

The title compound was prepared by the same method as Example 105, except that 3-chlorophenyl sulfonyl chloride was used instead of pyridin-3-sulfonyl chloride in the step 4 of Example 105.

¹H NMR (500 MHz, CD₃OD): 7.66 (d, 1H), 7.44-7.51 (m, 3H), 7.40 (dd, 1H), 7.34-7.35 (m, 1H), 7.15-7.19 (m, 1H), 7.07 (t, 1H), 7.00 (t, 1H), 4.21-4.23 (m, 1H), 2.55 (d, 3H), 2.42-2.47 (m, 1H), 1.94-1.99 (m, 1H), 0.95-1.06 (m, 6H)

Example 107: Preparation of 2-(3-chlorobenzyl)-1-(2-fluorophenyl)-N-methyl-2,4,5,6-tetrahydrocyclopenta[c]pyrrol-4-amine Step 1: Preparation of 1-(2-fluorophenyl)-5,6-dihydrocyclopenta[c]pyrrol-4(2H)-one

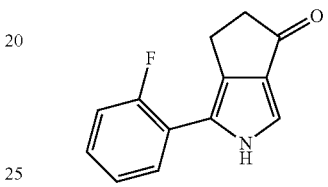

1-bromo-5,6-dihydrocyclopenta[c]pyrrol-4(2H)-one (600 mg, 2.9 mmole) prepared in the step 1 of Example 1, 1,1'-bis(diphenylphosphino)ferrocene-palladium(II)dichloride dichloromethane complex (367 mg, 0.5 mmole), and 2-fluorophenyl boric acid (629.5 mg, 4.5 mmole) were suspended in a mixture of 1,2-dimethoxyethane (18 ml) and 2M sodium carbonate (6 ml), and the mixture was reacted in a microwave reactor (120° C., 5 minutes). The reaction mixture was filtered through Celite, water was added to the filtrate, and the mixture was extracted with ethyl acetate. The extract was washed with saturated brine, dried over anhydrous magnesium sulfate, and concentrated under reduced pressure. The obtained residue was purified with silica gel column chromatography (ethyl acetate:n-hexane=1:2 (v/v)) to prepare 438 mg of the title compound (yield 68%).

¹H NMR (500 MHz, CDCl₃): 9.63 (br, 1H), 7.54-7.58 (m, 1H), 7.13-7.26 (m, 4H), 3.15-3.17 (m, 2H), 2.96-2.98 (m, 2H)

Step 2: Preparation of 2-(3-chlorobenzyl)-1-(2-fluorophenyl)-5,6-dihydrocyclopenta[c]pyrrol-4(2H)-one

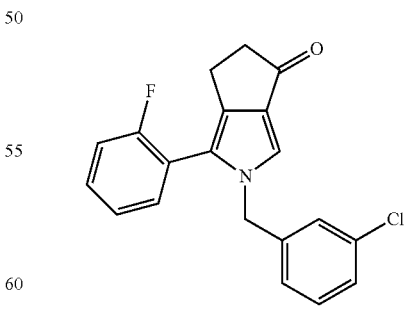

1-(2-fluorophenyl)-5,6-dihydrocyclopenta[c]pyrrol-4(2H)-one (30 mg, 0.1 mmole) prepared in the step 1 was dissolved in a N,N-dimethylformamide solution (2 ml), the mixture was cooled to 0° C., and sodium hydride (60% in oil)(8.4 mg, 0.2 mmole) was added dropwise. The reaction mixture was stirred at 0° C. for 30 minutes, and then, 3-chlorobenzylbromide (0.027 ml, 0.2 mmole) was put, and the mixture was stirred at room temperature for 3 hours. In the reaction mixture, water was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:2 (v/v)) to prepare 35 mg of the title compound (yield 74%).

$^1$H NMR (500 MHz, CDCl$_3$): 7.71-7.75 (m, 3H), 7.49 (t, 1H), 7.27-7.34 (m, 4H), 7.10 (t, 1H), 5.67 (s, 2H), 3.01-3.04 (m, 2H), 2.55-2.61 (m, 2H)

Step 3: Preparation of 2-(3-chlorobenzyl)-1-(2-fluorophenyl)-N-methyl-2,4,5,6-tetrahydrocyclopenta[c]pyrrol-4-amine

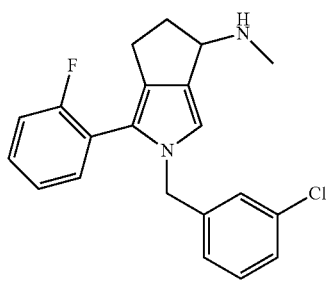 [SMILES: CNC1CCc2c1cn(Cc1cccc(Cl)c1)c2-c1ccccc1F]

To a solution of 2-(3-chlorobenzyl)-1-(2-fluorophenyl)-5,6-dihydrocyclopenta[c]pyrrol-4(2H)-one (35 mg, 0.1 mmole) prepared in the step 2 in methanol (1 ml), tetraisopropoxytitanium(IV)(146 mg, 0.5 mmole) and a 2M methylamine-tetrahydrofurane solution (0.25 ml, 0.5 mmole) were added, and the mixture was stirred at room temperature for 4 hours. Sodium borohydride (39 mg, 1.03 mmole) was put, and the mixture was stirred at room temperature for 1 hour, and then, the reaction mixture was concentrated under reduced pressure. A saturated aqueous solution of sodium bicarbonate was added thereto, and the mixture was extracted with ethyl acetate. The extract was washed with saturated brine, dried over anhydrous magnesium sulfate, and concentrated under reduced pressure. The obtained residue was purified with silica gel column chromatography (methanol:ethyl acetate=1:5 (v/v)) to prepare 10 mg of the title compound (yield 27%).

$^1$H NMR (500 MHz, CD$_3$OD): 7.29-7.32 (m, 1H), 7.20 (t, 1H), 7.19-7.15 (m, 4H), 6.88 (s, 1H), 6.83 (s, 1H), 6.79-6.80 (m, 1H), 5.04 (s, 2H), 4.21-4.23 (m, 1H), 2.73-2.78 (m, 1H), 2.66-2.71 (m, 1H), 2.54-2.59 (m, 1H), 2.52 (s, 3H), 2.22-2.27 (m, 1H)

In the Examples 108 to 112 below, title compounds were prepared by the same method as Example 107, except that reactants were appropriately changed considering the structure of the compounds to be prepared and the Reaction Scheme 1.

Example 108: Preparation of 2-(3-fluorobenzyl)-1-(2-fluorophenyl)-N-methyl-2,4,5,6-tetrahydrocyclopenta[c]pyrrol-4-amine

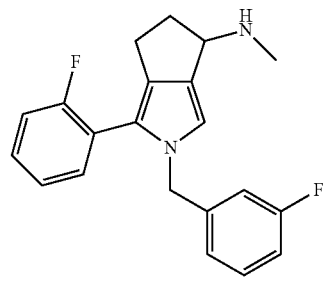 [SMILES: CNC1CCc2c1cn(Cc1cccc(F)c1)c2-c1ccccc1F]

$^1$H NMR (500 MHz, CD$_3$OD): 7.27-7.32 (m, 1H), 7.09-7.21 (m, 4H), 6.86 (t, 1H), 6.81 (s, 1H), 6.69 (d, 1H), 6.54 (d, 1H), 5.04 (s, 2H), 4.10-4.12 (m, 1H), 2.72-2.77 (m, 1H), 2.61-2.68 (m, 1H), 2.52-2.57 (m, 1H), 2.45 (s, 3H), 2.15-2.21 (m, 1H)

Example 109: Preparation of 2-benzyl-1-(2-fluorophenyl)-N-methyl-2,4,5,6-tetrahydrocyclopenta[c]pyrrol-4-amine

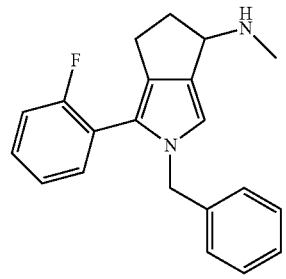 [SMILES: CNC1CCc2c1cn(Cc1ccccc1)c2-c1ccccc1F]

$^1$H NMR (500 MHz, CDCl$_3$): 7.16-7.23 (m, 5H), 7.06-7.10 (m, 2H), 6.96 (d, 2H), 6.67 (s, 1H), 4.96 (s, 2H), 4.19 (br, 1H), 2.72-2.78 (m, 1H), 2.62-2.69 (m, 1H), 2.53-2.59 (m, 1H), 2.47 (s, 3H), 2.22 (br, 1H)

Example 110: Preparation of 1-(2-fluorophenyl)-N-methyl-2-(3-methylbenzyl)-2,4,5,6-tetrahydrocyclopenta[c]pyrrol-4-amine

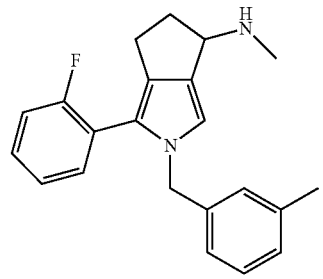 [SMILES: CNC1CCc2c1cn(Cc1cccc(C)c1)c2-c1ccccc1F]

$^1$H NMR (500 MHz, CD$_3$OD): 7.29-7.33 (m, 1H), 7.20 (t, 1H), 7.13 (t, 2H), 7.04 (t, 1H), 6.96 (d, 1H), 6.83 (s, 1H), 6.70 (s, 1H), 6.68 (d, 1H), 4.98 (s, 2H), 4.20-4.23 (m, 1H), 2.72-2.76 (m, 1H), 2.65-2.70 (m, 1H), 2.53-2.59 (m, 1H), 2.51 (s, 3H), 2.22-2.28 (m, 1H), 2.19 (s, 3H)

Example 111: Preparation of 1-(2-fluorophenyl)-2-(3-methoxybenzyl)-N-methyl-2,4,5,6-tetrahydrocyclopenta[c]pyrrol-4-amine

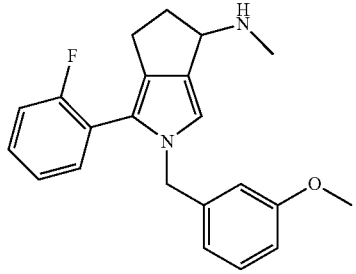 [SMILES: CNC1CCc2c1cn(Cc1cccc(OC)c1)c2-c1ccccc1F]

¹H NMR (500 MHz, CDCl₃): 7.18-7.25 (m, 2H), 7.06-7.14 (m, 3H), 6.70-6.71 (m, 2H), 6.55-6.56 (m, 1H), 6.47 (s, 1H), 4.93 (s, 2H), 4.26 (br, 1H), 3.69 (s, 3H), 2.71-2.77 (m, 1H), 2.61-2.68 (m, 1H), 2.52-2.58 (m, 1H), 2.47 (s, 3H), 2.25-2.29 (m, 1H)

Example 112: Preparation of 2-(3-chlorobenzyl)-1-(2-fluorophenyl)-N-methyl-2,4,5,6-tetrahydrocyclopenta[c]pyrrol-4-amine

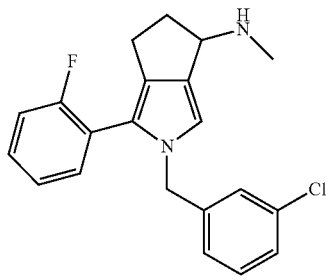 [SMILES: CNC1CCc2c1cn(Cc1cccc(Cl)c1)c2-c1ccccc1F]

¹H NMR (500 MHz, CD₃OD): 7.29-7.32 (m, 1H), 7.20 (t, 1H), 7.19-7.15 (m, 4H), 6.88 (s, 1H), 6.83 (s, 1H), 6.79-6.80 (m, 1H), 5.04 (s, 2H), 4.21-4.23 (m, 1H), 2.73-2.78 (m, 1H), 2.66-2.71 (m, 1H), 2.54-2.59 (m, 1H), 2.52 (s, 3H), 2.22-2.27 (m, 1H)

Example 113: Preparation of 1-(2,4-difluorophenyl)-2-((3-fluorophenyl)sulfonyl)-N-methyl-2,4,5,6-tetrahydrocyclopenta[c]pyrrol-4-amine Step 1: Preparation of 1-bromo-2-((3-fluorophenyl)sulfonyl)-5,6-dihydrocyclopenta[c]pyrrol-4(2H)-one

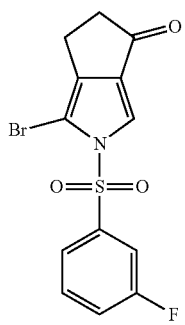 [SMILES: O=C1CCc2c1cn(S(=O)(=O)c1cccc(F)c1)c2Br]

1-bromo-5,6-dihydrocyclopenta[c]pyrrol-4(2H)-one (500 mg, 2.5 mmole) prepared in the step 1 of Example 1 was dissolved in a N,N-dimethylformamide solution (20 ml), the mixture was cooled to 0° C., and sodium hydride (60% in oil)(200 mg, 4.9 mmole) was added dropwise. The reaction mixture was stirred at 0° C. for 30 minutes, and then, 3-fluorobenzenesulfonyl chloride (730 mg, 3.8 mmole) was put, and the mixture was stirred at 0° C. for 1 hour. In the reaction mixture, water was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:2 (v/v)) to prepare 700 mg of the title compound (yield 78%).

¹H NMR (500 MHz, CDCl₃): 7.79-7.85 (m, 2H), 7.68 (t, 1H), 7.51-7.57 (m, 2H), 3.01-3.05 (m, 2H), 2.35-2.41 (m, 2H)

Step 2: Preparation of 1-(2,4-difluorophenyl)-2-((3-fluorophenyl)sulfonyl)-5,6-dihydrocyclopenta[c]pyrrol-4(2H)-one

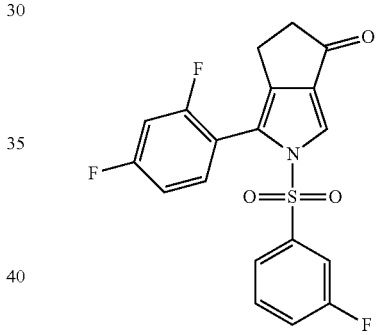

1-bromo-2-((3-fluorophenyl)sulfonyl)-5,6-dihydrocyclopenta[c]pyrrol-4(2H)-one (500 mg, 1.4 mmole) prepared in the step 1, 1,1'-bis(diphenylphosphino)ferrocene-palladium (II)dichloride dichloromethane complex (171 mg, 0.2 mmole), and 2-fluorophenyl boric acid (331 mg, 2.1 mmole) were suspended in a mixture of 1,2-dimethoxyethane (9 ml) and 2M sodium carbonate (3 ml), the mixture was reacted in a microwave reactor (120° C., 5 minutes). The reaction mixture was filtered through Celite, water was added to the filtrated, and the mixture was extracted with ethyl acetate. The extract was washed with saturated brine, dried over anhydrous magnesium sulfate, and concentrated under reduced pressure. The obtained residue was purified with silica gel column chromatography (ethyl acetate:n-hexane=1:2 (v/v)) to prepare 350 mg of the title compound (yield 64%).

¹H NMR (500 MHz, CDCl₃): 7.68-7.85 (m, 4H), 7.51-7.57 (m, 2H), 7.08 (d, 1H), 6.87 (d, 1H), 3.05-3.09 (m, 2H), 2.41-2.49 (m, 2H)

Step 3: Preparation of 1-(2,4-difluorophenyl)-2-((3-fluorophenyl)sulfonyl)-N-methyl-2,4,5,6-tetrahydrocyclopenta[c]pyrrol-4-amine

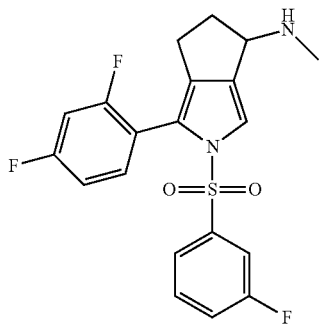 [SMILES: CNC1CCc2c1cn(S(=O)(=O)c1cccc(F)c1)c2-c1ccc(F)cc1F]

To a solution of 1-(2,4-difluorophenyl)-2-((3-fluorophenyl)sulfonyl)-5,6-dihydrocyclopenta[c]pyrrol-4(2H)-one (200 mg, 0.5 mmole) prepared in the step 2 in methanol (5 ml), tetraisopropoxytitanium(IV)(0.76 ml, 2.6 mmole) and 2M methylamine-tetrahydrofurane solution (1.3 ml, 2.6 mmole) were added, and then, the mixture was stirred at room temperature for 4 hours. Sodium borohydride (193 mg, 5.1 mmole) was put, and the mixture was stirred at room temperature for 1 hour, and then, the reaction mixture was concentrated under reduced pressure. A saturated aqueous solution of sodium bicarbonate was added thereto, and the mixture was extracted with ethyl acetate. The extract was washed with saturated brine, dried over anhydrous magnesium sulfate, and concentrated under reduced pressure. The obtained residue was purified with silica gel column chromatography (methanol:ethyl acetate=1:5 (v/v)) to prepare 100 mg of the title compound (yield 48%).

$^1$H NMR (500 MHz, CDCl$_3$): 7.66-7.79 (m, 3H), 7.51-7.57 (m, 2H), 7.10 (d, 1H), 6.91 (d, 1H), 6.73 (s, 1H), 3.89 (br, 1H), 3.31 (s, 3H), 2.36-2.46 (m, 2H), 1.78-2.04 (m, 2H)

Example 114: Preparation of (3-chlorophenyl)(1-(2,4-difluorophenyl)-4-(methylamino)-5,6-dihydrocyclopenta[c]pyrrol-2(4H)-yl)methanone Step 1: Preparation of tert-butyl (1-(2,4-difluorophenyl)-2-((3-fluorophenyl)sulfonyl)-2,4,5,6-tetrahydrocyclopenta[c]pyrrol-4-yl)(methyl)carbamate

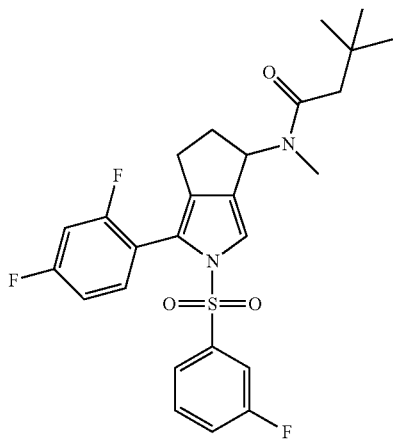 [SMILES: CN(C(=O)CC(C)(C)C)C1CCc2c1cn(S(=O)(=O)c1cccc(F)c1)c2-c1ccc(F)cc1F]

1-(2,4-difluorophenyl)-2-((3-fluorophenyl)sulfonyl)-N-methyl-2,4,5,6-tetrahydrocyclopenta[c]pyrrol-4-amine (80 mg, 0.2 mmole) prepared in Example 113 was dissolved in an ethyl acetate solution (2 ml), di-tert-butyl dicarbonate (47 mg, 0.2 mmole) was added, and then, the mixture was stirred at room temperature for 20 hours. In the reaction mixture, water was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:3 (v/v)) to prepare 65 mg of the title compound (yield 65%).

$^1$H NMR (500 MHz, CD$_3$OD): 7.49-7.52 (m, 1H), 7.40 (td, 1H), 7.30 (d, 1H), 7.22-7.28 (m, 2H), 7.17 (d, 1H), 6.96-7.01 (m, 2H), 4.07-4.11 (m, 1H), 2.61 (s, 3H), 2.49-2.57 (m, 2H), 2.35-2.42 (m, 1H), 2.10-2.17 (m, 1H), 1.48 (s, 9H)

Step 2: Preparation of tert-butyl (1-(2,4-difluorophenyl)-2,4,5,6-tetrahydrocyclopenta[c]pyrrol-4-yl)(methyl)carbamate

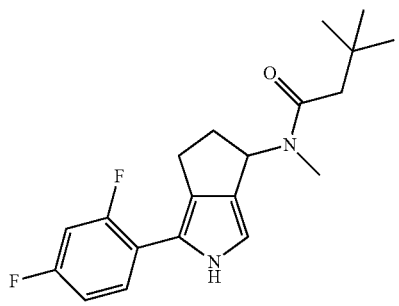 [SMILES: CN(C(=O)CC(C)(C)C)C1CCc2c1c[nH]c2-c1ccc(F)cc1F]

Tert-butyl (1-(2,4-difluorophenyl)-2-((3-fluorophenyl)sulfonyl)-2,4,5,6-tetrahydrocyclopenta[c]pyrrol-4-yl)(methyl)carbamate (55 mg, 0.1 mmole) prepared in the step 1 was dissolved in a tetrahydrofurane solution (2 ml), a 1M tetrabutylammonium fluoride-tetrahydrofurane solution (5 ml) was added, and then, the mixture was stirred at 70° C. for 20 hours. In the reaction mixture, water was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:3 (v/v)) to prepare 22 mg of the title compound (yield 58%).

$^1$H NMR (500 MHz, CD$_3$OD): 7.48-7.53 (m, 1H), 6.95-7.00 (m, 2H), 6.57 (s, 1H), 5.56 (br, 1H), 2.88-2.92 (m, 1H), 2.64-2.76 (m, 3H), 2.62 (s, 3H), 2.21 (br, 1H), 1.49 (s, 9H)

Step 3: Preparation of tert-butyl (2-(3-chlorobenzoyl)-1-(2,4-difluorophenyl)-2,4,5,6-tetrahydrocyclopenta[c]pyrrol-4-yl)(methyl)carbamate

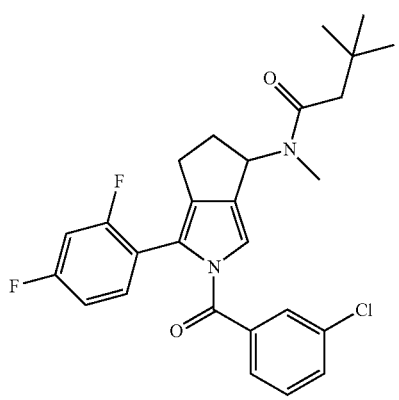 [SMILES: CN(C(=O)CC(C)(C)C)C1CCc2c1cn(C(=O)c1cccc(Cl)c1)c2-c1ccc(F)cc1F]

Tert-butyl (1-(2,4-difluorophenyl)-2,4,5,6-tetrahydrocyclopenta[c]pyrrol-4-yl)(methyl)carbamate (20 mg, 0.05 mmole) prepared in the step 2 was dissolved in a N,N-dimethylformamide solution (1 ml), the mixture was cooled to 0° C., and sodium hydride (60% in oil)(4 mg, 0.1 mmole) was added dropwise. The reaction mixture was stirred at 0° C. for 30 minutes, and then, 3-chlorobenzoyl chloride (0.012 ml, 0.09 mmole) was put, and the mixture was stirred at 0° C. for 1 hour. In the reaction mixture, water was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:4 (v/v)) to prepare 20 mg of the title compound (yield 71%).

$^1$H NMR (500 MHz, CD$_3$OD): 7.64 (s, 1H), 7.61 (d, 1H), 7.58 (d, 1H), 7.43 (t, 1H), 7.35-7.40 (m, 1H), 6.93 (td, 1H), 6.89 (s, 1H), 6.83 (td, 1H), 5.61 (br, 1H), 2.75-2.85 (m, 1H), 2.72 (s, 1H), 2.61-2.68 (m, 2H), 2.23-2.32 (m, 1H), 1.46 (s, 9H)

Step 4: Preparation of (3-chlorophenyl)(1-(2,4-difluorophenyl)-4-(methylamino)-5,6-dihydrocyclopenta[c]pyrrol-2(4H)-yl)methanone

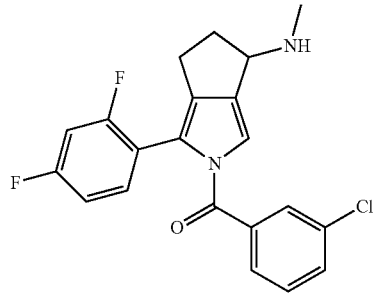 [SMILES: CNC1CCc2c1cn(C(=O)c1cccc(Cl)c1)c2-c1ccc(F)cc1F]

To tert-butyl (2-(3-chlorobenzoyl)-1-(2,4-difluorophenyl)-2,4,5,6-tetrahydrocyclopenta[c]pyrrol-4-yl)(methyl) carbamate (15 mg, 0.03 mmole) prepared in the step 3, a 1.25M hydrochloric acid-methanol solution (0.5 ml) was put, and the mixture was stirred at room temperature for 20 hours. The reaction mixture was concentrated under reduced pressure, and then, a saturated aqueous solution of sodium bicarbonate was added thereto, and the mixture was extracted with ethyl acetate. The extract was washed with saturated brine, dried over anhydrous magnesium sulfate, and concentrated under reduced pressure. The obtained residue was purified with silica gel column chromatography (methanol:ethyl acetate=1:5 (v/v)) to prepare 5 mg of the title compound (yield 42%).

$^1$H NMR (500 MHz, CD$_3$OD): 7.60-7.65 (m, 3H), 7.44-7.47 (m, 1H), 7.36-7.41 (m, 1H), 7.24 (br, 1H), 6.94-6.95 (m, 1H), 6.84-6.86 (m, 1H), 4.41 (br, 1H), 2.87-2.91 (m, 1H), 2.77-2.84 (m, 1H), 2.69-2.74 (m, 1H), 2.64 (s, 3H), 2.39-2.41 (m, 1H)

Example 115: Preparation of 5-((3-chlorophenyl)sulfonyl)-4-(2-fluorophenyl)-N-methyl-1,2,3,5-tetrahydropyrrolo[3,4-c]pyrrol-1-amine hydrochloride Step 1: Preparation of tert-butyl 1-oxo-3,5-dihydropyrrolo[3,4-c]pyrrol-2(1H)-carboxylate

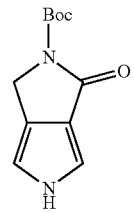 [SMILES: CC(C)(C)OC(=O)N1Cc2c[nH]cc2C1=O]

To a solution of tert-butyl 2-oxo-2,5-dihydro-1H-pyrrol-1-carboxylate (500 mg, 2.7 mmole) in tetrahydrofurane (5 ml), p-toluenesulfonylmethyl isocyanide (533 mg, 2.7 mmole) was added, the mixture was stirred at room temperature for 10 minutes, and then, cooled to −78° C., and a solution of potassium t-butoxide (368 mg, 3.3 mmole) in tetrahydrofurane (5 ml) was slowly added dropwise at −78° C. for 30 minutes. To the reaction mixture, a saturated aqueous solution of ammonium chloride was added, and the mixture was extracted with ethyl acetate. The separated organic layer was washed with saturated brine, dried over anhydrous magnesium sulfate, and concentrated under reduced pressure. The obtained residue was purified with silica gel column chromatography (ethyl acetate:n-hexane=5:1 (v/v)) to prepare 310 mg of the title compound (yield 51%).

$^1$H NMR (500 MHz, CD$_3$OD): 7.23 (s, 1H), 6.69 (s, 1H), 4.64 (s, 2H), 1.57 (s, 9H)

Step 2: Preparation of tert-butyl 4-bromo-1-oxo-3,5-dihydropyrrolo[3,4-c]pyrrol-2(1H)-carboxylate

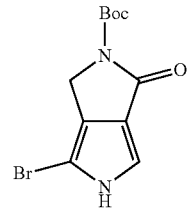

Tert-butyl 1-oxo-3,5-dihydropyrrolo[3,4-c]pyrrol-2(1H)-carboxylate (30 mg, 0.1 mmole) prepared in the step 1 was dissolved in a tetrahydrofurane solution (2 ml), and the mixture was cooled to −78° C. N-bromosuccinimide (25.2 mg, 0.1 mmole) was added thereto, and then, the mixture was stirred at room temperature for 1 hour. In the reaction mixture, water was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=2:1 (v/v)) to prepare 26.4 mg of the title compound (yield 65%).

$^1$H NMR (500 MHz, CDCl$_3$): 9.48 (br, 1H), 7.26 (s, 1H), 4.53 (s, 2H), 1.57 (s, 9H)

Step 3: Preparation of tert-butyl 4-(2-fluorophenyl)-1-oxo-3,5-dihydropyrrolo[3,4-c]pyrrol-2(1H)-carboxylate

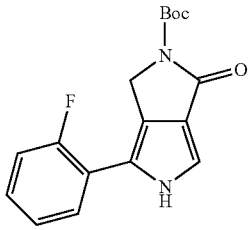 [SMILES: CC(C)(C)OC(=O)N1Cc2c(c[nH]c2-c2ccccc2F)C1=O]

Tert-butyl 4-bromo-1-oxo-3,5-dihydropyrrolo[3,4-c]pyrrol-2(1H)-carboxylate (25 mg, 0.08 mmole) prepared in the step 2, 1,1'-bis(diphenylphosphino)ferrocene-palladium(II) dichloride dichloromethane complex (10 mg, 0.01 mmole), and 2-fluorophenyl boric acid (17 mg, 0.1 mmole) were suspended in a mixture of 1,2-dimethoxyethane (1.5 ml) and 2M sodium carbonate (0.5 ml), and the mixture was reacted in a microwave reactor (120° C., 5 minutes). The reaction mixture was filtered through Celite, water was added to the filtrated, and the mixture was extracted with ethyl acetate. The extract was washed with saturated brine, dried over anhydrous magnesium sulfate, and concentrated under reduced pressure. The obtained residue was purified with silica gel column chromatography (ethyl acetate:n-hexane=2:1 (v/v)) to prepare 21 mg of the title compound (yield 80%).

$^1$H NMR (500 MHz, CDCl$_3$): 9.55 (br, 1H), 7.35-7.37 (m, 2H), 7.15-7.25 (m, 3H), 4.84 (s, 2H), 1.59 (s, 9H)

Step 4: Preparation of tert-butyl 5-((3-chlorophenyl)sulfonyl)-4-(2-fluorophenyl)-1-oxo-3,5-dihydropyrrolo[3,4-c]pyrrol-2(1H)-carboxylate

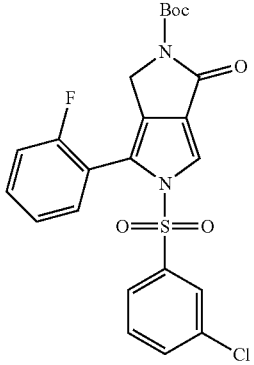 [SMILES: CC(C)(C)OC(=O)N1Cc2c(cn(S(=O)(=O)c3cccc(Cl)c3)c2-c2ccccc2F)C1=O]

Tert-butyl 4-(2-fluorophenyl)-1-oxo-3,5-dihydropyrrolo[3,4-c]pyrrol-2(1H)-carboxylate (20 mg, 0.06 mmole) prepared in the step 3 was dissolved in a N,N-dimethylformamide solution (1 ml), the mixture was cooled to 0° C., and sodium hydride (60% in oil)(40 mg, 0.1 mmole) was added dropwise. The reaction mixture was stirred at 0° C. for 30 minutes, and then, 3-chlorobenzenesulfonyl chloride (20 mg, 0.1 mmole) was put, and the mixture was stirred at 0° C. for 1 hour. In the reaction mixture, water was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:1 (v/v)) to prepare 22.4 mg of the title compound (yield 72%).

$^1$H NMR (500 MHz, CDCl$_3$): 7.95 (s, 1H), 7.54 (d, 1H), 7.48 (q, 1H), 7.31-7.36 (m, 3H), 7.23 (s, 2H), 7.05 (t, 1H), 4.42 (s, 2H), 1.51 (s, 9H)

Step 5: Preparation of tert-butyl 5-((3-chlorophenyl)sulfonyl)-4-(2-fluorophenyl)-1-(methylamino)-3,5-dihydropyrrolo[3,4-c]pyrrol-2(1H)-carboxylate

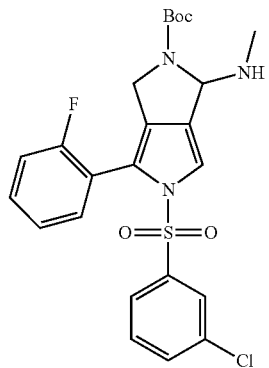 [SMILES: CNC1c2cn(S(=O)(=O)c3cccc(Cl)c3)c(-c3ccccc3F)c2CN1C(=O)OC(C)(C)C]

To a solution of tert-butyl 5-((3-chlorophenyl)sulfonyl)-4-(2-fluorophenyl)-1-oxo-3,5-dihydropyrrolo[3,4-c]pyrrol-2(1H)-carboxylate (30 mg, 0.06 mmole) prepared in the step 4 in methanol (2 ml), sodiumcyanoborohydride (19 mg, 0.3 mmole), zinc chloride (8 mg, 0.06 mmole) and 2M methylamine-tetrahydrofurane solution (0.19 ml, 0.2 mmole) were added, and the mixture was stirred at room temperature for 5 hours. A saturated aqueous solution of sodium bicarbonate was added thereto, and then, the mixture was extracted with ethyl acetate. The extract was washed with saturated brine, dried over anhydrous magnesium sulfate, and concentrated under reduced pressure. The obtained residue was purified with silica gel column chromatography (dichloromethane:methanol=10:1 (v/v)) to prepare 16.7 mg of the title compound 16.7 mg (yield 54%).

$^1$H NMR (500 MHz, CDCl$_3$): 7.90 (s, 1H), 7.55 (d, 1H), 7.45-7.49 (m, 1H), 7.31-7.35 (m, 2H), 7.21-7.22 (m, 1H), 7.19 (d, 1H), 7.12-7.14 (m, 1H), 7.01 (t, 1H), 5.40 (br, 1H), 3.87-4.04 (m, 2H), 2.97 (d, 3H), 1.35 (s, 9H)

Step 6: Preparation of 5-((3-chlorophenyl)sulfonyl)-4-(2-fluorophenyl)-N-methyl-1,2,3,5-tetrahydropyrrolo[3,4-c]pyrrol-1-amine hydrochloride

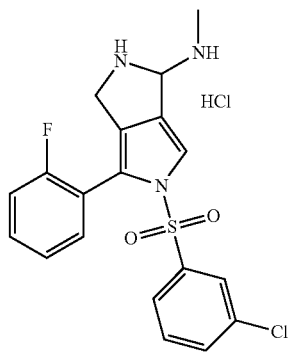 [SMILES: CNC1NCc2c1cn(S(=O)(=O)c1cccc(Cl)c1)c2-c1ccccc1F ; Cl]

In tert-butyl 5-((3-chlorophenyl)sulfonyl)-4-(2-fluorophenyl)-1-(methylamino)-3,5-dihydropyrrolo[3,4-c]pyrrol-2(1H)-carboxylate (15 mg, 0.03 mmole) prepared in the step 5, a 1.25M hydrochloric acid-methanol solution (1 ml) was put, and the mixture was stirred at room temperature for 5 hours. The reaction mixture was concentrated under reduced pressure, and then, the obtained residue was recrystallized from dichloromethane to prepare 9.4 mg of the title compound (yield 71.7%).

$^1$H NMR (500 MHz, CD$_3$OD): 8.29 (s, 1H), 7.73 (d, 1H), 7.60-7.64 (m, 1H), 7.51 (t, 1H), 7.45 (d, 1H), 7.28-7.31 (m, 2H), 7.15-7.20 (m, 2H), 3.79 (d, 1H), 3.61 (d, 1H), 3.34 (br, 1H), 2.92 (s, 3H)

Example 116: Preparation of (5-methyl-2-oxo-1,3-dioxol-4-yl)methyl (1-(2,4-difluorophenyl)-2-((3-fluorophenyl)sulfonyl)-2,4,5,6-tetrahydrocyclopenta[c]pyrrol-4-yl)(methyl)carbamate

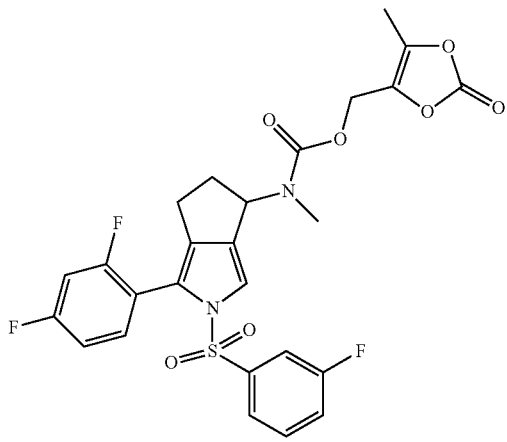 [SMILES: Cc1oc(=O)oc1COC(=O)N(C)C1CCc2c1cn(S(=O)(=O)c1cccc(F)c1)c2-c1ccc(F)cc1F]

1-(2,4-difluorophenyl)-2-((3-fluorophenyl)sulfonyl)-N-methyl-2,4,5,6-tetrahydrocyclopenta[c]pyrrol-4-amine (30 mg, 0.07 mmole) of Example 113 was dissolved in a N,N-dimethylformamide solution (1 ml), and (5-methyl-2-oxo-1,3-dioxol-4-yl)methyl (4-nitrophenyl) carbonate (22 mg, 0.07 mmole) was added dropwise. The reaction mixture was stirred at room temperature for 20 hours, and then, water was introduced in the reaction mixture, and the mixture was extracted with ethyl acetate. The separated organic layer was washed with saturated brine, dried over anhydrous magnesium sulfate, and concentrated under reduced pressure. The obtained residue was purified with silica gel column chromatography (ethyl acetate:n-hexane=4:1 (v/v)) to prepare 10 mg of the title compound (yield 24%).

$^1$H NMR (500 MHz, CD$_3$OD): 7.48-7.53 (m, 1H), 7.40 (t, 1H), 7.29-7.31 (m, 2H), 7.22-7.27 (m, 1H), 7.16 (d, 1H), 6.95-7.01 (m, 2H), 5.48-5.65 (m, 1H), 4.96 (s, 2H), 2.66 (s, 3H), 2.50-2.58 (m, 2H), 2.38-2.43 (m, 1H), 2.16-2.19 (m, 4H)

Example 117: Preparation of 4-(((1-(2,4-difluorophenyl)-2-((3-fluorophenyl)sulfonyl)-2,4,5,6-tetrahydrocyclopenta[c]pyrrol-4-yl)(methyl)amino)methyl)-5-methyl-1,3-dioxol-2-one

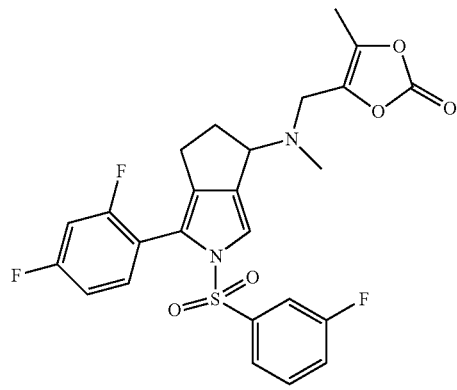 [SMILES: Cc1oc(=O)oc1CN(C)C1CCc2c1cn(S(=O)(=O)c1cccc(F)c1)c2-c1ccc(F)cc1F]

1-(2,4-difluorophenyl)-2-((3-fluorophenyl)sulfonyl)-N-methyl-2,4,5,6-tetrahydrocyclopenta[c]pyrrol-4-amine (30 mg, 0.07 mmole) of Example 113 was dissolved in a N,N-dimethylformamide solution (1 ml), and sodium carbonate (16 mg, 0.15 mmole) was added dropwise. The reaction mixture was stirred at room temperature for 10 minutes, and then, 4-(chloromethyl)-5-methyl-1,3-dioxol-2-one (16.5 mg, 0.1 mmole) was slowly added dropwise. The reaction mixture was stirred at room temperature for 20 hours, and then, water was introduced in the reaction mixture, and the mixture was extracted with ethyl acetate. The separated organic layer was washed with saturated brine, dried over anhydrous magnesium sulfate, and concentrated under reduced pressure. The obtained residue was purified with silica gel column chromatography (ethyl acetate:n-hexane=4:1 (v/v)) to prepare 8 mg of the title compound (yield 21%).

$^1$H NMR (500 MHz, CD$_3$OD): 7.48-7.53 (m, 1H), 7.37-7.41 (m, 2H), 7.31 (d, 1H), 7.22-7.28 (m, 1H), 7.19 (d, 1H), 6.96-6.99 (m, 2H), 4.22-4.26 (m, 1H), 3.40 (q, 2H), 2.43-2.54 (m, 2H), 2.35-2.40 (m, 1H), 2.25-2.31 (m, 1H), 2.24 (s, 3H), 2.12 (s, 3H)

Example 118: Preparation of (5-methyl-2-oxo-1,3-dioxol-4-yl)methyl (2-((3-chlorophenyl)sulfonyl)-1-(2-fluorophenyl)-2,4,5,6-tetrahydrocyclopenta[c]pyrrol-4-yl)(methyl)carbamate Step 1: Preparation of 4-(hydroxymethyl)-5-methyl-1,3-dioxol-2-one

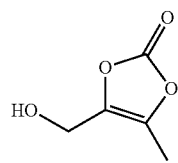

4-(chloromethyl)-5-methyl-1,3-dioxol-2-one (400 mg, 2.7 mmole) was dissolved in an acetonitrile solution (10 ml), formic acid (496 mg, 10.8 mmole) was added dropwise, and then, the mixture was stirred at room temperature for 5 minutes. The reaction mixture was cooled to 0° C., triethylamine (0.8 ml, 5.4 mmole) was added thereto, and the mixture was stirred at 60° C. for 8 hours, and then, water was introduced, and the mixture was extracted with ethyl acetate. The separated organic layer was washed with saturated brine, dried over anhydrous magnesium sulfate, and concentrated under reduced pressure. The obtained residue was dissolved in methanol (10 ml), concentrated hydrochloric acid (1 ml) was added thereto, and then, the mixture was stirred at room temperature for 2 hours. In the reaction mixture, a saturated aqueous solution of sodium bicarbonate was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:2 (v/v)) to prepare 150 mg of the title compound (yield 43%).

$^1$H NMR (500 MHz, CDCl$_3$): 4.20 (s, 2H), 2.31 (s, 3H)

Step 2: Preparation of (5-methyl-2-oxo-1,3-dioxol-4-yl)methyl (4-nitrophenyl) carbonate

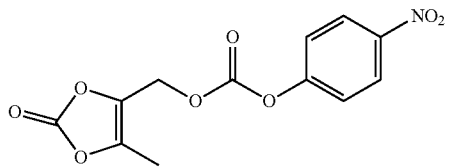 [SMILES: Cc1oc(=O)oc1COC(=O)Oc1ccc([N+](=O)[O-])cc1]

4-(hydroxymethyl)-5-methyl-1,3-dioxol-2-one (150 mg, 1.2 mmole) prepared in the step 1 was dissolved in a chloroform solution (2 ml), the mixture was cooled to 0° C., and pyridine (0.1 ml, 1.3 mmole) was added dropwise. The reaction mixture was stirred at 0° C. for 5 minutes, and then, 4-nitrophenyl carbonochloridate (255 mg, 1.3 mmole) was introduced, and the mixture was stirred at room temperature for 18 hours. In the reaction mixture, a saturated aqueous solution of sodium bicarbonate was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:2 (v/v)) to prepare 138 mg of the title compound (yield 37%).

$^1$H NMR (500 MHz, CDCl$_3$): 8.30 (d, 2H), 7.52 (d, 2H), 4.84 (s, 2H), 2.25 (s, 3H)

Step 3: Preparation of (5-methyl-2-oxo-1,3-dioxol-4-yl)methyl (2-((3-chlorophenyl)sulfonyl)-1-(2-fluorophenyl)-2,4,5,6-tetrahydrocyclopenta[c]pyrrol-4-yl)(methyl)carbamate

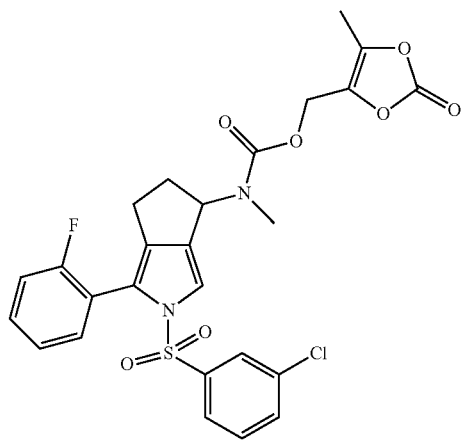 [SMILES: Cc1oc(=O)oc1COC(=O)N(C)C1CCc2c1cn(S(=O)(=O)c1cccc(Cl)c1)c2-c1ccccc1F]

2-((3-chlorophenyl)sulfonyl)-1-(2-fluorophenyl)-N-methyl-2,4,5,6-tetrahydrocyclopenta[c]pyrrol-4-amine (35 mg, 0.09 mmole) of Example 1 was dissolved in a N,N-dimethylformamide solution (1 ml), and (5-methyl-2-oxo-1,3-dioxol-4-yl)methyl (4-nitrophenyl) carbonate (18 mg, 0.06 mmole) prepared in the step 2 was added dropwise. The reaction mixture was stirred at room temperature for 20 hours, and then, water was introduced in the reaction mixture, and the mixture was extracted with ethyl acetate. The separated organic layer was washed with saturated brine, dried over anhydrous magnesium sulfate, and concentrated under reduced pressure. The obtained residue was purified with silica gel column chromatography (ethyl acetate:n-hexane=4:1 (v/v)) to prepare 12 mg of the title compound (yield 34.6%).

$^1$H NMR (500 MHz, CD$_3$OD): 7.62 (d, 1H), 7.42-7.46 (m, 2H), 7.40 (d, 1H), 7.32 (s, 1H), 7.28 (s, 1H), 7.18-7.21 (m, 2H), 7.10 (t, 1H), 5.50-5.65 (m, 1H), 4.96 (s, 2H), 2.66 (s, 3H), 2.50-2.59 (m, 2H), 2.36-2.42 (m, 1H), 2.19 (s, 3H), 2.12-2.18 (m, 1H)

Example 119: Preparation of 4-(((2-((3-chlorophenyl)sulfonyl)-1-(2-fluorophenyl)-2,4,5,6-tetrahydrocyclopenta[c]pyrrol-4-yl)(methyl)amino)methyl)-5-methyl-1,3-dioxol-2-one

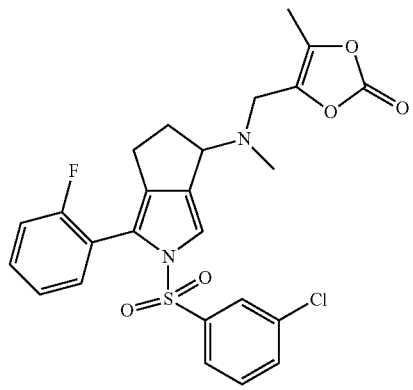 [SMILES: Cc1oc(=O)oc1CN(C)C1CCc2c1cn(S(=O)(=O)c1cccc(Cl)c1)c2-c1ccccc1F]

2-((3-chlorophenyl)sulfonyl)-1-(2-fluorophenyl)-N-methyl-2,4,5,6-tetrahydrocyclopenta[c]pyrrol-4-amine (35 mg, 0.09 mmole) of Example 1 was dissolved in a N,N-dimethylformamide solution (1 ml), and sodium carbonate (13.7 mg, 0.13 mmole) was added dropwise. The reaction mixture was stirred at room temperature for 10 minutes, and then, 4-(chloromethyl)-5-methyl-1,3-dioxol-2-one (19 mg, 0.13 mmole) was slowly added dropwise. The reaction mixture was stirred at room temperature for 20 hours, and then, water was introduced, and the mixture was extracted with ethyl acetate. The separated organic layer was washed with saturated brine, dried over anhydrous magnesium sulfate, and concentrated under reduced pressure. The obtained residue was purified with silica gel column chromatography (methanol:ethyl acetate=1:5 (v/v)) to prepare 15 mg of the title compound (yield 33.6%).

$^1$H NMR (500 MHz, CD$_3$OD): 7.62 (d, 1H), 7.41-7.46 (m, 3H), 7.35 (d, 2H), 7.19-7.22 (m, 2H), 7.10 (t, 1H), 4.23-4.26 (m, 1H), 3.39 (q, 2H), 2.42-2.54 (m, 2H), 2.34-2.39 (m, 1H), 2.24-2.29 (m, 1H), 2.22 (s, 3H), 2.12 (s, 3H)

Example 120: Preparation of 1-(2-fluorophenyl)-2-((3-fluorophenyl)sulfonyl)-N-methyl-4,5,6,7-tetrahydro-2H-isoindole-4-amine Step 1: Preparation of 1-bromo-2,5,6,7-tetra-4H-isoindole-4-one

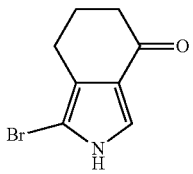 [SMILES: O=C1CCCc2c1c[nH]c2Br]

2,5,6,7-tetrahydro-4H-isoindole-4-one (500 mg, 3.7 mmole) was dissolved in a tetrahydrofurane (40 ml), and the solution was cooled to −78° C. N-bromosuccinimide (658 mg, 3.7 mmole) was added thereto, and then, the mixture was stirred at room temperature for 5 hours. In the reaction mixture, water was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:1 (v/v)) to prepare 463 mg of the title compound (yield 58%).

$^1$H NMR (500 MHz, CDCl$_3$): 8.55 (br, 1H), 7.36 (s, 1H), 2.57-2.60 (m, 2H), 2.47-2.49 (m, 2H), 2.04-2.09 (m, 2H)

Step 2: Preparation of 1-(2-fluorophenyl)-2,5,6,7-tetrahydro-4H-isoindole-4-one

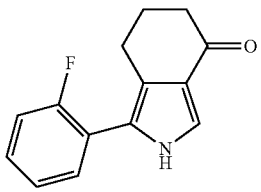 [SMILES: O=C1CCCc2c1c[nH]c2-c1ccccc1F]

1-bromo-2,5,6,7-tetra-4H-isoindole-4-one (50 mg, 0.2 mmole) prepared in the step 1, palladium(II) acetate (2.6 mg, 0.01 mmole), tris(2-methoxyphenyl)phosphine (6 mg, 0.02 mmole), potassium phosphate tribasic (175 mg, 0.8 mmole), and 2-fluorophenyl boric acid (49 mg, 0.4 mmole) were suspended in 1,2-dimethoxyethane:water=4:1 solution (2.5 ml), and the mixture was reacted at 90° C. for 1 hour. The reaction mixture was filtered through Celite, water was added to the filtrate, and the mixture was extracted with ethyl acetate. The extract was washed with saturated brine, dried over anhydrous magnesium sulfate, and concentrated under reduced pressure. The obtained residue was purified with silica gel column chromatography (ethyl acetate:n-hexane=2:1 (v/v)) to prepare 29 mg of the title compound (yield 54%).

$^1$H NMR (500 MHz, CDCl$_3$): 9.10 (br, 1H), 7.47-7.52 (m, 2H), 7.14-7.24 (m, 3H), 2.87-2.89 (m, 2H), 2.53-2.56 (m, 2H), 2.09-2.13 (m, 2H)

Step 3: Preparation of 1-(2-fluorophenyl)-2-((3-fluorophenyl)sulfonyl)-2,5,6,7-tetrahydro-4H-isoindole-4-one

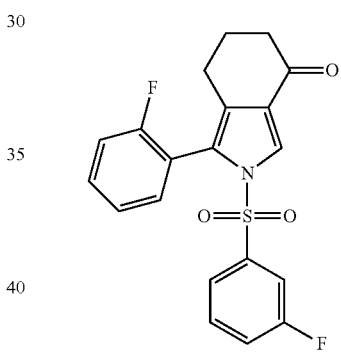

1-(2-fluorophenyl)-2,5,6,7-tetrahydro-4H-isoindole-4-one (50 mg, 0.2 mmole) prepared in the step 2 was dissolve in N,N-dimethylformamide (3 ml), the solution was cooled to 0° C., and sodium hydride (60% in oil)(13 mg, 0.3 mmole) was added dropwise. The reaction mixture was stirred at 0° C. for 30 minutes, and then, 3-fluorobenzenesulfonyl chloride (63 mg, 0.3 mmole) was introduced, and the mixture was stirred at room temperature for 3 hours. In the reaction mixture, water was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:1 (v/v)) to prepare 41 mg of the title compound (yield 48.5%).

$^1$H NMR (500 MHz, CDCl$_3$): 7.85 (s, 1H), 7.66-7.79 (m, 4H), 7.57 (d, 1H), 7.51 (d, 1H), 7.27-7.46 (m, 2H), 2.66 (t, 2H), 2.46-2.53 (m, 2H), 2.00-2.04 (m, 2H)

Step 4: Preparation of 1-(2-fluorophenyl)-2-((3-fluorophenyl)sulfonyl)-N-methyl-4,5,6,7-tetrahydro-2H-isoindole-4-amine

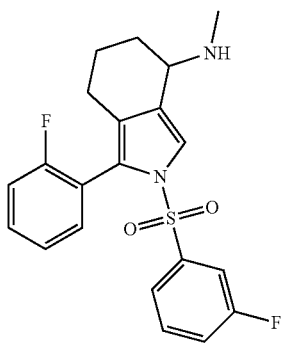 [SMILES: CNC1CCCc2c1cn(S(=O)(=O)c1cccc(F)c1)c2-c1ccccc1F]

To a solution of 1-(2-fluorophenyl)-2-((3-fluorophenyl)sulfonyl)-2,5,6,7-tetrahydro-4H-isoindole-4-one (20 mg, 0.05 mmole) prepared in the step 3 in methanol (3 ml), tetraisopropoxytitanium(IV)(28 mg, 0.1 mmole) and 2M methylamine-tetrahydrofurane (0.1 ml, 0.2 mmole) were added, and the mixture was stirred at room temperature for 4 hours. Sodium borohydride (4 mg, 0.1 mmole) was introduced, and the mixture was stirred at room temperature for 12 hours, and then, the reaction mixture was concentrated under reduced pressure. A saturated aqueous solution of sodium bicarbonate was added thereto, and then, the mixture was extracted with ethyl acetate. The extract was washed with saturated brine, dried over anhydrous magnesium sulfate, and concentrated under reduced pressure. The obtained residue was purified with silica gel column chromatography (dichloromethane:methanol=10:1 (v/v)) to prepare 6.4 mg of the title compound (yield 31%).

$^1$H NMR (500 MHz, CDCl$_3$): 7.52 (d, 1H), 7.33-7.39 (m, 2H), 7.15-7.24 (m, 4H), 7.07 (d, 1H), 7.00-7.04 (m, 1H), 3.83 (br, 1H), 2.55 (s, 3H), 2.17-2.23 (m, 2H), 1.84-1.88 (m, 1H), 1.56-1.58 (m, 3H)

In the Examples 121 to 135 below, title compounds were prepared by the same method as Example 120, except that reactants were appropriately changed considering the structure of the compounds to be prepared and the Reaction Scheme 1.

Example 121: Preparation of 1-(2-fluorophenyl)-N-methyl-2-(m-tolylsulfonyl)-4,5,6,7-tetrahydro-2H-isoindole-4-amine

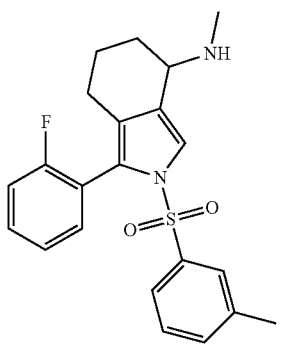 [SMILES: CNC1CCCc2c1cn(S(=O)(=O)c1cccc(C)c1)c2-c1ccccc1F]

$^1$H NMR (500 MHz, CDCl$_3$): 7.39 (d, 1H), 7.34-7.38 (m, 1H), 7.30 (br, 1H), 7.20-7.25 (m, 3H), 7.11-7.16 (m, 2H), 7.00 (q, 1H), 3.68 (br, 1H), 2.52 (s, 3H), 2.28 (s, 3H), 2.12-2.21 (m, 2H), 1.94-2.01 (m, 1H), 1.81-1.82 (m, 1H), 1.49-1.60 (m, 2H)

Example 122: Preparation of 1-(2-fluorophenyl)-2-((3-methoxyphenyl)sulfonyl)-N-methyl-4,5,6,7-tetrahydro-2H-isoindole-4-amine

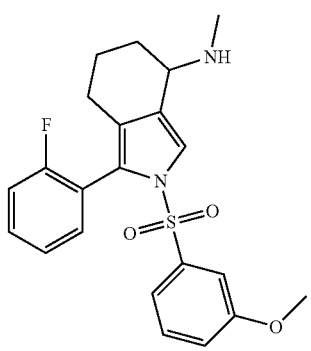 [SMILES: CNC1CCCc2c1cn(S(=O)(=O)c1cccc(OC)c1)c2-c1ccccc1F]

$^1$H NMR (500 MHz, CDCl$_3$): 7.45 (d, 1H), 7.33-7.37 (m, 1H), 7.24-7.27 (m, 1H), 7.11-7.22 (m, 2H), 6.99-7.06 (m, 3H), 6.87 (br, 1H), 3.73 (br, 1H), 3.71 (s, 3H), 2.53 (d, 3H), 2.16-2.23 (m, 2H), 1.97-2.03 (m, 1H), 1.82-1.86 (m, 1H), 1.52-1.63 (m, 2H)

Example 123: Preparation of 2-((3-(difluoromethoxy)phenyl)sulfonyl)-1-(2-fluorophenyl)-N-methyl-4,5,6,7-tetrahydro-2H-isoindole-4-amine

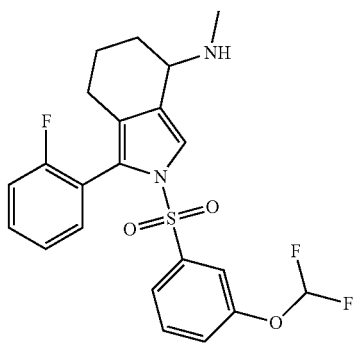 [SMILES: CNC1CCCc2c1cn(S(=O)(=O)c1cccc(OC(F)F)c1)c2-c1ccccc1F]

$^1$H NMR (500 MHz, CDCl$_3$): 7.68-7.70 (m, 4H), 7.33-7.49 (m, 2H), 7.15-7.23 (m, 2H), 6.98 (br, 1H), 6.81-6.87 (m, 1H), 3.81 (br, 1H), 3.62 (s, 3H), 2.32-2.36 (m, 2H), 2.01-2.06 (m, 2H), 1.95-1.99 (m, 2H)

Example 124: Preparation of 1-(2-fluorophenyl)-N-methyl-2-((3-(trifluoromethyl)phenyl)sulfonyl)-4,5,6,7-tetrahydro-2H-isoindole-4-amine

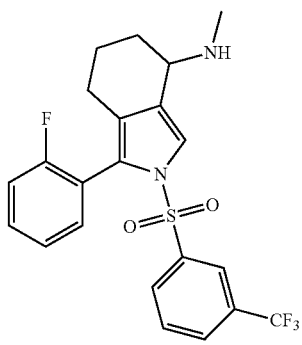 [SMILES: CNC1CCCc2c1cn(S(=O)(=O)c1cccc(C(F)(F)F)c1)c2-c1ccccc1F]

¹H NMR (500 MHz, CDCl₃): 7.77 (d, 1H), 7.69 (d, 1H), 7.57 (d, 1H), 7.53 (t, 1H), 7.48 (d, 1H), 7.36-7.39 (m, 1H), 7.14-7.22 (m, 2H), 6.97-7.02 (m, 1H), 3.74 (br, 1H), 2.54 (s, 3H), 2.15-2.21 (m, 2H), 2.00-2.04 (m, 1H), 1.81-1.87 (m, 1H), 1.51-1.62 (m, 2H)

Example 125: Preparation of 1-(2-fluorophenyl)-N-methyl-2-((3-(trifluoromethoxy)phenyl)sulfonyl)-4,5,6,7-tetrahydro-2H-isoindole-4-amine

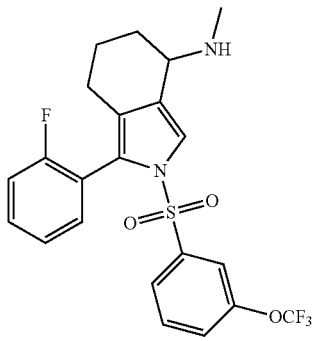 [SMILES: CNC1CCCc2c1cn(S(=O)(=O)c1cccc(OC(F)(F)F)c1)c2-c1ccccc1F]

¹H NMR (500 MHz, CDCl₃): 7.63 (d, 1H), 7.29-7.37 (m, 1H), 7.21-7.25 (m, 1H), 7.13-7.20 (m, 2H), 6.88-7.00 (m, 3H), 6.90 (br, 1H), 3.70 (br, 1H), 3.67 (s, 3H), 2.14-2.21 (m, 2H), 2.00-2.03 (m, 1H), 1.89-1.95 (m, 1H), 1.61-1.66 (m, 2H)

Example 126: Preparation of 2-((5-chloro-2-fluorophenyl)sulfonyl)-1-(2-fluorophenyl)-N-methyl-4,5,6,7-tetrahydro-2H-isoindole-4-amine

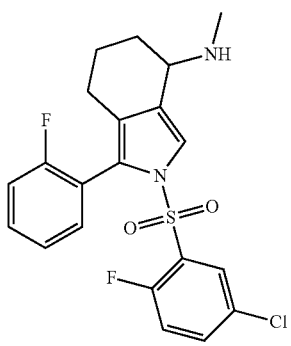 [SMILES: CNC1CCCc2c1cn(S(=O)(=O)c1cc(Cl)ccc1F)c2-c1ccccc1F]

¹H NMR (500 MHz, CDCl₃): 7.75 (d, 1H), 7.35-7.40 (m, 2H), 7.15-7.24 (m, 3H), 7.11 (s, 1H), 6.95 (br, 1H), 3.65 (s, 3H), 2.15-2.20 (m, 2H), 2.05-2.08 (m, 1H), 1.90-1.95 (m, 1H), 1.67-1.70 (m, 2H)

Example 127: Preparation of 1-([1,1'-biphenyl]-4-yl)-2-((3-chlorophenyl)sulfonyl)-N-methyl-4,5,6,7-tetrahydro-2H-isoindole-4-amine

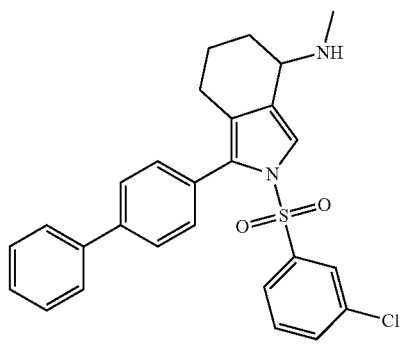 [SMILES: CNC1CCCc2c1cn(S(=O)(=O)c1cccc(Cl)c1)c2-c1ccc(-c2ccccc2)cc1]

¹H NMR (500 MHz, CDCl₃): 7.66 (d, 2H), 7.57 (d, 2H), 7.45-7.48 (m, 3H), 7.36-7.39 (m, 2H), 7.26-7.32 (m, 3H), 7.19 (d, 2H), 3.70 (br, 1H), 2.55 (s, 3H), 2.29-2.31 (m, 2H), 1.97-2.01 (m, 1H), 1.81-1.85 (m, 1H), 1.55-1.58 (m, 2H)

Example 128: Preparation of 2-((3-chlorophenyl)sulfonyl)-N-methyl-1-(pyridin-4-yl)-4,5,6,7-tetrahydro-2H-isoindole-4-amine

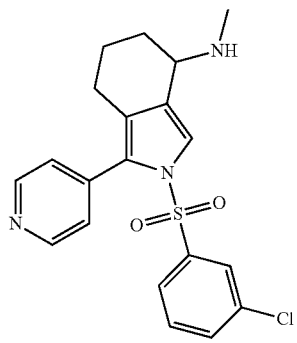 [SMILES: CNC1CCCc2c1cn(S(=O)(=O)c1cccc(Cl)c1)c2-c1ccncc1]

¹H NMR (500 MHz, CDCl₃): 8.75 (d, 2H), 8.23 (s, 1H), 7.99 (d, 2H), 7.68-7.77 (m, 3H), 6.72 (s, 1H), 3.81 (br, 1H), 3.26 (s, 3H), 2.67-2.70 (m, 2H), 1.72-1.82 (m, 2H), 1.50-1.75 (m, 2H)

Example 129: Preparation of 2-((3-chlorophenyl)sulfonyl)-N-methyl-1-(pyrimidin-5-yl)-4,5,6,7-tetrahydro-2H-isoindole-4-amine

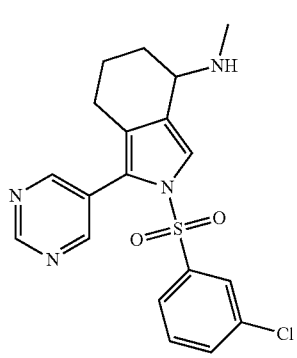 [SMILES: CNC1CCCc2c1cn(S(=O)(=O)c1cccc(Cl)c1)c2-c1cncnc1]

¹H NMR (500 MHz, CDCl₃): 9.36 (s, 1H), 9.12 (d, 2H), 8.23 (s, 1H), 7.64-7.77 (m, 3H), 6.74 (s, 1H), 3.83 (br, 1H), 3.23 (s, 3H), 2.61-2.68 (m, 2H), 1.68-1.78 (m, 2H), 1.61-1.73 (m, 2H)

Example 130: Preparation of 2-((3-(dimethylamino) phenyl)sulfonyl)-1-(2-fluorophenyl)-N-methyl-4,5,6,7-tetrahydro-2H-isoindole-4-amine

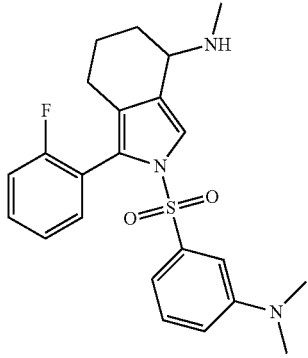 [SMILES: CNC1CCCc2c1cn(S(=O)(=O)c1cccc(N(C)C)c1)c2-c1ccccc1F]

¹H NMR (500 MHz, CDCl₃): 7.71-7.75 (m, 2H), 7.49-7.52 (m, 2H), 7.27-7.33 (m, 2H), 7.11-7.14 (m, 2H), 6.72 (s, 1H), 3.81 (br, 1H), 3.26 (s, 3H), 2.87 (s, 6H), 2.42-2.45 (m, 2H), 1.61-1.89 (m, 4H)

Example 131: Preparation of 1-(2-fluorophenyl)-N-methyl-2-(pyridin-3-ylsulfonyl)-4,5,6,7-tetrahydro-2H-isoindole-4-amine

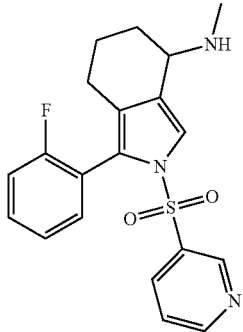 [SMILES: CNC1CCCc2c1cn(S(=O)(=O)c1cccnc1)c2-c1ccccc1F]

¹H NMR (500 MHz, CDCl₃): 8.90 (d, 2H), 8.43 (s, 1H), 7.69-7.75 (m, 3H), 7.27-7.49 (m, 2H), 6.88 (s, 1H), 3.88 (br, 1H), 3.62 (s, 3H), 2.60-2.65 (m, 2H), 1.50-1.81 (m, 4H)

Example 132: Preparation of N-methyl-2-(pyridin-3-ylsulfonyl)-1-(o-tolyl)-4,5,6,7-tetrahydro-2H-isoindole-4-amine

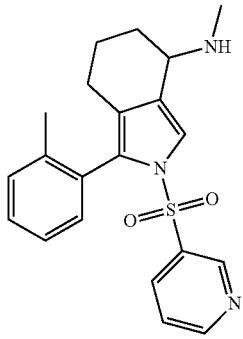

¹H NMR (500 MHz, CDCl₃): 8.88 (d, 2H), 8.40 (s, 1H), 7.65-7.71 (m, 3H), 7.19-7.31 (m, 2H), 6.79 (s, 1H), 3.85 (br, 1H), 3.66 (s, 3H), 2.65-2.69 (m, 2H), 2.65 (s, 3H), 1.48-1.79 (m, 4H)

Example 133: Preparation of 1-(2-chlorophenyl)-N-methyl-2-(pyridin-3-ylsulfonyl)-4,5,6,7-tetrahydro-2H-isoindole-4-amine

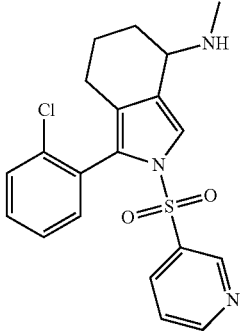 [SMILES: CNC1CCCc2c1cn(S(=O)(=O)c1cccnc1)c2-c1ccccc1Cl]

¹H NMR (500 MHz, CDCl₃): 8.90 (d, 2H), 8.42 (s, 1H), 7.68-7.73 (m, 3H), 7.25-7.46 (m, 2H), 6.85 (s, 1H), 3.84 (br, 1H), 3.68 (s, 3H), 2.62-2.67 (m, 2H), 1.45-1.75 (m, 4H)

Example 134: Preparation of 1-([1,1'-biphenyl]-4-yl)-N-methyl-2-(pyridin-3-ylsulfonyl)-4,5,6,7-tetrahydro-2H-isoindole-4-amine

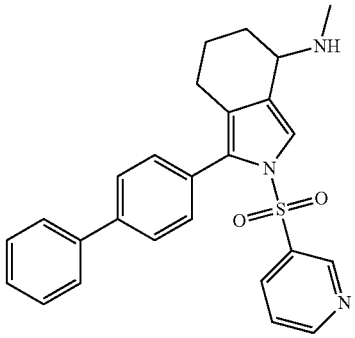 [SMILES: CNC1CCCc2c1cn(S(=O)(=O)c1cccnc1)c2-c1ccc(-c2ccccc2)cc1]

¹H NMR (500 MHz, CDCl₃): 8.90 (d, 2H), 8.42 (s, 1H), 8.30 (d, 2H), 7.85 (d, 2H), 7.69-7.75 (m, 3H), 7.41-7.49 (m, 3H), 6.72 (s, 1H), 3.80 (br, 1H), 3.61 (s, 3H), 2.27-2.30 (m, 2H), 1.95-2.00 (m, 1H), 1.79-1.82 (m, 1H), 1.51-1.58 (m, 2H)

Example 135: Preparation of 1-(2,4-difluorophenyl)-N-methyl-2-(pyridin-3-ylsulfonyl)-4,5,6,7-tetrahydro-2H-isoindole-4-amine

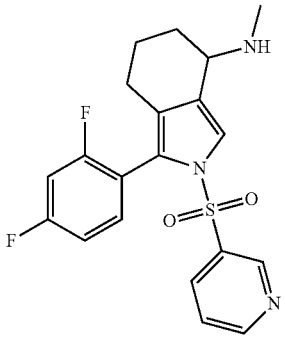 [SMILES: CNC1CCCc2c1cn(S(=O)(=O)c1cccnc1)c2-c1ccc(F)cc1F]

¹H NMR (500 MHz, CDCl₃): 8.9 (d, 2H), 8.42 (s, 1H), 7.69-7.78 (m, 2H), 6.87-7.08 (m, 2H), 6.72 (s, 1H), 3.81 (br, 1H), 3.62 (s, 3H), 2.61-2.66 (m, 2H), 1.46-1.75 (m, 4H)

Example 136: Preparation of 1-(2-fluorophenyl)-2-((3-fluorophenyl)sulfonyl)-N,N-dimethyl-4,5,6,7-tetrahydro-2H-isoindole-4-amine

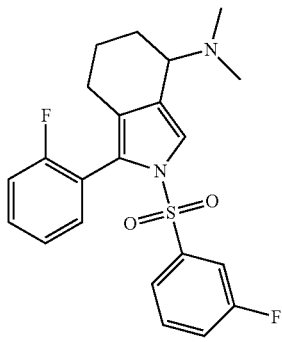 [SMILES: CN(C)C1CCCc2c1cn(S(=O)(=O)c1cccc(F)c1)c2-c1ccccc1F]

To a solution of 1-(2-fluorophenyl)-2-((3-fluorophenyl)sulfonyl)-2,5,6,7-tetrahydro-4H-isoindole-4-one (20 mg, 0.05 mmole) prepared in the step 3 of Example 120 in methanol (3 ml), tetraisopropoxytitanium(IV)(28 mg, 0.1 mmole) and a 2M dimethylamine-tetrahydrofurane solution (0.1 ml, 0.2 mmole) were added, and the mixture was stirred at room temperature for 24 hours. Sodium borohydride (4 mg, 0.1 mmole) was introduced, the mixture was stirred at room temperature for 12 hours, and then, the reaction mixture was concentrated under reduced pressure. A saturated aqueous solution of sodium bicarbonate was added, and the mixture was extracted with ethyl acetate. The extract was washed with saturated brine, dried over anhydrous magnesium sulfate, and concentrated under reduced pressure. The obtained residue was purified with silica gel column chromatography (dichloromethane:methanol=10:1 (v/v)) to prepare 7 mg of the title compound (yield 32.5%).

¹H NMR (500 MHz, CDCl₃): 7.49 (br, 1H), 7.33-7.39 (m, 2H), 7.26-7.28 (m, 1H), 7.0-7.24 (m, 2H), 7.16-7.17 (m, 1H), 7.10 (d, 1H), 7.02-7.07 (m, 1H), 3.87 (br, 1H), 2.40 (d, 6H), 2.15-2.23 (m, 2H), 1.90-1.92 (m, 2H), 1.46-1.50 (m, 2H)

In the Examples 137 to 144 below, title compounds were prepared by the same method as Example 136, except that reactants were appropriately changed considering the structure of the compounds to be prepared and the Reaction Scheme 1.

Example 137: Preparation of 1-(2-fluorophenyl)-N,N-dimethyl-2-(m-tolylsulfonyl)-4,5,6,7-tetrahydro-2H-isoindole-4-amine

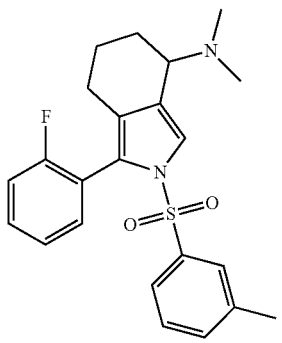 [SMILES: Cc1cccc(S(=O)(=O)n2cc3c(c2-c2ccccc2F)CCCC3N(C)C)c1]

¹H NMR (500 MHz, CDCl₃): 7.65-7.75 (m, 5H), 7.48 (d, 2H), 7.27 (br, 1H), 6.91 (s, 1H), 3.88 (br, 1H), 2.62-2.70 (m, 2H), 2.36 (s, 3H), 2.26 (s, 6H), 1.48-1.89 (m, 4H)

Example 138: Preparation of 2-((3-chlorophenyl)sulfonyl)-1-(2-fluorophenyl)-N,N-dimethyl-4,5,6,7-tetrahydro-2H-isoindole-4-amine

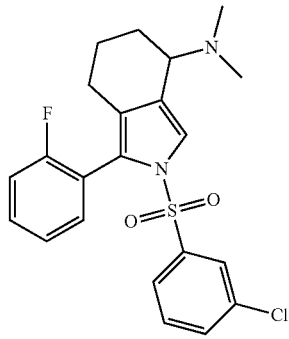 [SMILES: CN(C)C1CCCc2c1cn(S(=O)(=O)c1cccc(Cl)c1)c2-c1ccccc1F]

¹H NMR (500 MHz, CDCl₃): 7.50 (br, 1H), 7.35-7.40 (m, 2H), 7.27-7.30 (m, 1H), 7.05-7.29 (m, 2H), 7.15-7.18 (m, 1H), 7.12 (d, 1H), 7.05-7.10 (m, 1H), 3.88 (br, 1H), 2.38 (d, 6H), 2.10-2.21 (m, 2H), 1.87-1.90 (m, 2H), 1.45-1.49 (m, 2H)

Example 139: Preparation of 1-(2-fluorophenyl)-N,N-dimethyl-2-((3-(trifluoromethyl)phenyl)sulfonyl)-4,5,6,7-tetrahydro-2H-isoindole-4-amine

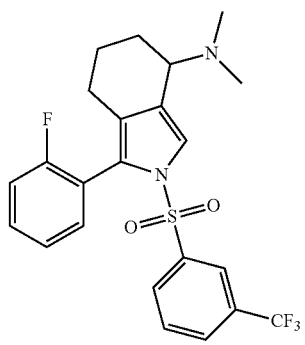 [SMILES: CN(C)C1CCCc2c1cn(S(=O)(=O)c1cccc(C(F)(F)F)c1)c2-c1ccccc1F]

¹H NMR (500 MHz, CDCl₃): 7.53 (br, 1H), 7.36-7.41 (m, 2H), 7.30-7.34 (m, 1H), 7.11-7.28 (m, 2H), 7.18-7.21 (m, 1H), 7.13 (d, 1H), 7.02-7.07 (m, 1H), 3.85 (br, 1H), 2.37 (d, 6H), 2.13-2.21 (m, 2H), 1.87-1.91 (m, 2H), 1.45-1.51 (m, 2H)

Example 140: Preparation of 1-(2-fluorophenyl)-2-((3-methoxyphenyl)sulfonyl)-N,N-dimethyl-4,5,6,7-tetrahydro-2H-isoindole-4-amine

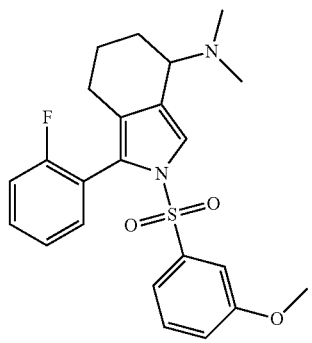 [SMILES: COc1cccc(S(=O)(=O)n2cc3c(c2-c2ccccc2F)CCCC3N(C)C)c1]

¹H NMR (500 MHz, CDCl₃): 7.48 (br, 1H), 7.35-7.41 (m, 2H), 7.29-7.31 (m, 1H), 7.15-7.21 (m, 2H), 7.11 (d, 1H), 7.02-7.07 (m, 1H), 3.81-3.85 (m, 4H), 2.38 (d, 6H), 2.16-2.23 (m, 2H), 1.81-1.88 (m, 2H), 1.46-1.53 (m, 2H)

Example 141: Preparation of 1-(2-fluorophenyl)-N, N-dimethyl-2-((3-(trifluoromethoxy)phenyl)sulfonyl)-4,5,6,7-tetrahydro-2H-isoindole-4-amine

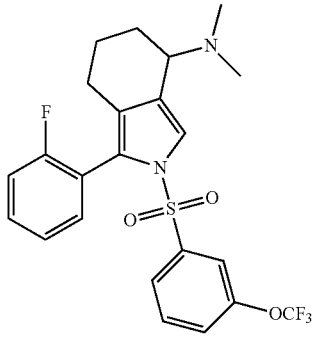 [SMILES: CN(C)C1CCCc2c1cn(S(=O)(=O)c1cccc(OC(F)(F)F)c1)c2-c1ccccc1F]

¹H NMR (500 MHz, CDCl₃): 7.51 (br, 1H), 7.29-7.40 (m, 4H), 7.14-7.19 (m, 2H), 7.07-7.13 (m, 1H), 7.01-7.03 (m, 1H), 3.82 (br, 1H), 2.35 (d, 6H), 2.15-2.21 (m, 2H), 1.81-1.88 (m, 2H), 1.41-1.48 (m, 2H)

Example 142: Preparation of 2-((3-(difluoromethoxy)phenyl)sulfonyl)-1-(2-fluorophenyl)-N,N-dimethyl-4,5,6,7-tetrahydro-2H-isoindole-4-amine

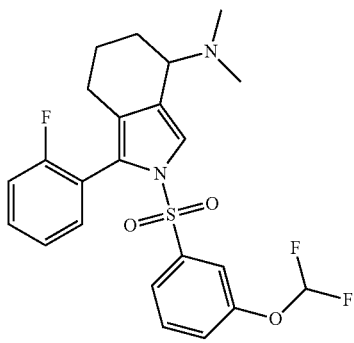 [SMILES: CN(C)C1CCCc2c1cn(S(=O)(=O)c1cccc(OC(F)F)c1)c2-c1ccccc1F]

¹H NMR (500 MHz, CDCl₃): 7.68-7.70 (m, 4H), 7.33-7.49 (m, 2H), 7.15-7.23 (m, 2H), 6.98 (br, 1H), 6.81-6.87 (m, 1H), 3.81 (br, 1H), 2.42 (s, 6H), 2.32-2.36 (m, 2H), 2.01-2.06 (m, 2H), 1.95-1.99 (m, 2H)

Example 143: Preparation of 2-((3-(dimethylamino)phenyl)sulfonyl)-1-(2-fluorophenyl)-N,N-dimethyl-4,5,6,7-tetrahydro-2H-isoindole-4-amine

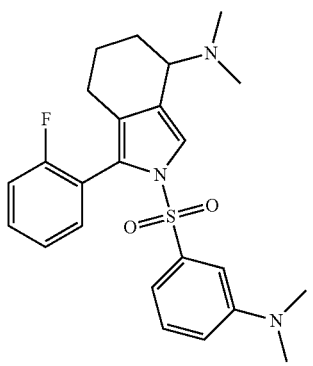 [SMILES: CN(C)c1cccc(S(=O)(=O)n2cc3c(c2-c2ccccc2F)CCCC3N(C)C)c1]

¹H NMR (500 MHz, CDCl₃): 7.71-7.75 (m, 2H), 7.49-7.52 (m, 2H), 7.27-7.33 (m, 2H), 7.11-7.14 (m, 2H), 6.89 (br, 1H), 3.85 (br, 1H), 2.97 (s, 6H), 2.45 (s, 6H), 2.32-2.36 (m, 2H), 2.05-2.09 (m, 2H), 1.89-1.93 (m, 2H)

Example 144: Preparation of 1-(2-fluorophenyl)-N, N-dimethyl-2-(pyridin-3-ylsulfonyl)-4,5,6,7-tetrahydro-2H-isoindole-4-amine

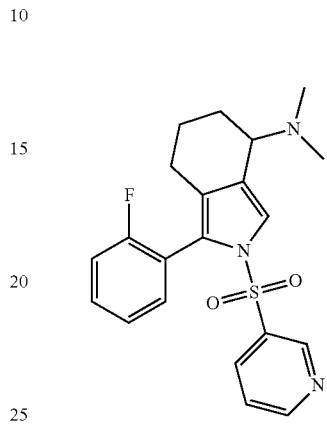

¹H NMR (500 MHz, CDCl₃): 8.90 (d, 2H), 8.42 (s, 1H), 7.68-7.73 (m, 3H), 7.25-7.38 (m, 2H), 6.85 (s, 1H), 3.86 (br, 1H), 2.45 (s, 6H), 2.59-2.65 (m, 2H), 1.43-1.81 (m, 4H)

Example 145: Preparation of 2-((3-chlorophenyl)sulfonyl)-1-(2-fluorophenyl)-N-methyl-2,4,5,6,7,8-hexahydrocyclohepta[c]pyrrol-4-amine Step 1: Preparation of 5,6,7,8-tetrahydrocyclohepta[c]pyrrol-4(2H)-one

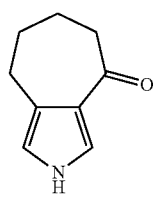 [SMILES: O=C1CCCCc2c[nH]cc21]

To a solution of 2-cyclohepten-1-one (5 g, 45.4 mmole) in tetrahydrofurane (50 me), p-toluenesulfonylmethyl isocyanide (9 g, 45.4 mmole) was added, the mixture was stirred at room temperature for 10 minutes, and then, a solution of potassium tert-butoxide (6.1 g, 54.5 mmole) in tetrahydrofurane (50 ml) was slowly added dropwise for 1 hour. In the reaction mixture, water was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:1 (v/v)) to prepare 2.2 g of the title compound (yield 32.5%).

¹H NMR (500 MHz, CDCl₃): 8.64 (br, 1H), 7.38 (t, 1H), 6.54 (s, 1H), 2.77-2.79 (m, 2H), 2.66-2.68 (m, 2H), 1.85-1.89 (m, 4H)

Step 2: Preparation of 1-bromo-5,6,7,8-tetrahydro-cyclohepta[c]pyrrol-4(2H)-one

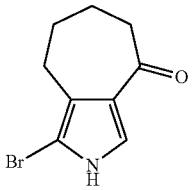

5,6,7,8-tetrahydrocyclohepta[c]pyrrol-4(2H)-one (1 g, 6.7 mmole) prepared in the step 1 was dissolved in tetrahydrofurane (70 ml), and the solution was cooled to −78° C. N-bromosuccinimide (1.3 g, 7.0 mmole) was added thereto, and then, the mixture was stirred at room temperature for 20 hours. In the reaction mixture, water was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:1 (v/v)) to prepare 430 mg of the title compound (yield 28%).

$^1$H NMR (500 MHz, CDCl$_3$): 7.54 (br, 1H), 2.65-2.73 (m, 2H), 2.58-2.61 (m, 2H), 1.82-1.95 (m, 4H)

Step 3: Preparation of 1-(2-fluorophenyl)-5,6,7,8-tetrahydrocyclohepta[c]pyrrol-4(2H)-one

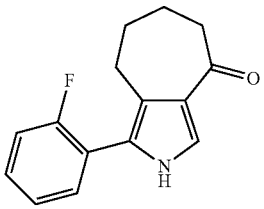 [SMILES: O=C1CCCCc2c1c[nH]c2-c1ccccc1F]

1-bromo-5,6,7,8-tetrahydrocyclohepta[c]pyrrol-4(2H)-one (500 mg, 2.2 mmole) prepared in the step 2, palladium (II) acetate (49 mg, 0.2 mmole), tris(2-methoxyphenyl)phosphine (124 mg, 0.4 mmole), potassium phosphate tribasic (1.6 g, 7.7 mmole), and 2-fluorophenyl boric acid (49 mg, 0.4 mmole) were suspended in a 1,2-dimethoxyethane:water=4:1 solution (25 ml), and the mixture was reacted at 90° C. for 1 hour. The reaction mixture was filtered through Celite, water was added to the filtrate, and the mixture was extracted with ethyl acetate. The extract was washed with saturated brine, dried over anhydrous magnesium sulfate, and concentrated under reduced pressure. The obtained residue was purified with silica gel column chromatography (ethyl acetate:n-hexane=1:1 (v/v)) to prepare 346 mg of the title compound 346 mg (yield 65%).

$^1$H NMR (500 MHz, CDCl$_3$): 7.71-7.75 (m, 2H), 7.49-7.54 (m, 2H), 7.27 (t, 1H), 2.61-2.68 (m, 2H), 2.52-2.59 (m, 2H), 1.79-1.86 (m, 4H)

Step 4: Preparation of 2-((3-chlorophenyl)sulfonyl)-1-(2-fluorophenyl)-5,6,7,8-tetrahydrocyclohepta[c]pyrrol-4(2H)-one

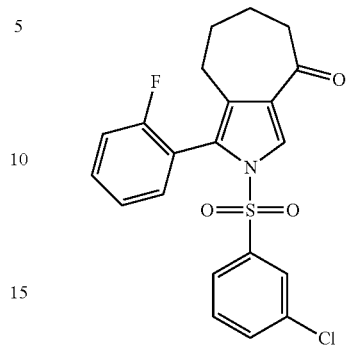

1-(2-fluorophenyl)-5,6,7,8-tetrahydrocyclohepta[c]pyrrol-4(2H)-one (50 mg, 0.2 mmole) prepared in the step 3 was dissolved in N,N-dimethylformamide (3 ml), the solution was cooled to 0° C., and sodium hydride (60% in oil) (12 mg, 0.3 mmole) was added dropwise. The reaction mixture was stirred at 0° C. for 30 minutes, and then, 3-chlorobenzenesulfonyl chloride (55 mg, 0.3 mmole) was introduced, and the mixture was stirred at room temperature for 3 hours. In the reaction mixture, water was introduced, and the mixture was extracted with ethyl acetate, and then, the separated organic layer was washed with saturated brine, dried over anhydrous magnesium sulfate, and concentrated under reduced pressure. The obtained residue was purified with silica gel column chromatography (ethyl acetate:n-hexane=1:1 (v/v)) to prepare 40 mg of the title compound (yield 46%).

$^1$H NMR (500 MHz, CDCl$_3$): 8.04 (s, 1H), 7.52-7.54 (m, 1H), 7.43-7.48 (m, 1H), 7.31-7.34 (m, 2H), 7.24 (d, 1H), 7.15-7.21 (m, 2H), 7.01 (t, 1H), 2.68-2.73 (m, 2H), 2.37-2.40 (m, 2H), 1.83-1.88 (m, 2H), 1.70-1.77 (m, 2H)

Step 5: Preparation of 2-((3-chlorophenyl)sulfonyl)-1-(2-fluorophenyl)-N-methyl-2,4,5,6,7,8-hexahydro-cyclohepta[c]pyrrol-4-amine

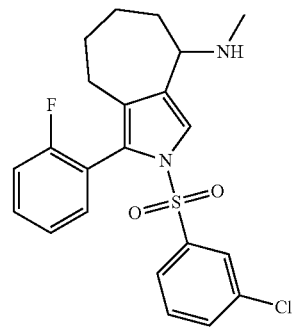 [SMILES: CNC1CCCCc2c1cn(S(=O)(=O)c1cccc(Cl)c1)c2-c1ccccc1F]

To a solution of 2-((3-chlorophenyl)sulfonyl)-1-(2-fluorophenyl)-5,6,7,8-tetrahydrocyclohepta[c]pyrrol-4(2H)-one (40 mg, 0.1 mmole) prepared in the step 4 in methanol (3 ml), tetraisopropoxytitanium(IV)(280 mg, 1 mmole) and 2M methylamine-tetrahydrofurane (0.5 ml, 1 mmole) were added, and then, the mixture was stirred at room temperature for 5 hours. Sodium borohydride (38 mg, 1 mmole) was introduced, and the mixture was stirred at room temperature for 3 hours, and then, the reaction mixture was concentrated under reduced pressure. A saturated aqueous solution of sodium bicarbonate was added thereto, and then, the mixture was extracted with ethyl acetate. The extract was washed with saturated brine, dried over anhydrous magnesium sulfate, and concentrated under reduced pressure. The obtained residue was purified with silica gel column chromatography (dichloromethane:methanol=10:1 (v/v)) to prepare 10 mg of the title compound (yield 24%).

$^1$H NMR (500 MHz, CDCl$_3$): 8.23 (s, 1H), 7.64-7.77 (m, 5H), 7.49 (d, 1H), 7.27 (m, 1H), 6.77 (s, 1H), 3.81 (br, 1H), 3.26 (s, 3H), 2.74-2.85 (m, 2H), 1.46-2.09 (m, 6H)

Example 146: Preparation of 1-(2-fluorophenyl)-N-methyl-2-(pyridin-3-ylsulfonyl)-2,4,5,6,7,8-hexahydrocyclohepta[c]pyrrol-4-amine

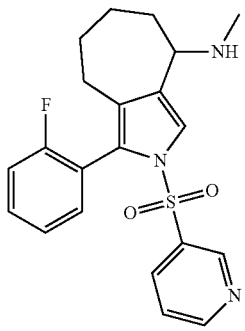 [SMILES: CNC1CCCCc2c1cn(S(=O)(=O)c1cccnc1)c2-c1ccccc1F]

12 mg of the title compound was prepared by the same method as Example 145, except that pyridin-3-sulfonyl chloride was used instead of 3-chlorobenzenesulfonyl chloride of the step 4 of Example 145 (yield 29%).

$^1$H NMR (500 MHz, CDCl$_3$): 7.48 (dd, 1H), 7.38-7.42 (m, 1H), 7.27-7.33 (m, 4H), 7.08-7.16 (m, 2H), 6.99-7.04 (m, 1H), 3.58 (br, 1H), 2.45 (s, 3H), 2.04-2.30 (m, 3H), 1.67-1.92 (m, 5H)

Example 147: Preparation of 2-((3-chlorophenyl)sulfonyl)-N-ethyl-1-(2-fluorophenyl)-2,4,5,6,7,8-hexahydrocyclohepta[c]pyrrol-4-amine

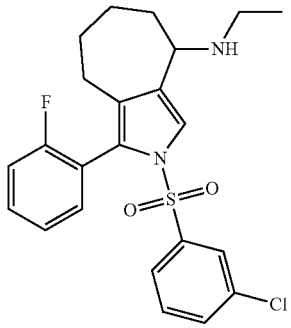 [SMILES: CCNC1CCCCc2c1cn(S(=O)(=O)c1cccc(Cl)c1)c2-c1ccccc1F]

13 mg of the title compound was prepared by the same method as Example 145, except that a 2M ethylamine-tetrahydrofurane solution was used instead of the 2M methylamine-tetrahydrofurane solution of the step 5 of Example 145 (yield 31%).

$^1$H NMR (500 MHz, CDCl$_3$): 8.25 (s, 1H), 7.65-7.78 (m, 5H), 7.51 (d, 1H), 7.33 (m, 1H), 6.72 (s, 1H), 3.83 (br, 1H), 2.74-2.85 (m, 2H), 2.51-2.55 (m, 2H), 1.46-2.09 (m, 6H), 1.15 (t, 3H)

Experimental Example

1) Preparation of Gastric Vesicles

Gastric vesicles were prepared from hog stomach by centrifugation (Edd C. Rabon et al., Preparation of Gastric H$^+$,K$^+$-ATPase, Methods in enzymology, vol. 157 Academic Press Inc., (1988), pp. 649-654). The protein contents of the prepared gastric vesicles were quantified with a Bicinchoninic Acid (BCA) kit.

2) Measurement of Effect of Inhibiting Proton Pump (H$^+$/K$^+$-ATPase) Activity The effect of inhibiting proton pump activity by the compound of the present invention was measured in a 96-well plate. In this experiment, K$^+$ specific H$^+$/K$^+$-ATPase activity was calculated based on the difference between H$^+$/K$^+$-ATPase activity in the presence of K$^+$ ions and H$^+$/K$^+$-ATPase activity in the absence of K$^+$ ions. In the 96-well plate, to negative and positive control groups, 0.5% dimethylsulfoxide (DMSO) in buffer was added, and to the test groups, the compound of the present invention was added. All the analyses were conducted at room temperature with the reaction volume of 100 μl. To a reaction buffer solution (60 mmol/l Tris-HCl buffer solution, pH 7.4) containing hog gastric vesicle, DMSO and each concentration of compound were added, and then, 10 μl of a 10 mmol/l adenosine triphosphate tris buffer solution (60 mmol/l Tris-HCl buffer solution, pH 7.4) was added to initiate an enzyme reaction. The enzyme reaction was conducted at 37° C. for 40 minutes, 50 μl of a malachite green solution (0.12% malachite green solution, 5.8% ammonium molybdate and 11% tween 20 were mixed at a ratio of 100:67:2 in 6.2 N sulfuric acid) was added to stop the reaction, and 50 μl of 15.1% sodium citrate was added. During the reaction, the amount of monophosphate (Pi) was measured at 570 nm using micro plate reader (FLUOstar Omega, BMG Company). Inhibition rate (%) was measured from the activity values of the control groups and the activity values of various concentrations of the test compound, and IC$_{50}$ of the test compound was calculated from each % inhibition value of the compound using Logistic 4-parameter function of Sigmaplot 8.0 program. The results are shown in the following Tables 1 to 4.

TABLE 1

| Example No. | IC$_{50}$ (μM) |
|---|---|
| 1 | 0.34 |
| 2 | 10 |
| 3 | 0.45 |
| 4 | 0.61 |
| 5 | 0.74 |
| 6 | 1.32 |
| 7 | 40 |
| 8 | 0.75 |
| 9 | 0.83 |
| 10 | 0.97 |
| 11 | 0.55 |
| 12 | 0.47 |
| 13 | 1.8 |
| 14 | 1.26 |
| 15 | 2.9 |
| 16 | 0.97 |
| 17 | 1.39 |
| 18 | 0.43 |
| 19 | 0.28 |
| 20 | 0.54 |
| 21 | 0.9 |
| 22 | 0.45 |
| 23 | 0.41 |
| 24 | 0.48 |
| 25 | 0.79 |
| 26 | 0.62 |
| 27 | 7.01 |

TABLE 1-continued

| Example No. | IC$_{50}$ (μM) |
| --- | --- |
| 28 | 0.59 |
| 29 | 1.28 |
| 30 | 1.04 |
| 31 | 1.34 |
| 32 | 0.45 |
| 33 | 0.32 |
| 34 | 0.69 |
| 35 | 0.84 |
| 36 | 2.54 |
| 37 | 1.49 |
| 38 | 5.82 |
| 39 | 2.51 |
| 40 | 7.69 |
| 41 | 3.88 |
| 42 | 5.43 |
| 43 | 0.43 |
| 44 | 0.65 |
| 45 | 0.55 |

TABLE 2

| Example No. | IC$_{50}$ (μM) |
| --- | --- |
| 46 | 3.27 |
| 47 | 0.47 |
| 48 | 1 |
| 49 | 2.17 |
| 50 | 1.05 |
| 51 | 0.65 |
| 52 | 0.35 |
| 53 | 0.77 |
| 54 | 0.41 |
| 55 | 0.59 |
| 56 | 1.72 |
| 57 | 0.42 |
| 58 | 5.78 |
| 59 | 1 |
| 60 | 0.42 |
| 61 | 0.77 |
| 62 | 8.75 |
| 63 | 0.61 |
| 64 | 0.84 |
| 65 | 0.94 |
| 66 | 0.5 |
| 67 | 1.26 |
| 68 | 0.84 |
| 69 | 1.62 |
| 70 | 0.43 |
| 71 | 0.67 |
| 72 | 0.48 |
| 73 | 0.67 |
| 74 | 0.52 |
| 75 | 2.14 |
| 76 | 0.49 |
| 77 | 0.41 |
| 78 | 0.46 |
| 79 | 0.77 |
| 80 | 0.62 |
| 81 | 1.14 |
| 82 | 0.66 |
| 83 | 0.98 |
| 84 | 0.39 |
| 85 | 2.19 |
| 86 | 5.95 |
| 87 | 1.44 |
| 88 | 0.51 |
| 89 | 1.19 |
| 90 | 0.52 |

TABLE 3

| Example No. | IC$_{50}$ (μM) |
| --- | --- |
| 91 | 0.69 |
| 92 | 0.35 |
| 93 | 0.34 |
| 94 | 0.47 |
| 95 | 1.72 |
| 96 | 0.8 |
| 97 | 2.82 |
| 98 | 3.62 |
| 99 | 6.78 |
| 100 | 7.24 |
| 101 | 18.66 |
| 102 | 10 |
| 103 | 1.79 |
| 104 | 50 |
| 105 | 8.5 |
| 106 | 3.3 |
| 107 | 2.86 |
| 108 | 5.65 |
| 109 | 6.24 |
| 110 | 2.89 |
| 111 | 2.57 |
| 112 | 2.86 |
| 113 | 0.31 |
| 114 | 30.1 |
| 115 | 40 |
| 116 | 26.23 |
| 117 | 2.44 |
| 118 | 40 |
| 119 | 2.16 |
| 120 | 1.5 |
| 121 | 1.5 |
| 122 | 1.5 |
| 123 | 2 |
| 124 | 4.18 |
| 125 | 4.42 |
| 126 | 4 |
| 127 | 4.53 |
| 128 | 50 |
| 129 | 40 |
| 130 | 1.5 |
| 131 | 1.5 |
| 132 | 8 |
| 133 | 2 |
| 134 | 19.74 |
| 135 | 5 |

TABLE 4

| Example No. | IC$_{50}$ (μM) |
| --- | --- |
| 136 | 15 |
| 137 | 6 |
| 138 | 7.1 |
| 139 | 9.07 |
| 140 | 7 |
| 141 | 10.61 |
| 142 | 8 |
| 143 | 5 |
| 144 | 8 |
| 145 | 2.2 |
| 146 | 4.5 |
| 147 | 7.04 |

3) Effect of Inhibiting Basal Gastric Acid Secretion in Pylorus-Ligated Rat

The measurement of effect of inhibiting basal gastric acid secretion by the compound of the present invention was conducted according to shay's rat model (Shay, H., et al., 1945, gastroenterology, 5, p 43-61). Male Sprague Dawley (SD) rats (body weight 180-220 g) were divided into X groups (n=5), and fasted while feeding only water for 18 hours. Under isoflurane anesthesia, incision of abdominal cavity of rat was made to ligate pylorus, and, immediately after the ligation, to the control groups, only an aqueous solution of 10% ethanol, 20% polyethyleneglycol (PEG) 400 and 10% Cremophor was administered into the caudal vein, and to the other groups, a test compound suspended in an aqueous solution of 10% ethanol, 20% polyethyleneglycol 400, 10% Cremophor was administered into the caudal vein at a dose of 3 mg/kg/2 ml. 5 hours after the ligation, the test animals were killed, and the stomach contents were extracted. The obtained contents were centrifuged at 4,000×g for 10 minutes to separate only supernatant, thus obtaining gastric juice. The amount and the pH of the obtained gastric juice were measured, the acidity of gastric juice was measured with 0.1 N-NaOH volume (ueq/ml) required for automatic titration of gastric juice to pH 7.0, and total acid output was calculated by multiplying the acidity of gastric juice and the amount of gastric juice.

% Inhibition activity of test compound=(total acid secretion of control group−total acid secretion of the group treated with test compound)/total acid secretion of control group×100

% inhibition activities of the representative materials were shown in the following Table 5.

TABLE 5

| Example No | % inhibition activity |
|---|---|
| 1 | 92% |
| 113 | 52% |

What is claimed is:

1. A compound represented by the following Chemical Formula 1, or a pharmaceutically acceptable salt thereof:

[Chemical Formula 1]

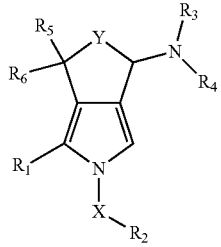

in the Chemical Formula 1,
X is —$CH_2$—, —CO—, or —$SO_2$—,
Y is $C_{1-3}$ alkylene, or —NH—,
$R_1$ is $C_{1-4}$ alkyl, benzodioxolyl, benzofuranyl, benzyl, furanyl, phenyl, pyrazolyl, pyridinyl, pyrimidinyl, or thienyl,
wherein, $R_1$ is unsubstituted; or substituted with 1 to 3 substituents respectively selected from the group consisting of $C_{1-4}$ alkyl, $C_{1-4}$ haloalkyl, $C_{1-4}$ alkoxy, $C_{1-4}$ haloalkoxy, $C_{3-6}$ cycloalkenyl, hydroxy, halogen, cyano, —COO($C_{1-4}$ alkyl), morpholino, phenyl and pyrrolidinyl
$R_2$ is imidazolyl, phenyl, pyridinyl, thienyl, or pyridinyl fused with a 5-membered heteroaromatic ring having one or two heteroatoms selected from the group consisting of nitrogen and oxygen,
wherein, $R_2$ is unsubstituted; or substituted with 1 to 3 substituents respectively selected from the group consisting of $C_{1-4}$ alkyl, $C_{1-4}$ haloalkyl, $C_{1-4}$ alkoxy, $C_{1-4}$ haloalkoxy, halogen, cyano, phenyl, phenoxy, N($C_{1-4}$ alkyl)$_2$ and —CO-morpholino,
$R_3$ is hydrogen, or $C_{1-4}$ alkyl,
$R_4$ is $C_{1-4}$ alkyl,

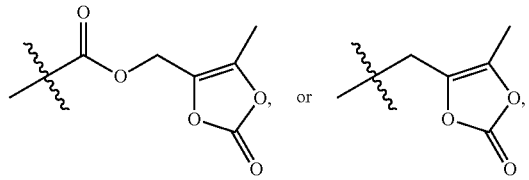

$R_5$ is hydrogen, or $C_{1-4}$ alkyl, and
$R_6$ is hydrogen, or $C_{1-4}$ alkyl.

2. The compound, or a pharmaceutically acceptable salt thereof according to claim 1, wherein $R_1$ is unsubstituted; or substituted with 1 to 3 substituents respectively selected from the group consisting of methyl, trifluoromethyl, methoxy, trifluoromethoxy, cyclopentenyl, 3ydroxyl, F, Cl, cyano, —COO(CH$_3$), morpholino, phenyl and pyrrolidinyl.

3. The compound, or a pharmaceutically acceptable salt thereof according to claim 1, wherein $R_2$ is unsubstituted; or substituted with 1 to 3 substituents respectively selected from the group consisting of methyl, trifluoromethyl, methoxy, trifluoromethoxy, difluoromethoxy, F, Cl, cyano, phenyl, phenoxy, dimethylamino and —CO-morpholino.

4. The compound, or a pharmaceutically acceptable salt thereof according to claim 1, wherein $R_1$ is phenyl, which is unsubstituted; or substituted with 1 to 3 substituents respectively selected from the group consisting of $C_{1-4}$ alkyl, $C_{1-4}$ haloalkyl, $C_{1-4}$ alkoxy, $C_{1-4}$ haloalkoxy, $C_{3-6}$ cycloalkenyl, hydroxy, halogen, cyano, —COO($C_{1-4}$ alkyl), morpholino and phenyl.

5. The compound, or a pharmaceutically acceptable salt thereof according to claim 1, wherein $R_1$ is pyridinyl, which is unsubstituted; or substituted with one substituent selected from the group consisting of $C_{1-4}$ haloalkyl, halogen, morpholino and pyrrolidinyl.

6. The compound, or a pharmaceutically acceptable salt thereof according to claim 1, wherein $R_1$ is furanyl or pyrazolyl, which is unsubstituted or substituted with $C_{1-4}$ alkyl.

7. The compound, or a pharmaceutically acceptable salt thereof according to claim 1, wherein $R_1$ is thienyl, which is unsubstituted or substituted with one or two $C_{1-4}$ alkyl.

8. The compound, or a pharmaceutically acceptable salt thereof according to claim 1, wherein $R_1$ is benzodioxolyl, benzofuranyl, benzyl or pyrimidinyl, which is unsubstituted.

9. The compound, or a pharmaceutically acceptable salt thereof according to claim 1, wherein $R_2$ is imidazolyl, phenyl, pyridinyl, thienyl, isoxazole[5,4-b]pyridinyl, or pyrazolo[3,4-b]pyridinyl, and the $R_2$ is unsubstituted; or substituted with 1 to 3 substituents respectively selected from the group consisting of $C_{1-4}$ alkyl, $C_{1-4}$ haloalkyl, $C_{1-4}$ alkoxy, $C_{1-4}$ haloalkoxy, halogen, cyano, phenyl, phenoxy, N($C_{1-4}$ alkyl)$_2$ and —CO-morpholino.

10. The compound, or a pharmaceutically acceptable salt thereof according to claim 1, wherein $R_2$ is phenyl, which is unsubstituted; or substituted with 1 to 3 substituents respectively selected from the group consisting of $C_{1-4}$ alkyl, $C_{1-4}$ haloalkyl, $C_{1-4}$ alkoxy, $C_{1-4}$ haloalkoxy, halogen, cyano, phenyl, N($C_{1-4}$ alkyl)$_2$ and —CO-morpholino.

11. The compound, or a pharmaceutically acceptable salt thereof according to claim 1, wherein $R_2$ is pyridinyl, which is unsubstituted; or substituted with 1 or 2 substituents respectively selected from the group consisting of $C_{1-4}$ alkyl, $C_{1-4}$ alkoxy, halogen and phenoxy.

12. The compound, or a pharmaceutically acceptable salt thereof according to claim 1, wherein $R_2$ is imidazolyl or isoxazole[5,4-b]pyridinyl, which is unsubstituted or substituted with $C_{1-4}$ alkyl.

13. The compound, or a pharmaceutically acceptable salt thereof according to claim 1, wherein $R_2$ is pyrazolo[3,4-b]pyridinyl, which is unsubstituted or substituted with 1 or 2 $C_{1-4}$ alkyl.

14. The compound, or a pharmaceutically acceptable salt thereof according to claim 1, wherein $R_2$ is thienyl, which is unsubstituted.

15. The compound, or a pharmaceutically acceptable salt thereof according to claim 1, wherein $R_3$ is hydrogen, and $R_4$ is $C_{1-4}$ alkyl.

16. The compound, or a pharmaceutically acceptable salt thereof according to claim 1, wherein $R_5$ and $R_6$ are hydrogen.

17. The compound, or a pharmaceutically acceptable salt thereof according to claim 1, wherein the compound is selected from the group consisting of the following compounds:

1) 2-((3-chlorophenyl)sulfonyl-1-(2-fluorophenyl)-N-methyl-2,4,5,6-tetrahydrocyclopenta[c]pyrrol-4-amine,
2) 2-((3-chlorophenyl)sulfonyl)-N,1-dimethyl-2,4,5,6-tetrahydrocyclopenta[c]pyrrol-4-amine,
3) 2-((3-chlorophenyl)sulfonyl)-N-methyl-1-phenyl-2,4,5,6-tetrahydrocyclopenta[c]pyrrol-4-amine,
4) 2-((3-chlorophenyl)sulfonyl)-N-methyl-1-(o-tolyl)-2,4,5,6-tetrahydrocyclopenta[c]pyrrol-4-amine,
5) 1-(2-chlorophenyl)-2-((3-chlorophenyl)sulfonyl)-N-methyl-2,4,5,6-tetrahydrocyclopenta[c]pyrrol-4-amine,
6) 2-((3-chlorophenyl)sulfonyl)-1-(2-(cyclopent-3-en-1-yl)phenyl)-N-methyl-2,4,5,6-tetrahydrocyclopenta[c]pyrrol-4-amine,
7) 2-((3-chlorophenyl)sulfonyl)-N-methyl-1-(2-(morpholinophenyl)-2,4,5,6-tetrahydrocyclopenta[c]pyrrol-4-amine,
8) 2-((3-chlorophenyl)sulfonyl)-N-methyl-1-(m-tolyl)-2,4,5,6-tetrahydrocyclopenta[c]pyrrol-4-amine,
9) 2-((3-chlorophenyl)sulfonyl)-1-(3-fluorophenyl)-N-methyl-2,4,5,6-tetrahydrocyclopenta[c]pyrrol-4-amine,
10) 2-((3-chlorophenyl)sulfonyl)-N-methyl-1-(3-(trifluoromethyl)phenyl)-2,4,5,6-tetrahydrocyclopenta[c]pyrrol-4-amine,
11) 2-((3-chlorophenyl)sulfonyl)-1-(4-fluorophenyl)-N-methyl-2,4,5,6-tetrahydrocyclopenta[c]pyrrol-4-amine,
12) 4-(2-((3-chlorophenyl)sulfonyl)-4-(methylamino)-2,4,5,6-tetrahydrocyclopenta[c]pyrrol-1-yl)phenol,
13) 4-(2-((3-chlorophenyl)sulfonyl)-4-(methylamino)-2,4,5,6-tetrahydrocyclopenta[c]pyrrol-1-yl)benzonitrile,
14) 2-((3-chlorophenyl)sulfonyl)-1-(4-methoxyphenyl)-N-methyl-2,4,5,6-tetrahydrocyclopenta[c]pyrrol-4-amine,
15) methyl 4-(2-((3-chlorophenyl)sulfonyl)-4-(methylamino)-2,4,5,6-tetrahydrocyclopenta[c]pyrrol-1-yl)benzoate,
16) 2-((3-chlorophenyl)sulfonyl)-N-methyl-1-(4-(trifluoromethyl)phenyl)-2,4,5,6-tetrahydrocyclopenta[c]pyrrol-4-amine,
17) 2-((3-chlorophenyl)sulfonyl)-N-methyl-1-(4-(trifluoromethoxy)phenyl)-2,4,5,6-tetrahydrocyclopenta[c]pyrrol-4-amine,
18) 2-((3-chlorophenyl)sulfonyl)-1-(2-fluoro-4-methylphenyl)-N-methyl-2,4,5,6-tetrahydrocyclopenta[c]pyrrol-4-amine,
19) 2-((3-chlorophenyl)sulfonyl)-1-(2,4-difluorophenyl)-N-methyl-2,4,5,6-tetrahydrocyclopenta[c]pyrrol-4-amine,
20) 1-(4-chloro-2-fluorophenyl)-2-((3-chlorophenyl)sulfonyl)-N-methyl-2,4,5,6-tetrahydrocyclopenta[c]pyrrol-4-amine,
21) 2-((3-chlorophenyl)sulfonyl)-1-(2,4-dichlorophenyl)-N-methyl-2,4,5,6-tetrahydrocyclopenta[c]pyrrol-4-amine,
22) 1-(5-chloro-2-fluorophenyl)-2-((3-chlorophenyl)sulfonyl)-N-methyl-2,4,5,6-tetrahydrocyclopenta[c]pyrrol-4-amine,
23) 2-((3-chlorophenyl)sulfonyl)-1-(2,5-dichlorophenyl)-N-methyl-2,4,5,6-tetrahydrocyclopenta[c]pyrrol-4-amine,
24) 2-((3-chlorophenyl)sulfonyl)-1-(3,4-difluorophenyl)-N-methyl-2,4,5,6-tetrahydrocyclopenta[c]pyrrol-4-amine,
25) 2-((3-chlorophenyl)sulfonyl)-1-(3,5-dichlorophenyl)-N-methyl-2,4,5,6-tetrahydrocyclopenta[c]pyrrol-4-amine,
26) 1-(5-chloro-2-fluoro-4-methylphenyl)-2-((3-chlorophenyl)sulfonyl)-N-methyl-2,4,5,6-tetrahydrocyclopenta[c]pyrrol-4-amine,
27) 1-benzyl-2-((3-chlorophenyl)sulfonyl)-N-methyl-2,4,5,6-tetrahydrocyclopenta[c]pyrrol-4-amine,
28) 1-(benzo[d][1,3]dioxol-5-yl)-2-((3-chlorophenyl)sulfonyl)-N-methyl-2,4,5,6-tetrahydrocyclopenta[c]pyrrol-4-amine,
29) 1-(benzofuran-5-yl)-2-((3-chlorophenyl)sulfonyl)-N-methyl-2,4,5,6-tetrahydrocyclopenta[c]pyrrol-4-amine,
30) 2-((3-chlorophenyl)sulfonyl)-N-methyl-1-(1-methyl-1H-pyrazol-4-yl)-2,4,5,6-tetrahydrocyclopenta[c]pyrrol-4-amine,
31) 2-((3-chlorophenyl)sulfonyl)-1-(furan-3-yl)-N-methyl-2,4,5,6-tetrahydrocyclopenta[c]pyrrol-4-amine,
32) 2-((3-chlorophenyl)sulfonyl)-N-methyl-1-(5-methylfuran-2-yl)-2,4,5,6-tetrahydrocyclopenta[c]pyrrol-4-amine,
33) 2-((3-chlorophenyl)sulfonyl)-N-methyl-1-(thiophen-3-yl)-2,4,5,6-tetrahydrocyclopenta[c]pyrrol-4-amine,
34) 2-((3-chlorophenyl)sulfonyl)-N-methyl-1-(4-methylthiophen-3-yl)-2,4,5,6-tetrahydrocyclopenta[c]pyrrol-4-amine,
35) 2-((3-chlorophenyl)sulfonyl)-1-(2,5-dimethylthiophen-3-yl)-N-methyl-2,4,5,6-tetrahydrocyclopenta[c]pyrrol-4-amine,
36) 2-((3-chlorophenyl)sulfonyl)-1-(6-chloropyridin-2-yl)-N-methyl-2,4,5,6-tetrahydrocyclopenta[c]pyrrol-4-amine,
37) 2-((3-chlorophenyl)sulfonyl)-N-methyl-1-(pyridin-3-yl)-2,4,5,6-tetrahydrocyclopenta[c]pyrrol-4-amine,
38) 2-((3-chlorophenyl)sulfonyl)-N-methyl-1-(2-trifluoromethyl)pyridin-3-yl)-2,4,5,6-tetrahydrocyclopenta[c]pyrrol-4-amine, 39) 2-((3-chlorophenyl)sulfonyl)-N-methyl-1-(6-trifluoromethyl)pyridin-3-yl)-2,4,5,6-tetrahydrocyclopenta[c]pyrrol-4-amine,
40) 2-((3-chlorophenyl)sulfonyl)-N-methyl-1-(6-pyrrolidin-1-yl)pyridin-3-yl)-2,4,5,6-tetrahydrocyclopenta[c]pyrrol-4-amine,
41) 2-((3-chlorophenyl)sulfonyl)-N-methyl-1-(6-morpholinopyridin-3-yl)-2,4,5,6-tetrahydrocyclopenta[c]pyrrol-4-amine,
42) 2-((3-chlorophenyl)sulfonyl)-N-methyl-1-(pyridin-4-yl)-2,4,5,6-tetrahydrocyclopenta[c]pyrrol-4-amine,
43) 1-(2-fluorophenyl)-N-methyl-2-(phenylsulfonyl)-2,4,5,6-tetrahydrocyclopenta[c]pyrrol-4-amine,
44) 1-(2-fluoro-4-methylphenyl)-N-methyl-2-(phenylsulfonyl)-2,4,5,6-tetrahydrocyclopenta[c]pyrrol-4-amine,
45) 1-(2,5-dichlorophenyl)-N-methyl-2-(phenylsulfonyl)-2,4,5,6-tetrahydrocyclopenta[c]pyrrol-4-amine,
46) 1-(2-fluorophenyl)-2-((2-methoxyphenyl)sulfonyl)-N-methyl-2,4,5,6-tetrahydrocyclopenta[c]pyrrol-4-amine,
47) 1-(2-fluoro-4-methylphenyl)-2-((3-fluorophenyl)sulfonyl)-N-methyl-2,4,5,6-tetrahydrocyclopenta[c]pyrrol-4-amine,
48) 2-((2-chlorophenyl)sulfonyl)-1-(2-fluoro-4-methylphenyl)-N-methyl-2,4,5,6-tetrahydrocyclopenta[c]pyrrol-4-amine,
49) 2-((2-chlorophenyl)sulfonyl)-1-(4-fluoro-2-methylphenyl)-N-methyl-2,4,5,6-tetrahydrocyclopenta[c]pyrrol-4-amine,
50) 2-((2-chlorophenyl)sulfonyl)-1-(2,5-dichlorophenyl)-N-methyl-2,4,5,6-tetrahydrocyclopenta[c]pyrrol-4-amine,
51) 1-(2,5-dichlorophenyl)-2-((3-fluorophenyl)sulfonyl)-N-methyl-2,4,5,6-tetrahydrocyclopenta[c]pyrrol-4-amine,
52) 1-(2-fluoro-4-methylphenyl)-N-methyl-2-(m-tolylsulfonyl)-2,4,5,6-tetrahydrocyclopenta[c]pyrrol-4-amine,
53) 1-(2,5-dichlorophenyl)-N-methyl-2-(m-tolylsulfonyl)-2,4,5,6-tetrahydrocyclopenta[c]pyrrol-4-amine,
54) 1-(2-fluoro-4-methylphenyl)-2-((3-methoxyphenyl)sulfonyl)-N-methyl-2,4,5,6-tetrahydrocyclopenta[c]pyrrol-4-amine,
55) 1-(2,5-dichlorophenyl)-2-((3-methoxyphenyl)sulfonyl)-N-methyl-2,4,5,6-tetrahydrocyclopenta[c]pyrrol-4-amine,
56) 2-((3-(dimethylamino)phenyl)sulfonyl)-1-(2-fluorophenyl)-N-methyl-2,4,5,6-tetrahydrocyclopenta[c]pyrrol-4-amine,
57) 2-((3-(difluoromethoxy)phenyl)sulfonyl)-1-(2-fluorophenyl)-N-methyl-2,4,5,6-tetrahydrocyclopenta[c]pyrrol-4-amine,
58) (3-((1-(2-fluorophenyl)-4-(methylamino)-5,6-dihydrocyclopenta[c]pyrrol-2(4H)-yl)sulfonyl)phenyl)(morpholino)methanone,
59) 1-(2-fluorophenyl)-N-methyl-2-tosyl-2,4,5,6-tetrahydrocyclopenta[c]pyrrol-4-amine,
60) 1-(2-fluoro-4-methylphenyl)-2-((4-fluorophenyl)sulfonyl)-N-methyl-2,4,5,6-tetrahydrocyclopenta[c]pyrrol-4-amine,
61) 1-(2,5-dichlorophenyl)-2-((4-fluorophenyl)sulfonyl)-N-methyl-2,4,5,6-tetrahydrocyclopenta[c]pyrrol-4-amine,
62) 2-([1,1'-biphenyl]-4-ylsulfonyl)-1-(2-fluorophenyl)-N-methyl-2,4,5,6-tetrahydrocyclopenta[c]pyrrol-4-amine,
63) 2-((3-chloro-2-methylphenyl)sulfonyl)-1-(2-fluorophenyl)-N-methyl-2,4,5,6-tetrahydrocyclopenta[c]pyrrol-4-amine,
64) 2-((2,3-dichlorophenyl)sulfonyl)-1-(2-fluorophenyl)-N-methyl-2,4,5,6-tetrahydrocyclopenta[c]pyrrol-4-amine,
65) 2-((2,4-difluorophenyl)sulfonyl)-1-(2-fluorophenyl)-N-methyl-2,4,5,6-tetrahydrocyclopenta[c]pyrrol-4-amine,
66) 2-((2-chloro-4-fluorophenyl)sulfonyl)-1-(2-fluorophenyl)-N-methyl-2,4,5,6-tetrahydrocyclopenta[c]pyrrol-4-amine,
67) 3-chloro-4-((1-(2-fluorophenyl)-4-(methylamino)-5,6-dihydrocyclopenta[c]pyrrol-2(4H)-yl)sulfonyl)benzonitrile,
68) 2-((2-chloro-4-(trifluoromethoxy)phenyl)sulfonyl)-1-(2-fluorophenyl)-N-methyl-2,4,5,6-tetrahydrocyclopenta[c]pyrrol-4-amine,
69) 2-((2-chloro-4-(trifluoromethyl)phenyl)sulfonyl)-1-(2-fluorophenyl)-N-methyl-2,4,5,6-tetrahydrocyclopenta[c]pyrrol-4-amine,
70) 2-((2,5-dichlorophenyl)sulfonyl)-1-(2-fluorophenyl)-N-methyl-2,4,5,6-tetrahydrocyclopenta[c]pyrrol-4-amine,
71) 2-((2,5-dichlorophenyl)sulfonyl)-1-(2,4-difluorophenyl)-N-methyl-2,4,5,6-tetrahydrocyclopenta[c]pyrrol-4-amine,
72) 2-((2,5-dichlorophenyl)sulfonyl)-1-(2-fluoro-4-methylphenyl)-N-methyl-2,4,5,6-tetrahydrocyclopenta[c]pyrrol-4-amine,
73) 1-(2,5-dichlorophenyl)-2-((2,5-dichlorophenyl)sulfonyl)-N-methyl-2,4,5,6-tetrahydrocyclopenta[c]pyrrol-4-amine,
74) 2-((2-chloro-5-(trifluoromethyl)phenyl)sulfonyl)-1-(2-fluorophenyl)-N-methyl-2,4,5,6-tetrahydrocyclopenta[c]pyrrol-4-amine,
75) 2-((2,6-dichlorophenyl)sulfonyl)-1-(2-fluorophenyl)-N-methyl-2,4,5,6-tetrahydrocyclopenta[c]pyrrol-4-amine,
76) 2-((3,4-dichlorophenyl)sulfonyl)-1-(2-fluorophenyl)-N-methyl-2,4,5,6-tetrahydrocyclopenta[c]pyrrol-4-amine,
77) 2-((3,5-dichlorophenyl)sulfonyl)-1-(2-fluorophenyl)-N-methyl-2,4,5,6-tetrahydrocyclopenta[c]pyrrol-4-amine,
78) 2-((3,5-dichlorophenyl)sulfonyl)-1-(2-fluoro-4-methylphenyl)-N-methyl-2,4,5,6-tetrahydrocyclopenta[c]pyrrol-4-amine,
79) 1-(2,5-dichlorophenyl)-2-((3,5-dichlorophenyl)sulfonyl)-N-methyl-2,4,5,6-tetrahydrocyclopenta[c]pyrrol-4-amine,
80) 1-(2-fluorophenyl)-N-methyl-2-((2,3,4-trichlorophenyl)sulfonyl)-2,4,5,6-tetrahydrocyclopenta[c]pyrrol-4-amine,
81) N-methyl-1-phenyl-2-((2,4,5-trichlorophenyl)sulfonyl)-2,4,5,6-tetrahydrocyclopenta[c]pyrrol-4-amine,
82) 1-(2-fluoro-4-methylphenyl)-N-methyl-2-((2,4,5-trichlorophenyl)sulfonyl)-2,4,5,6-tetrahydrocyclopenta[c]pyrrol-4-amine,
83) 1-(2,5-dichlorophenyl)-N-methyl-2-((2,4,5-trichlorophenyl)sulfonyl)-2,4,5,6-tetrahydrocyclopenta[c]pyrrol-4-amine,
84) 1-(2-fluorophenyl)-N-methyl-2-((2,4,5-trichlorophenyl)sulfonyl)-2,4,5,6-tetrahydrocyclopenta[c]pyrrol-4-amine, 85) 1-(2-fluorophenyl)-N-methyl-2-((2,4,6-trichlorophenyl)sulfonyl)-2,4,5,6-tetrahydrocyclopenta[c]pyrrol-4-amine,
86) 2-((2,6-dichloro-4-(trifluoromethyl)phenyl)sulfonyl)-1-(2-fluorophenyl)-N-methyl-2,4,5,6-tetrahydrocyclopenta[c]pyrrol-4-amine,
87) 1-(2-fluorophenyl)-N-methyl-2-(thiophen-2-ylsulfonyl)-2,4,5,6-tetrahydrocyclopenta[c]pyrrol-4-amine,
88) 1-(2-fluorophenyl)-N-methyl-2-(pyridin-3-ylsulfonyl)-2,4,5,6-tetrahydrocyclopenta[c]pyrrol-4-amine,
89) 1-(2-chlorophenyl)-N-methyl-2-(pyridin-3-ylsulfonyl)-2,4,5,6-tetrahydrocyclopenta[c]pyrrol-4-amine,
90) 1-(2-fluoro-4-methylphenyl)-N-methyl-2-(pyridin-3-ylsulfonyl)-2,4,5,6-tetrahydrocyclopenta[c]pyrrol-4-amine,
91) 1-(4-chloro-2-fluorophenyl)-N-methyl-2-(pyridin-3-ylsulfonyl)-2,4,5,6-tetrahydrocyclopenta[c]pyrrol-4-amine,
92) 1-(2,5-dichlorophenyl)-N-methyl-2-(pyridin-3-ylsulfonyl)-2,4,5,6-tetrahydrocyclopenta[c]pyrrol-4-amine,
93) 1-(5-chloro-2-fluoro-3-methylphenyl)-N-methyl-2-(pyridin-3-ylsulfonyl)-2,4,5,6-tetrahydrocyclopenta[c]pyrrol-4-amine,
94) N-methyl-2-(pyridin-3-ylsulfonyl)-1-(thiophen-3-yl)-2,4,5,6-tetrahydrocyclopenta[c]pyrrol-4-amine,
95) 2-((5-chloropyridin-311)sulfonyl)-1-(2-fluorophenyl)-N-methyl-2,4,5,6-tetrahydrocyclopenta[c]pyrrol-4-amine,
96) 1-(2-fluorophenyl)-N-methyl-2-((6-phenoxypyridin-3-yl)sulfonyl)-2,4,5,6-tetrahydrocyclopenta[c]pyrrol-4-amine,
97) 1-(2-fluorophenyl)-N-methyl-2-((3-methylisoxazolo[5,4-b]pyridin-5-yl)sulfonyl-)2,4,5,6-tetrahydrocyclopenta[c]pyrrol-4-amine,
98) 2-((2-chloro-6-methoxypyridin-3-yl)sulfonyl)-1-(2-fluorophenyl)-N-methyl-2,4,5,6-tetrahydrocyclopenta[c]pyrrol-4-amine,
99) 2-((2-chloro-6-methylpyridin-311)sulfonyl)-1-(2-fluorophenyl)-N-methyl-2,4,5,6-tetrahydrocyclopenta[c]pyrrol-4-amine,
100) 2-((2-chloro-5-methylpyridin-311)sulfonyl)-1-(2-fluorophenyl)-N-methyl-2,4,5,6-tetrahydrocyclopenta[c]pyrrol-4-amine,
101) 1-(2-fluorophenyl)-N-methyl-2-((1-methyl-1H-imidazol-2-yl)sulfonyl)-2,4,5,6-tetrahydrocyclopenta[c]pyrrol-4-amine,
102) 2-((1,3-dimethyl-1H-pyrazolo[3,4-b]pyridin-511)sulfonyl)-1-(2-fluorophenyl)-N-methyl-2,4,5,6-tetrahydrocyclopenta[c]pyrrol-4-amine,
103) N-ethyl-1-(2-fluorophenyl)-2-(pyridin-3-ylsulfonyl)-2,4,5,6-tetrahydrocyclopenta[c]pyrrol-4-amine,
104) 1-(2-fluorophenyl)-N-isopropyl-2-(pyridin-3-ylsulfonyl)-2,4,5,6-tetrahydrocyclopenta[c]pyrrol-4-amine,
105) 1-(2-fluorophenyl)-N,6,6-trimethyl-2-(pyridin-3-ylsulfonyl)-2,4,5,6-tetrahydrocyclopenta[c]pyrrol-4-amine,
106) 2-((3-chlorophenyl)sulfonyl)-1-(2-fluorophenyl)-N,6,6-trimethyl-2,4,5,6-tetrahydrocyclopenta[c]pyrrol-4-amine,
107) 2-(3-chlorobenzyl)-1-(2-fluorophenyl)-N-methyl-2,4,5,6-tetrahydrocyclopenta[c]pyrrol-4-amine,
108) 2-(3-fluorobenzyl)-1-(2-fluorophenyl)-N-methyl-2,4,5,6-tetrahydrocyclopenta[c]pyrrol-4-amine,
109) 2-benzyl-1-(2-fluorophenyl)-N-methyl-2,4,5,6-tetrahydrocyclopenta[c]pyrrol-4-amine,
110) 1-(2-fluorophenyl)-N-methyl-2-(3-methylbenzyl)-2,4,5,6-tetrahydrocyclopenta[c]pyrrol-4-amine,
111) 1-(2-fluorophenyl)-2-(3-methoxybenzyl)-N-methyl-2,4,5,6-tetrahydrocyclopenta[c]pyrrol-4-amine,
112) 2-(3-chlorobenzyl)-1-(2-fluorophenyl)-N-methyl-2,4,5,6-tetrahydrocyclopenta[c]pyrrol-4-amine,
113) 1-(2,4-difluorophenyl)-2-((3-fluorophenyl)sulfonyl)-N-methyl-2,4,5,6-tetrahydrocyclopenta[c]pyrrol-4-amine,
114) (3-chlorophenyl)(1-(2,4-difluorophenyl)-4-(methylamino)-5,6-dihydrocyclopenta[c]pyrrol-2(4H)-yl)methanone,
115) 5-((3-chlorophenyl)sulfonyl)-4-(2-fluorophenyl)-N-methyl-1,2,3,5-tetrahydropyrrolo[3,4-c]pyrrol-1-amine,
116) (5-methyl-2-oxo-1,3-dioxol-4-yl)methyl (1-(2,4-difluorophenyl)-2-((3-fluorophenyl)sulfonyl)-2,4,5,6-tetrahydrocyclopenta[c]pyrrol-4-yl)-N-methylformamide,
117) 4-(((1-(2,4-difluorophenyl)-2-((3-fluorophenyl)sulfonyl)-2,4,5,6-tetrahydrocyclopenta[c]pyrrol-4-yl)(methyl)amino)methyl)-5-methyl-1,3-dioxol-2-one,
118) (5-methyl-2-oxo-1,3-dioxol-4-yl)methyl (2-((3-chlorophenyl)sulfonyl)-1-(2-fluorophenyl)-2,4,5,6-tetrahydrocyclopenta[c]pyrrol-4-yl)-(methyl)carbamate,
119) 4-(((2-((3-chlorophenyl)sulfonyl)-1-(2-fluorophenyl)-2,4,5,6-tetrahydrocyclopenta[c]pyrrol-4-yl)(methyl)amino)methyl)-5-methyl-1,3-dioxol-2-one,
120) 1-(2-fluorophenyl)-2-((3-fluorophenyl)sulfonyl)-N-methyl-4,5,6,7-tetrahydro-2H-isoindole-4-amine,
121) 1-(2-fluorophenyl)-N-methyl-2-(m-tolylsulfonyl)-4,5,6,7-tetrahydro-2H-isoindole-4-amine,
122) 1-(2-fluorophenyl)-2-((3-methoxyphenyl)sulfonyl)-N-methyl-4,5,6,7-tetrahydro-2H-isoindole-4-amine,
123) 2-((3-(difluoromethoxy)phenyl)sulfonyl)-1-(2-fluorophenyl)-N-methyl-4,5,6,7-tetrahydro-2H-isoindole-4-amine,
124) 1-(2-fluorophenyl)-N-methyl-2-((3-(trifluoromethyl)phenyl)sulfonyl)-4,5,6,7-tetrahydro-2H-isoindole-4-amine,
125) 1-(2-fluorophenyl)-N-methyl-2-((3-(trifluoromethoxy)phenyl)sulfonyl)-4,5,6,7-tetrahydro-2H-isoindole-4-amine,
126) 2-((5-chloro-2-fluorophenyl)sulfonyl)-1-(2-fluorophenyl)-N-methyl-4,5,6,7-tetrahydro-2H-isoindole-4-amine,
127) 1-([1,1'-biphenyl]-4-yl)-2-((3-chlorophenyl)sulfonyl)-N-methyl-4,5,6,7-tetrahydro-2H-isoindole-4-amine,
128) 2-((3-chlorophenyl)sulfonyl)-N-methyl-1-(pyridin-4-yl)-4,5,6,7-tetrahydro-2H-isoindole-4-amine,
129) 2-((3-chlorophenyl)sulfonyl)-N-methyl-1-(pyrimidin-5-yl)-4,5,6,7-tetrahydro-2H-isoindole-4-amine,
130) 2-((3-(dimethylamino)phenyl)sulfonyl)-1-(2-fluorophenyl)-N-methyl-4,5,6,7-tetrahydro-2H-isoindole-4-amine,
131) 1-(2-fluorophenyl)-N-methyl-2-(pyridin-3-ylsulfonyl)-4,5,6,7-tetrahydro-2H-isoindole-4-amine,
132) N-methyl-2-(pyridin-3-ylsulfonyl)-1-(o-tolyl)-4,5,6,7-tetrahydro-2H-isoindole-4-amine,
133) 1-(2-chlorophenyl)-N-methyl-2-(pyridin-3-ylsulfonyl)-4,5,6,7-tetrahydro-2H-isoindole-4-amine,
134) 1-([1,1'-biphenyl]-4-yl)-N-methyl-2-(pyridin-3-ylsulfonyl)-4,5,6,7-tetrahydro-2H-isoindole-4-amine,
135) 1-(2,4-difluorophenyl)-N-methyl-2-(pyridin-3-ylsulfonyl)-4,5,6,7-tetrahydro-2H-isoindole-4-amine,
136) 1-(2-fluorophenyl)-2-((3-fluorophenyl)sulfonyl)-N,N-dimethyl-4,5,6,7-tetrahydro-2H-isoindole-4-amine, 137) 1-(2-fluorophenyl)-N,N-dimethyl-2-(m-tolylsulfonyl)-4,5,6,7-tetrahydro-2H-isoindole-4-amine,
138) 2-((3-chlorophenyl)sulfonyl)-1-(2-fluorophenyl)-N,N-dimethyl-4,5,6,7-tetrahydro-2H-isoindole-4-amine,
139) 1-(2-fluorophenyl)-N,N-dimethyl-2-((3-(trifluoromethyl)phenyl)sulfonyl)-4,5,6,7-tetrahydro-2H-isoindole-4-amine,
140) 1-(2-fluorophenyl)-2-((3-methoxyphenyl)sulfonyl)-N,N-dimethyl-4,5,6,7-tetrahydro-2H-isoindole-4-amine,
141) 1-(2-fluorophenyl)-N,N-dimethyl-2-((3-(trifluoromethoxy)phenyl)sulfonyl)-4,5,6,7-tetrahydro-2H-isoindole-4-amine,
142) 2-((3-(difluoromethoxy)phenyl)sulfonyl)-1-(2-fluorophenyl)-N,N-dimethyl-4,5,6,7-tetrahydro-2H-isoindole-4-amine,
143) 2-((3-(dimethylamino)phenyl)sulfonyl)-1-(2-fluorophenyl)-N,N-dimethyl-4,5,6,7-tetrahydro-2H-isoindole-4-amine,
144) 1-(2-fluorophenyl)-N,N-dimethyl-2-(pyridin-3-ylsulfonyl)-4,5,6,7-tetrahydro-2H-isoindole-4-amine,
145) 2-((3-chlorophenyl)sulfonyl)-1-(2-fluorophenyl)-N-methyl-2,4,5,6,7,8-hexahydrocyclohepta[c]pyrrol-4-amine,
146) 1-(2-fluorophenyl)-N-methyl-2-(pyridin-3-ylsulfonyl)-2,4,5,6,7,8-hexahydrocyclohepta[c]pyrrol-4-amine, and
147) 2-((3-chlorophenyl)sulfonyl)-N-ethyl-1-(2-fluorophenyl)-2,4,5,6,7,8-hexahydrocyclohepta[c]pyrrol-4-amine.

18. A pharmaceutical composition containing the compound, or a pharmaceutically acceptable salt thereof according to claim 1.

19. A pharmaceutical composition for treating peptic ulcer, gastritis or reflux esophagitis, containing the compound, or a pharmaceutically acceptable salt thereof according to claim 1 as an active ingredient.

20. A method for treating peptic ulcer, gastritis or reflux esophagitis, comprising administering an effective amount of the compound, or a pharmaceutically acceptable salt thereof according to claim 1 to a subject having or suspected to have peptic ulcer, gastritis or reflux esophagitis.

\* \* \* \* \*